US011350909B2

(12) United States Patent
Maresca et al.

(10) Patent No.: US 11,350,909 B2
(45) Date of Patent: Jun. 7, 2022

(54) CROSS AMPLITUDE MODULATION ULTRASOUND PULSE SEQUENCE

(71) Applicant: California Institute of Technology, Pasadena, CA (US)

(72) Inventors: David Maresca, Pasadena, CA (US); Daniel P. Sawyer, Pasadena, CA (US); Mikhail Shapiro, Los Angeles, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 248 days.

(21) Appl. No.: 16/387,259

(22) Filed: Apr. 17, 2019

(65) Prior Publication Data

US 2019/0314001 A1 Oct. 17, 2019

Related U.S. Application Data

(60) Provisional application No. 62/658,996, filed on Apr. 17, 2018.

(51) Int. Cl.
 *A61B 8/08* (2006.01)
 *A61B 8/14* (2006.01)
 *A61B 8/00* (2006.01)
(52) U.S. Cl.
 CPC ............ *A61B 8/481* (2013.01); *A61B 8/14* (2013.01); *A61B 8/4444* (2013.01); *A61B 8/466* (2013.01); *A61B 8/483* (2013.01)
(58) Field of Classification Search
 CPC ......... A61B 8/481; A61B 8/14; A61B 8/4444; A61B 8/466; A61B 8/483; A61B 8/00;
 (Continued)

(56) References Cited

U.S. PATENT DOCUMENTS

| 5,577,505 A | 11/1996 | Brock-Fisher et al. |
| 5,951,479 A | 9/1999 | Holm et al. |
| 6,036,940 A | 3/2000 | Ju et al. |

(Continued)

FOREIGN PATENT DOCUMENTS

| JP | 2015186494 A | * 10/2015 | ......... G01S 15/8927 |
| WO | WO 2013/104726 A1 | 7/2013 | |
| WO | WO2019/204506 | 10/2019 | |

OTHER PUBLICATIONS

Renaud, et al., "Increasing Specificity of Contrast-Enhanced Ultrasound Imaging Using the Interaction of Quasi Counter-Propagating Wavefronts: A Proof of Concept," IEEE Trans. Ultrason. Ferroelectr. Freq. Control, vol. 62, No. 10, Oct. 2015, pp. 1768-1778. (Year: 2015).*

(Continued)

*Primary Examiner* — Carolyn A Pehlke
(74) *Attorney, Agent, or Firm* — Sheila Martinez-Lemke; Weaver Austin Villenueve & Sampson LLP

(57) ABSTRACT

Certain embodiments pertain to cross-amplitude modulation (xAM) ultrasound imaging methods and systems configured to excite a first subaperture of transducer elements to transmit a first ultrasound plane wave, excite a second subaperture of transducer elements to transmit a second ultrasound plane wave noncollinear to the first ultrasound plane wave, the second ultrasound plane wave axisymmetric to the first ultrasound plane wave about a bisector, and simultaneously excite both first and second subapertures to transmit first and second ultrasound plane waves to cause an acoustic pressure above a threshold along the bisector.

27 Claims, 25 Drawing Sheets

Left subaperture

Right subaperture

(58) Field of Classification Search
CPC ............... A61B 8/4488; G01S 15/8927; G01S 7/52085; G01S 7/52093; G01S 15/8959; G01S 15/8961; G01S 15/8963

See application file for complete search history.

(56) References Cited

U.S. PATENT DOCUMENTS

| | | | |
|---|---|---|---|
| 6,042,809 | A | 3/2000 | Tournier et al. |
| 6,123,923 | A | 9/2000 | Unger et al. |
| 6,221,018 | B1 | 4/2001 | Ramamurthy et al. |
| 6,551,246 | B1* | 4/2003 | Ustuner ............... G01S 7/52026 600/447 |
| 7,448,998 | B2 | 11/2008 | Robinson |
| 8,616,060 | B2 | 12/2013 | Calle et al. |
| 2001/0031243 | A1 | 10/2001 | Unger et al. |
| 2006/0216810 | A1 | 9/2006 | Ju et al. |
| 2008/0243049 | A1 | 10/2008 | Hardy |
| 2009/0176201 | A1 | 7/2009 | Jablonski et al. |
| 2011/0044903 | A1 | 2/2011 | Borrelli |
| 2012/0184849 | A1 | 7/2012 | Sanstrom et al. |
| 2014/0058293 | A1* | 2/2014 | Hynynen ............... A61B 8/085 601/2 |
| 2014/0234904 | A1 | 8/2014 | Herbert et al. |
| 2014/0288421 | A1 | 9/2014 | Shapiro et al. |
| 2015/0147276 | A1 | 5/2015 | Ingber et al. |
| 2015/0165242 | A1 | 6/2015 | Zeng et al. |
| 2016/0089112 | A1* | 3/2016 | Rosado-Mendez ......................... G01S 7/52042 600/442 |
| 2016/0113625 | A1* | 4/2016 | Kim ..................... G01N 29/343 600/459 |
| 2016/0113699 | A1* | 4/2016 | Sverdlik ............... A61N 7/022 606/27 |
| 2016/0192906 | A1* | 7/2016 | Lee ..................... A61B 8/5207 600/438 |
| 2018/0028693 | A1 | 2/2018 | Lakshmanan et al. |
| 2018/0030501 | A1 | 2/2018 | Bourdeau et al. |
| 2018/0038922 | A1 | 2/2018 | Lu et al. |

OTHER PUBLICATIONS

Maresca D, Lakshmanan A, Lee-Gosselin A, et al. Nonlinear ultrasound imaging of nanoscale acoustic biomolecules. Appl Phys Lett. 2017;110(7):073704. doi:10.1063/1.4976105 (Year: 2017).*

Aanonsen et al., "Distortion and harmonic generation in the nearfield of a finite amplitude sound beam," The Journal of the Acoustical Society of America, vol. 75, No. 3, Mar. 1984, pp. 749-768. <doi: 10.1121/1.390585>.

B. E. Treeby, et al., "Modeling Nonlinear Ultrasound Propagation in Heterogeneous Media with Power Law Absorption Using a k-space Pseudospectral Method," J. Acoust. Soc. Am. 131, 4324 (2012).

Bourdeau, et al., "Acoustic Reporter Genes for Noninvasive Imaging of Microorganisms in Mammalian Hosts," Nature (London) 553, 86 (2018).

Dayton et al., "Molecular ultrasound imaging using microbubble contrast agents" Frontiers in Bioscience, vol. 12, No. 23, Sep. 2007, pp. 5124-5142.

Deng, et al., "Ultrasound Imaging Techniques for Spatiotemporal Characterization of Composition, Microstructure, and Mechanical Properties in Tissue Engineering," Tissue Engineering: Part B, vol. 22, No. 4, 2016, pp. 311-322. <doi: 10.1089/ten.teb.2015.0453>.

Emmer, M. et al., "Pressure-Dependent Attenuation and Scattering of Phospholipid-Coated Microbubbles at Low Acoustic Pressures," Ultrasound Medicine & Biology, vol. 35, No. 1, Jul. 2008, pp. 102-111. <doi:10.1016/j.ultrasmedbio.2008.07.005>.

Faez, T., et al., "20 Years of Ultrasound Contrast Agent Modeling", IEEE transactions on ultrasonics, ferroelectrics, and frequency control 60, 7 (2013).

Ferrara, et al., "Ultrasound Microbubble Contrast Agents: Fundamentals and Application to Gene and Drug Delivery", Annual Review of Biomedical Engineering 9, 415 (2007).

Gusev, Vitalyi, et al. "Interaction of counterpropagating acoustic waves in media with nonlinear dissipation and in hysteretic media." Wave Motion, vol. 29, No. 3, Apr. 1999, pp. 211-221.

Hamilton, et al., "On the coefficient of nonlinearity $\beta$ in nonlinear acoustics," The Journal of the Acoustical Society of America, vol. 83, No. 1, Jan. 1988, pp. 74-77. <doi: 10.1121/1.396187>.

Hamilton, et al., "Sum and difference frequency generation due to noncollinear wave interaction in a rectangular duct," The Journal of the Acoustical Society of America, vol. 81, No. 6, Jun. 1987, pp. 1703-1712.

Hansen, et al., "Contrast Imaging by Non-Overlapping Dual Frequency Band Transmit Pulse Complexes," IEEE Transactions on Ultrasonics, Ferroelectrics, and Frequency Control, vol. 58, No. 2, Feb. 2011, pp. 290-297. <URL: https://ieeexplore.ieee.org/abstract/document/5716446>.

Imbault, et al., "Robust Sound Speed Estimation for Ultrasound-Based Hepatic Steatosis Assessment," Phys. Med. Biol. 62, 3582 (2017).

Knipp, et al., "Attenuation and Backscatter Estimation Using Video Signal Analysis Applied to B-Mode Images", Ultrasonic Imaging, vol. 19, (1997) pp. 221-233.

Lakshmanan A., et al., "Molecular Engineering of Acoustic Protein Nanostructures," ACS Nano 10, 7314 (2016).

Lakshmanan et al., "Preparation of Biogenic Gas Vesicle Nanostructures for Use as Contrast Agents for Ultrasound and MRI," Nat. Protoc. 12, 2050 (2017).

Lu, et al., "Nondiffracting XWaves-Exact Solutions to Free-Space Scalar Wave Equation and Their Finite Aperture Realizations", IEEE Trans. Ultrason. Ferroelectr. Freq. Control 39, 19 (1992).

Lu, et al., "Theory and Acoustic Experiments of Nondiffracting X-Waves (medical US imaging application)," IEEE 1991 Ultrasonics Symposium, vol. 1152, Dec. 1991, pp. 1155-1159.

Maresca, et al., "Contrast-Enhanced Intravascular Ultrasound Pulse Sequences for Bandwidth-Limited Transducers," Ultrasound in Medicine & Biology, vol. 39, Apr. 2013, pp. 706-713. <doi:10.1016/j.ultrasmedbio.2012.10.020>.

Maresca, et al., "Biomolecular Ultrasound and Sonogenetics," Annual Review of Chemical Biomolecular Engineering, vol. 9, Mar. 2018, pp. 229-252. <URL: https://www.annualreviews.org/doi/10.1146/annurev-chembioeng-060817-084034>.

Maresca, et al., "Nonlinear Ultrasound Imaging of Nanoscale Acoustic Biomolecules," Appl. Phys. Lett. 110, 073704 (2017).

Montaldo, et al., "Coherent Plane-Wave Compounding for Very High Frame Rate Ultrasonography and Transient Elastography," IEEE Trans. Ultrason. Ferroelectr. Freq. Control, vol. 56, No. 3, Mar. 2009, pp. 489-506.

Ntziachristos, V. "Going deeper than microscopy: the optical imaging frontier in biology," Nature Methods, vol. 7, No. 8, Aug. 2010, pp. 603-614. <URL: https://www.nature.com/articles/nmeth.1483>.

Pasovic, et al., "Second Harmonic Inversion for Ultrasound Contrast Harmonic Imaging," Phys. Med. Biol. 56, 3163 (2011).

Provost, et al., "3D ultrafast ultrasound imaging in vivo," Physics in Medicine & Biology, Sep. 10, 2014; 59(19):L1.

Renaud G., et al., "Counter-propagating wave interaction for contrast-enhanced ultrasound imaging," Physics in Medicine & Biology, ;57(21):L9, (Oct. 9, 2012).

Renaud, et al., "Increasing Specificity of Contrast-Enhanced Ultrasound Imaging Using the Interaction of Quasi Counter-Propagating Wavefronts: A Proof of Concept," IEEE Trans. Ultrason. Ferroelectr. Freq. Control, vol. 62, No. 10, Oct. 2015, pp. 1768-1778.

Selfridge, et al., "A Theory for the Radiation Pattern of a Narrow-Strip Acoustic Transducer," Applied Physics Letters, vol. 37, No. 1, Jul. 1, 1980, pp. 35-36. <doi:10.1063/1.91692>.

Shapiro, et al., "Biogenic Gas Nanostructures as Ultrasonic Molecular Reporters," Nat. Nanotechnol. 9, 311 (2014).

Simpson, et al., "Pulse Inversion Doppler: A New Method for Detecting Nonlinear Echoes from Microbubble Contrast Agents," IEEE Transactions on Ultrasonics, Ferroelectrics, and Frequency Control, vol. 46, No. 2, Mar. 1999, pp. 372—<URL: https://ieeexplore.ieee.org/abstract/document/753026>.

Tang, et al., "Frequency and Pressure Dependent Attenuation and Scattering by Microbubbles," Ultrasound Med. & Biol., vol. 33, No. 1, 2007, pp. 164-168. <doi:10.1016/j.ultrasmedbio.2006.07.031>.

(56) References Cited

OTHER PUBLICATIONS

Tanter, M. and Fink M., "Ultrafast Imaging in Biomedical Ultrasound," IEEE Trans. Ultrason. Ferroelectr. Freq. Control 61, 102 (2014).
Ten Kate, et al., "Far-Wall Pseudoenhancement During Contrast-Enhanced Ultrasound of the Carotid Arteries: Clinical Description and In Vitro Reproduction," Ultrasound Med. Biol., vol. 38, (2012), pp. 593-600.
Tsien, R. Y., "The Green Fluorescent Protein," Annual Review of Biochemistry, vol. 67, 1998, pp. 509-544.
Walsby, "Gas Vesicles," Microbiological Reviews, vol. 58, No. 1, Mar. 1994, pp. 94-144. <URL: http://mmbr.asm.org>.
Want, K.,Sun, W., Richie, C. T., Harvey, B. K., Betzig, E., and Ji, N., "Direct Wavefront Sensing for High-Resolution In Vivo Imaging in Scattering Tissue," Nat. Commun. 6, 7276 (2015).
Wu, et al., "Measurements of the Nonlinearity Parameter B/A of Contrast Agents," Ultrasound Med. & Biol., vol. 24, No. 1, 1998, pp. 153-159.
Foster, et al. "Advances in ultrasound biomicroscopy." Ultrasound in medicine & biology, vol. 26, No. 1, 2000, pp. 1-27.
Gilad, et al., "Developing MR reporter genes: promises and pitfalls," NMR In Biomedicine, vol. 20, No. 3, May 2007, pp. 275-290.
Lauterbur PH.D., "Image formation by induced local interactions: examples employing nuclear magnetic resonance," Clinical Orthopaedics and Related Research, vol. 244, Jul. 1989, pp. 3-6.

Li, et al. "Gas Vesicle Genes Identified in *Bacillus megaterium* and Functional Expression in *Escherichia coli*," Journal of Bacteriology, vol. 180, No. 9, May 1998, pp. 2450-2458.
Schröder, et al., "Molecular Imaging using a Targeted Magnetic Resonance Hyperpolarized Biosensor," Science, vol. 314, No. 5798, Oct. 2006, pp. 446-449. <doi: 10.1126/science.1131847>.
U.S. Office Action dated Mar. 7, 2016 issued in U.S. Appl. No. 14/206,698.
U.S. Final Office Action dated Sep. 19, 2016 issued in U.S. Appl. No. 14/206,698.
U.S. Office Action dated Jun. 19, 2017 issued in U.S. Appl. No. 14/206,698.
U.S. Office Action dated Jan. 8, 2018 issued in U.S. Appl. No. 14/206,698.
U.S. Final Office Action dated Sep. 4, 2018 issued in U.S. Appl. No. 14/206,698.
Wang, et al., "Direct Wavefront Sensing for High-Resolution In Vivo Imaging in Scattering Tissue," Nat. Commun. 6, 7276 (2015).
International Search Report and Written Opinion dated Aug. 9, 2019, issued in PCT Application No. PCT/US2019/027960.
International Preliminary Report on Patentability dated Oct. 20, 2020 issued in PCT Application No. PCT/US2019/027960.
Kaufman, Beat A. and Jonathan R. Linder, "Molecular imaging with targeted contrast ultrasound", Current opinion in biotechnology, (Feb. 1, 2007), 18(1):11-6.
Pfeifer, Felicita, "Distribution, formation and regulation of Gas Vesicles", Nature Reviews Microbiology, (Oct. 2012) 10(10):705-15.

\* cited by examiner

Nonlinear Scattering of Gas Vesicles $p_{US} < p_{buckling}$ => linear scattering → $f_0$ $p_{US} > p_{buckling}$ => nonlinear scattering → $f + 2f + 3f \ldots$ Left subaperture  Right subaperture

FIG. 3A  FIG. 3B

Both subapertures (Full aperture)

Virtual Bisector

θ (degrees)

θ (degrees)

CROSS AMPLITUDE MODULATION ULTRASOUND PULSE SEQUENCE

CROSS-REFERENCES TO RELATED APPLICATIONS

This application claims priority to and benefit of U.S. Provisional Patent Application No. 62/658,996, titled "Cross Amplitude Modulation Ultrasound Pulse Sequence" and filed on Apr. 17, 2018, which is hereby incorporated by reference in its entirety and for all purposes.

FEDERALLY SPONSORED RESEARCH OR DEVELOPMENT

This invention was made with government support under Grant No. EB018975 awarded by the National Institutes of Health. The government has certain rights in the invention.

FIELD

Certain embodiments pertain generally to ultrasound imaging, and more specifically, to a cross amplitude modulation (xAM) ultrasound pulse sequence that can be used, e.g., to construct a substantially artifact-free image of nonlinearly scattering contrast agents such as gas vesicles and microbubbles.

BACKGROUND

Ultrasound is among the most widely used biomedical imaging modalities due to its ability to visualize biological tissues with high spatial and temporal resolution, and its safety, cost efficiency, and ease of use. Moreover, ultrasound can take advantage of contrast agents to visualize gene expression, other cellular processes, and the vasculature.

SUMMARY

Certain aspects pertain to a cross-amplitude modulation (xAM) ultrasound transducer system that includes one or more transducers, and first and second subapertures of transducer elements of the one or more transducers. The first subaperture configured to transmit a first ultrasound plane wave when excited. The second subaperture configured to transmit a second ultrasound plane wave when excited. The second ultrasound plane wave is noncollinear to the first ultrasound plane wave and axisymmetric to the first ultrasound plane wave about a bisector. The first and second subapertures are configured to transmit an xAM ultrasound pulse sequence by transmitting the first ultrasound plane wave, transmitting the second ultrasound plane wave, and simultaneously transmitting both the first and second ultrasound plane waves. The first and second ultrasound plane waves are configured to generate an acoustic pressure that is above a threshold along the bisector.

Certain aspects pertain to a cross-amplitude modulation (xAM) ultrasound imaging method that causes activation (excites) of a first subaperture of transducer elements to transmit a first ultrasound plane wave. The xAM ultrasound imaging method also causes excitation of a second subaperture of transducer elements to transmit a second ultrasound plane noncollinear to the first ultrasound plane wave. In one case, the first and second subapertures are part of one transducer probe. In another case, the first and second subapertures are part of two separate transducer probes. The second ultrasound plane wave is also axisymmetric to the first ultrasound plane wave about a bisector. The xAM ultrasound imaging method also causes simultaneous excitation of both the first and second subapertures of transducer elements to transmit the first and second ultrasound plane waves simultaneously. The first and second ultrasound plane waves are configured to cause an acoustic pressure above a threshold along the bisector.

These and other features are described in more detail below with reference to the associated drawings.

BRIEF DESCRIPTION OF THE DRAWINGS

FIG. 3A is an illustration of a simulation of a transmission event of an xAM ultrasound pulse sequence that transmits a first half-aperture acoustic plane wave at a cross-propagation angle of 18 degrees, according to an implementation.

FIG. 3B is an illustration of a simulation of a transmission event of an xAM ultrasound pulse sequence that transmits a second half-aperture acoustic plane wave at a cross-propagation angle of 18 degrees, according to an implementation.

DETAILED DESCRIPTION

Figure 3C:
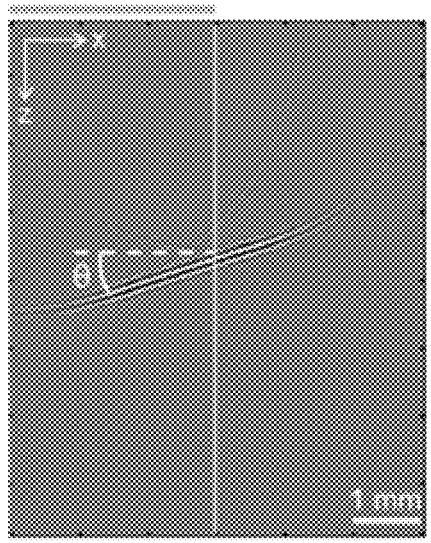
FIG. 3C is an illustration of a simulation of a transmission event of simultaneous transmission of both cross-propagating plane waves with a cross-propagation angle of 18 degrees, according to an implementation.
Figure 3C:
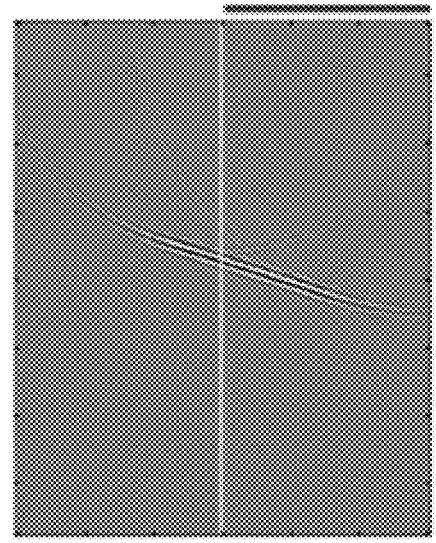
Figure 3C:
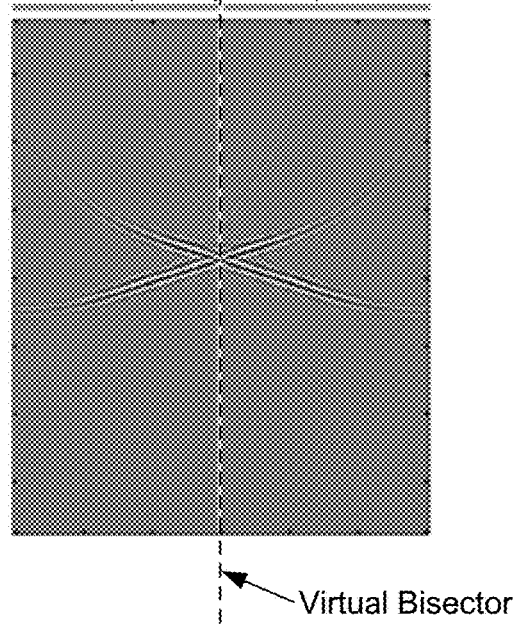

Different aspects are described below with reference to the accompanying drawings. The features illustrated in the drawings may not be to scale. Certain aspects pertain to cross-amplitude modulation (xAM) ultrasound imaging methods and systems, and ultrasound transducers that implement an xAM ultrasound pulse sequence. In certain implementations, the xAM ultrasound pulse sequence involves transmitting two cross-propagating ultrasonic plane waves (non-collinear and axisymmetric) in separate pulses and transmitted both ultrasonic plane waves simultaneously in another pulse. An example of this xAM pulse sequence is depicted in FIGS. 3A-3C. When separately transmitted, the cross-propagating ultrasonic plane waves generate a peak acoustic pressure below a buckling threshold of contrast agents such as gas vesicles or microbubbles and linear scattering is detected. When the cross-propagating ultrasonic plane waves are transmitted simultaneously (also referred to herein as "X waves"), the peak acoustic pressure where the X-waves intersect along the bisector is greater than the buckling threshold, which generates nonlinear scattering of the contrast agents. The two ultrasonic plane waves are axisymmetric about the intersecting bisector, each propagating in a direction at a cross-propagation angle θ (e.g., an angle greater than fifteen (15) degrees) from the intersecting bisector. The xAM ultrasound pulse sequence can be swept across a desired field-of-view and backscatter echo signals used to reconstruct a substantially artifact-free two-dimensional or three-dimensional image of the nonlinearly scattering contrast agents.

In the following description, numerous specific details are set forth in order to provide a thorough understanding of the presented embodiments. The disclosed embodiments may be practiced without one or more of these specific details. In other instances, well-known operations have not been described in detail to avoid unnecessarily obscuring the disclosed embodiments. While the disclosed embodiments will be described in conjunction with the specific embodiments, it will be understood that it is not intended to limit the disclosed embodiments. For example, it would be understood that while certain techniques are described with reference to imaging engineered harmonic gas vesicle variants (hGVs), these same techniques can be used to image other nonlinear scatterers such as resonant microbubbles.

I. Introduction

A. Gas Vesicles (GVs) and Engineered Harmonic GV Variants (hGVs)

Green fluorescent protein (GFP) and its analogs are widely used as contrast agents with optical microscopes to visualize gene expression and other cellular processes as discussed in Tsien, R. Y., Annual Review of Biochemistry 67, page 509 (1998). The microstructure of biological tissues can, however, restrict a photon's transport mean free path to about 1 mm which limits in vivo optical imaging applications, which is discussed in Ntziachristos, V., Nature Methods 7, page 603 (2010). In contrast, ultrasonic waves can propagate centimeters into biological tissues without losing coherence, which enables tissue scanning at the organ scale.

The basic physics of sound waves enables ultrasound to visualize biological tissues with high spatial and temporal resolution. This capability has been enhanced by the development of acoustic biomolecules—proteins with physical properties enabling them to scatter sound. The first acoustic biomolecules developed as contrast agents in ultrasound imaging, analogous to GFPs used in optical imaging, were based on a unique class of air-filled protein nanostructures called gas vesicles (GVs). The advancement of GVs has made it possible to use ultrasound to visualize the functions of cells deep inside tissues. A discussion of the development of GVs can be found in Shapiro, M. G., Goodwill, P. W., Neogy, A., Yin, M., Foster, F. S., Schaffer, D. V., and Conolly, S. M., "Biogenic Gas Nanostructures as Ultrasonic Molecular Reporters," Nat. Nanotechnol. 9, 311 (2014), which is hereby incorporated by reference in its entirety. The expression of gas vesicles (GVs), in cells allows ultrasound to image cellular functions such as gene expression in vivo, providing ultrasound with its analog of optical fluorescent proteins.

Each gas vesicle (GV) includes an air-filled hollow structure or "nanocompartment" that is enclosed by a rigid protein shell. Natural GVs (sometimes referred to herein as "native GVs") have proteins sitting on the outside of their shells that act as stiffeners to withstand hydrostatic pressure. The stiffening proteins affect the buckling, collapse, and cavitation behavior of the protein shell. In certain aspects, GVs have length on the order of about 200 nm and a rigid protein shell having a thickness of about 2 nm. Additional details regarding the structures of GVs, natural or engineered, can be found in Maresca, D., et al., "Biomolecular Ultrasound and Sonogenetics," Annu. Rev. Chem. Biomol. Eng. 9, 229 (2018) and Walsby, A. E., "Gas Vesicles," Microbiol. Rev. 58, 94 (1994), both of which are hereby incorporated by reference in their entireties.

To maximize the benefit of acoustic biomolecules to biology and medicine, physical methods are needed to discriminate between the scattering of acoustic biomolecules as contrast agents and the scattering of the surrounding tissue. Some developments for using synthetic microbubbles as contrast agents in ultrasound imaging are described in Ferrara, K., Pollard, R., and Borden, M., Annual Review of Biomedical Engineering 9, 415 (2007), Faez, T., Emmer, M., Kooiman, K., Versluis, M., van der Steen, A., and de Jong, N., IEEE transactions on ultrasonics, ferroelectrics, and frequency control 60, 7 (2013), U.S. Pat. No. 5,577,505, titled "Means for Increasing Sensitivity in Non-Linear Ultrasound Imaging Systems," and filed on Feb. 6, 1996, Simpson, D. H., Chin, C. T., and Burns, P. N., IEEE transactions on ultrasonics, ferroelectrics, and frequency control 46, 372 (1999), Hansen, R. and B. A. Angelsen, IEEE transactions on ultrasonics, ferroelectrics, and frequency control 58, 290 (2011), Maresca, D., Renaud, G., van Soest, G., Li, X., Zhou, Q., Shung, K. K., de Jong, N., and van der Steen, A. F., Ultrasound in medicine & biology 39, 706 (2013), Renaud, G., Bosch, J. G., Ten Kate, G. L., Shamdasani, V., Entrekin, R., de Jong, N., and van der Steen, A. F., Physics in medicine and biology 57, L9 (2012), which are hereby incorporated by reference in their entireties. Some techniques for imaging GVs as contrast agents using ultrasound are discussed in Shapiro, M. G., Goodwill, P. W., Neogy, A., Yin, M., Foster, F. S., Schaffer, D. V., and Conolly, S. M., "Biogenic Gas Nanostructures as Ultrasonic Molecular Reporters," Nat. Nanotechnol. 9, 311 (2014) and in U.S. patent application Ser. No. 14/206,698, titled "GAS VESICLE ULTRASOUND CONTRAST AGENTS AND METHOD OF USING THE SAME," and filed on Mar. 12, 2014, which are both hereby incorporated by reference in their entireties. Moreover, it has been shown that gene clusters encoding GVs could be expressed heterologously in engineered cells and serve as acoustic reporter genes as discussed in Bourdeau, R. W., Lee-Gosselin, A., Lakshmanan, A., Farhadi. A., Kumar, S. R., Nety, S. P., and Shapiro, M. G., "Acoustic Reporter Genes for Noninvasive Imaging of Microorganisms in Mammalian Hosts," Nature (London) 553, 86 (2018), which is hereby incorporated by reference for this discussion.

Generally, natural GVs behave as linear ultrasound scatterers at acoustic pressures above and below 300 kPa. Harmonic GV variants (hGVs) can be engineered, however, with fewer stiffening proteins so as to buckle and scatter higher harmonics at peak acoustic pressures of 300 kPa or higher. The bucking threshold of 300 kPa corresponds to a mechanical index of 0.08, which is below the FDA safety requirement of 1.9. Some examples of molecular engineered hGVs that buckle and scatter higher harmonics at acoustic pressures of 320 kPa are discussed in Lakshmanan A., Farhadi, A., Nety, Lee-Gosselin, S. P., A., Bourdeau, R. W., Maresca, D., and Shapiro, M. G., "Molecular Engineering of Acoustic Protein Nanostructures," ACS Nano 10, 7314 (2016) and in Maresca, D., Lakshmanan, A., Lee-Gosselin, A., Melis, J. M., Ni, Y. L., Bourdeau, R. W., Kochmann, D. M., and Shapiro, M. G., "Nonlinear Ultrasound Imaging of Nanoscale Acoustic Biomolecules," Appl. Phys. Lett. 110, 073704 (2017), both of which are hereby incorporated by reference in their entireties. In certain aspects, hGVs can be engineered to remove and/or alter one or more of the stiffening proteins to engineer hGVs that buckle, collapse, and/or cavitate at a particular acoustic pressure threshold.

Engineered harmonic gas vesicles (hGVs) can be engineered and harvested from host bacteria or archaea using various techniques. In one example, Anabaena GVs are cultured and transferred to sterile separating funnels, and the buoyant cells allowed to float to the top and separated from the spent media over a 48 hour period. The GVs are then harvested using hypertonic lysis. Purification can be performed by repeated centrifugally-assisted flotation followed by resuspension. Wild-type Ana GVs are then stripped of their outer GvpC layer by treatment with κ-M urea solution to obtain hGVs. Next, two rounds of centrifugally-assisted flotation are followed by removal of the subnatant layer to ensure complete removal of native GvpC.

The hGVs vary in shape depending on the type of genetic host. In some cases, the hGVs are ellipsoid in shape or cylindrical with cone-shaped end portions. The diameter and length of the hGVs also varies. Typically hGVs have a diameter that ranges from about 115 nm to about 302 nm. In some cases, hGVs have a diameter of 60 nm. In some cases, hGVs have a length that ranges from about 440 nm to about 600 nm. In other cases, hGVs have a length that ranges from about 287 nm to about 513 nm. In yet other cases, hGVs have a length that ranges from about 150 nm to about 348 nm.

In certain aspects, hGVs have been engineered with a buckling threshold in a range between 200 kPa to 1000 kPa. In one aspect, hGVs have been engineered with a buckling threshold of about 400 kPa. In another aspect, hGVs have been engineered with a buckling threshold of about 600 kPa. In certain aspects, hGVs have been engineered with a collapse and/or cavitation threshold in a range between 150 kPa to 2000 kPa. In one aspect, hGVs have been engineered with a collapse and/or cavitation threshold of about 600 kPa. In another aspect, hGVs have been engineered with a collapse and/or cavitation threshold of about 900 kPa.

B. Amplitude Modulation

Harmonic GV variants (hGVs) can be used as contrast agents in ultrasound imaging by taking advantage of the difference between backscatter echoes from nonlinearly scattering hGVs and linearly scattering surrounding tissue when ultrasonic waves generate acoustic pressures above the buckling threshold. For example, amplitude modulation (AM) ultrasound pulse sequences have been used to exploit the dissimilar hGV responses below and above their buckling threshold to enable non-linear imaging of hGVs in vitro, in ovo, and in vivo. An example an AM ultrasound pulse sequence that can be used to image hGVs can be found in Maresca, D., Lakshmanan, A., Lee-Gosselin, A., Melis, J. M., Ni, Y. L., Bourdeau, R. W., Kochmann, D. M., and Shapiro, M. G., "Nonlinear Ultrasound Imaging of Nanoscale Acoustic Biomolecules," Appl. Phys. Lett. 110, 073704 (2017) which is hereby incorporated by reference in its entirety. An example of an ultrasound AM pulse sequence being used to image microbubbles is described in U.S. Pat. No. 5,577,505 titled "Means for Increasing Sensitivity in Non-Linear Ultrasound Imaging Systems," and filed on Feb. 6, 1996, which is hereby incorporated by reference in its entirety. In the typical AM imaging pulse sequence, a transducer transmits two half-amplitude transmissions separately, and a third full-amplitude transmission. The transmissions in the AM pulse sequence are collinear transmissions. The full-amplitude transmission creates acoustic pressures above the hGV buckling threshold, triggering hGV harmonic scattering, while the half-amplitude transmissions create pressures below hGV buckling to trigger linear scattering. This scattering response difference in hGV echoes persists after the subtraction, while linear echoes from surrounding linear scattering tissue scale in amplitude and are canceled. The AM technique digitally subtracts the backscattered echoes of the two half-amplitude transmissions from the backscattered echoes of the third, full-amplitude transmission to generate an image of the buckling hGVs. However, the in vivo specificity of AM imaging of hGVs can be compromised by nonlinear wave propagation artifacts. These artifacts resulting from AM imaging could lead to misclassification of biological tissue as hGVs.

In highly nonlinear features (e.g., features with a nonlinearity parameter of B/A that is two (2) orders of magnitude higher than surrounding tissue), ultrasonic waves experience amplitude-dependent attenuation and amplitude-dependent speed of sound. A discussion of amplitude-dependent attenuation in microbubbles is discussed in Emmer, M., Vos, H. J., Goertz, D. E., van Wamel, A., Versluis, M., and de Jong, N., "Pressure-Dependent Attenuation and Scattering of Phospholipid-Coated Microbubbles at Low Acoustic Pressures," Ultrasound Med. Biol. 35, 102 (2009) and Tang, M. X. and Eckersley, R. J., "Frequency and Pressure Dependent Attenuation and Scattering by Microbubbles," Ultrasound Med. Biol. 33, 164 (2007), which is hereby incorporated by reference in its entirety. A discussion of the measurement of the nonlinearity parameter B/A is discussed in Wu, J. and Tong, J., "Measurements of the Nonlinearity Parameter B/A of Contrast Agents," Ultrasound Med. Biol. 24, 153 (1998), which is hereby incorporated by reference in its entirety. As a result of the amplitude-dependent attenuation and amplitude-dependent speed, the high-amplitude pulse of an AM sequence gets distorted in proportions that do not scale linearly with the low-amplitude pulses of the AM sequence. The ultrasonic waves carry that distortion as they travel forward in the medium. This phenomenon has been reported in microbubble inclusions in Ten Kate, G. L. et al., "Far-Wall Pseudoenhancement During Contrast-Enhanced Ultrasound of the Carotid Arteries: Clinical Description and In Vitro Reproduction," Ultrasound Med. Biol. 38, 593 (2012), which is hereby incorporated by reference in its entirety. While not wishing to be bound by any particular theory, it is believed that this same phenomenon is the cause of the nonlinear artifacts distal to the hGV inclusions and other nonlinear scatterers. Also, it has been established that, in a medium exhibiting quadratic elastic nonlinearity, the interaction of two ultrasonic waves propagating in the same direction exhibits a cumulative nonlinear interaction as discussed in Aanonsen, S. I., Barkve, T., J. Tjotta, N., and Tjotta, S., "Distortion and Harmonic Generation in the Nearfield of a Finite Amplitude Sound Beam," J. Acoust. Soc. Am. 75, 749 (1984), which is hereby incorporated by reference in its entirety. With a typical AM pulse sequence, images are reconstructed line by line along the wave propagation direction. The high amplitude pulse of the AM sequence has amplitude that is twice the amplitude of each of the half-amplitude pulses where all the waves collinearly propagate. The high amplitude pulse generates acoustic pressures higher than the buckling threshold in the wave propagation direction and is subject to cumulative nonlinear interaction effects.

On the other hand, imaging methods that use the nonlinear interaction of ultrasonic waves propagating in opposite, collinear directions are inefficient and impractical. Mathematical aspects of waves propagation theory are described in Gusev, V., Bailliet, H., Lotton, P., and Bruneau, M., "Interaction of Counterpropagating Acoustic Waves in Media with Nonlinear Dissipation and in Hysteretic Media," Wave Motion 29, 211 (1999), which is hereby incorporated by reference in its entirety. Another example of a method based on counter-propagating acoustic waves is described in Renaud G., Bosch, J. G., Ten Kate, G. L., Shamdasani, V., Entrekin, R., de Jong, N., Van der Steen, A. F., "Counter-propagating wave interaction for contrast-enhanced ultrasound imaging," Physics in Medicine & Biology; 57(21):L9, (2012 Oct. 9) and in PCT publication WO2013104726A1, both of which are hereby incorporated by reference in their entireties. In yet another technique, a pair of subwavelength elements of an ultrasound transducer array is used to transmit circular wave pulses that are quasi-counterpropagative in the near field. An example of this technique is discussed in Renaud, G., Bosch, J. G., van der Steen, A. F., and de Jong. N., "Increasing Specificity of Contrast-Enhanced Ultrasound Imaging Using the Interaction of Quasi Counter-Propagating Wavefronts: A Proof of Concept," IEEE Trans.

Ultrason. Ferroelectr. Freq. Control 62, 1768 (2015), which is hereby incorporated by reference in its entirety. In this quasi-counterpropagative near field technique, spherical wavefronts are used and the cross-propagation angle varies with depth. This technique is restricted to the near field and to generating an increased acoustic pressure at a point. Moreover, this technique generates images with low contrast compared to conventional ultrasound images because it is limited to using two elements of an ultrasound transducer that often contains more than one hundred elements.

Figure 1:
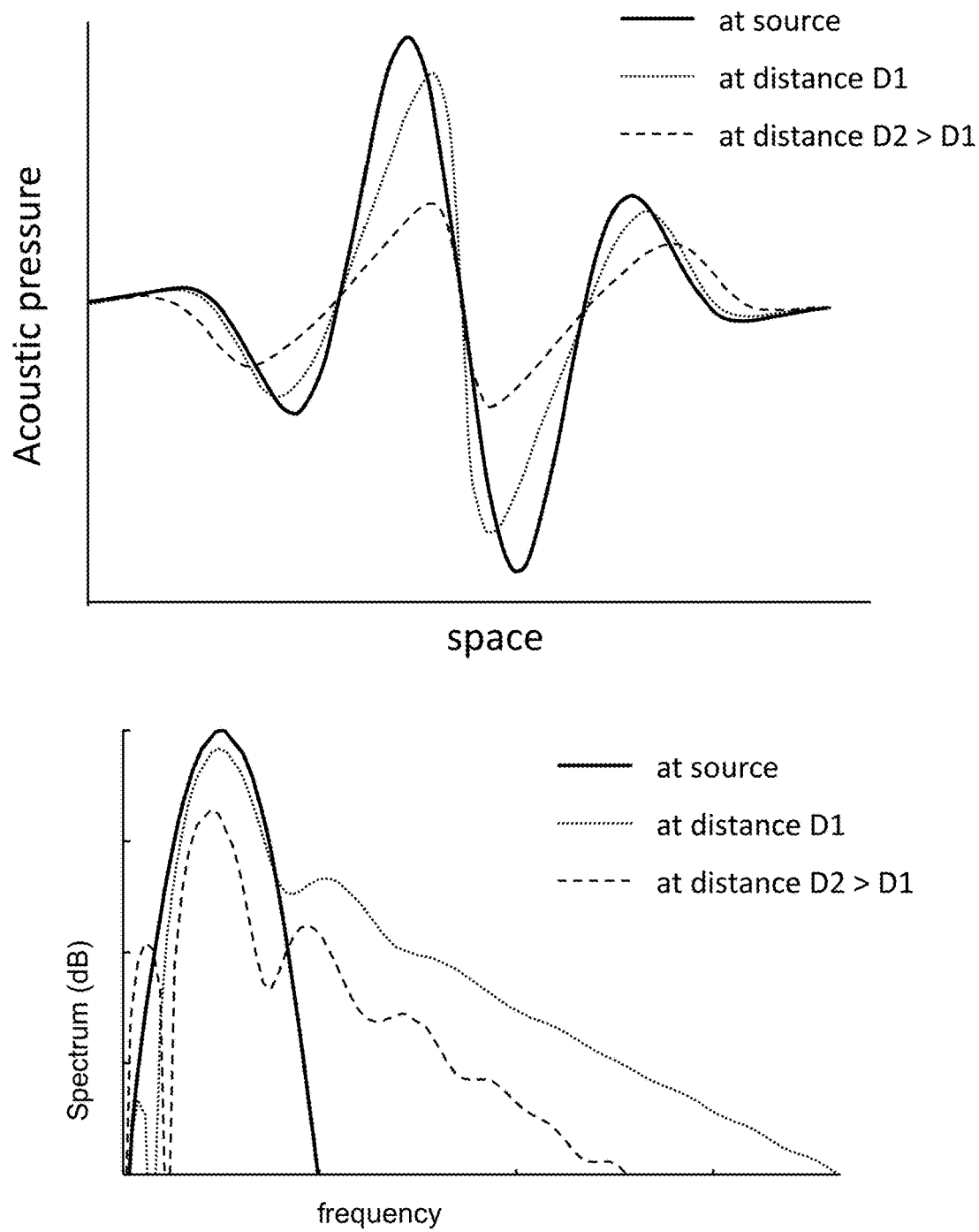
FIG. 1 includes two plots of the nonlinear phenomena, according to an implementation.
Figure 2:
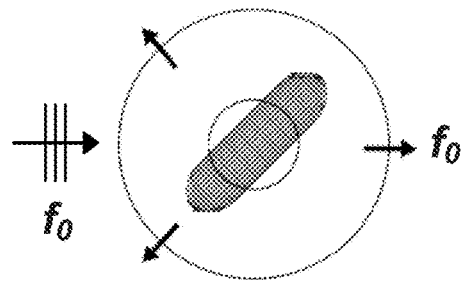
FIG. 2 is a schematic diagram of the linear and nonlinear scattering of engineered gas vesicles, according to an implementation.
Figure 2:
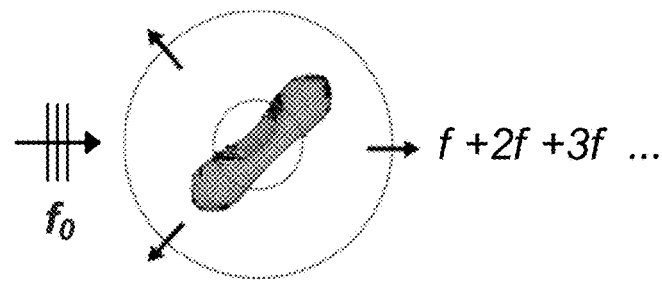

FIGS. 1 and 2 illustrate respectively two types of nonlinear phenomena that occur while imaging a biological medium including nonlinearly scattering acoustic biomolecules. The first type is due to nonlinear frequency components accumulating as the wave propagates through a biological medium. The second type is due to the nonlinear behavior of the acoustic biomolecules (e.g., hGVs). FIG. 1 includes two plots of the nonlinear wave propagation history of a single acoustic plane wave propagating through a biological medium containing biomolecules according to an implementation. As shown, the nonlinear frequency components accumulate with depth as the wave propagates through tissue before being attenuated. This phenomenon, amplified during the collinear interaction of two wavefronts, leads to nonlinear propagation artifacts distal to the nonlinear scatterers (e.g., hGVs) inclusions. FIG. 2 is a plot of the nonlinear behavior of hGVs insonified above their buckling pressure, enabling their detection. FIG. 2 is a schematic diagram of the linear and nonlinear scattering of engineered gas vesicles. As shown, the hGVs cause linear scattering when the peak acoustic pressure if below the critical buckling threshold and cause nonlinear scattering above the critical buckling threshold.

As discussed above, certain engineered hGVs have been shown to exhibit a nonlinear scattering behavior in response to acoustic pressures above 300 kPa. Also, amplitude modulated (AM) ultrasound pulse sequences that excite both the linear and nonlinear GV scattering regimes have been shown effective at distinguishing the hGVs from linear scatterers like soft biological tissues. Unfortunately, the in vivo specificity of AM ultrasound imaging is systematically compromised by the nonlinearity added by the hGVs to propagating waves, resulting in strong image artifacts from linear scatterers downstream of GV inclusions.

II. Nonlinear Interaction of Cross-Propagating Waves in Cross-Amplitude Modulation (xAM) Systems and Methods The cross-amplitude modulation (xAM) technique is a biomolecular ultrasound imaging paradigm that aims at minimizing wave propagation-related harmonics using propagation symmetry considerations while being able to capture local acoustic biomolecules' harmonics to ensure their specific in vivo detection. Wave propagation-related harmonics is discussed in Pasovic, M., Danilouchkine M., Faez, T., van Neer. P. L., Cachard, C., van der Steen, A. F., Basset, O., and de Jong, N., "Second Harmonic Inversion for Ultrasound Contrast Harmonic Imaging," Phys. Med. Biol. 56, 3163 (2011), which is hereby incorporated by reference in its entirety.

Certain aspects described herein pertain to cross-amplitude modulation (xAM) techniques that implement cross-propagating plane-wave ultrasound transmissions of finite aperture X waves. In some cases, these xAM techniques can achieve quasi-artifact-free in vivo imaging of nonlinear scatterers. While not wanting to be bound by theory or mechanism, it is believed that this quasi-artifact-free characteristic of xAM techniques derives from counterpropagating wave interaction theory, which predicts that, in media exhibiting quadratic elastic nonlinearity like biological tissue, the nonlinear interaction of counterpropagating acoustic waves is inefficient. In contrast, xAM techniques transmit noncollinear cross-propagating ultrasound plane waves. By transmitting cross-propagating plane waves, the cumulative nonlinear interaction effects due to collinear wave propagation is reduced while generating a transient peak acoustic pressure at the intersection of the two plane waves.

In certain implementations, an xAM method includes transmitting an xAM pulse sequence of two ultrasonic plane waves propagating in non-collinear directions in separate pulses and another pulse with both ultrasonic plane waves transmitted simultaneously. Each of the ultrasonic plane waves generate an acoustic pressure below a buckling threshold of the scatterers. When the cross-propagating plane waves (also referred to herein as "X waves") are transmitted separately, backscatter echoes from linear scattering are detected. When the ultrasonic plane waves are transmitted simultaneously, the acoustic pressure at their bisector intersection is greater than the buckling threshold and generates non-linear scattering along the intersection. When the X waves simultaneously, backscatter echoes from nonlinear scattering from the nonlinear scatterers is detected and the linear scattering from the surrounding media. The backscatter echoes from the ultrasonic plane waves transmitted separately are digitally subtracted from the backscatter echoes of the simultaneous transmission to capture backscatter echo data from nonlinear scatterers at the bisector intersection. The xAM pulse sequence can be swept to different locations to generate backscatter echoes that can be used to construct two-dimensional and three-dimensional images of the nonlinear scatterers. In certain cases, the xAM technique can efficiently minimize propagation nonlinearity while allowing depth-invariant, nonlinear imaging of acoustic biomolecules and other nonlinear scattering features in a linearly scattering medium. As discussed further below with reference to certain Figures, the xAM technique can prevent cumulative distortion of the amplitude modulation wave code, suppress nonlinear propagation artifacts distal to highly nonlinear hGV inclusions, and enable highly specific in vivo nonlinear ultrasound imaging of hGVs.

A. Cross-Amplitude Modulation (xAM) Pulse Sequence

Certain implementations pertain to an xAM imaging method that uses an N-element aperture of ultrasonic transducers in a transducer array to transmit a cross-amplitude (xAM) pulse sequence. The N-element aperture includes a first set of transducer elements (first subaperture), a second set of transducer elements (second subaperture), and a virtual bisector between the first and second subapertures. In this xAM pulse sequence, the first set of transducer elements (first subaperture) transmits a plane wave in a direction at a cross-propagation angle ($\theta$) from the bisector, the second set of transducer elements (second subaperture) transmits an axisymmetric plane wave about the bisector, and both sets of transducer elements transmit the plane waves simultaneously. The two plane waves are noncollinear. The two plane waves separately generate an acoustic pressure less than a threshold value (e.g., buckling threshold, collapse threshold, or cavitation threshold). When transmitted simultaneously, the plane waves generate a peak acoustic pressure above the threshold value where the plane waves intersect along the bisector. Different N-element apertures of the transducer array may be activated at different times to sweep the xAM pulse sequence across a desired field-of-view.

Figure 9A:
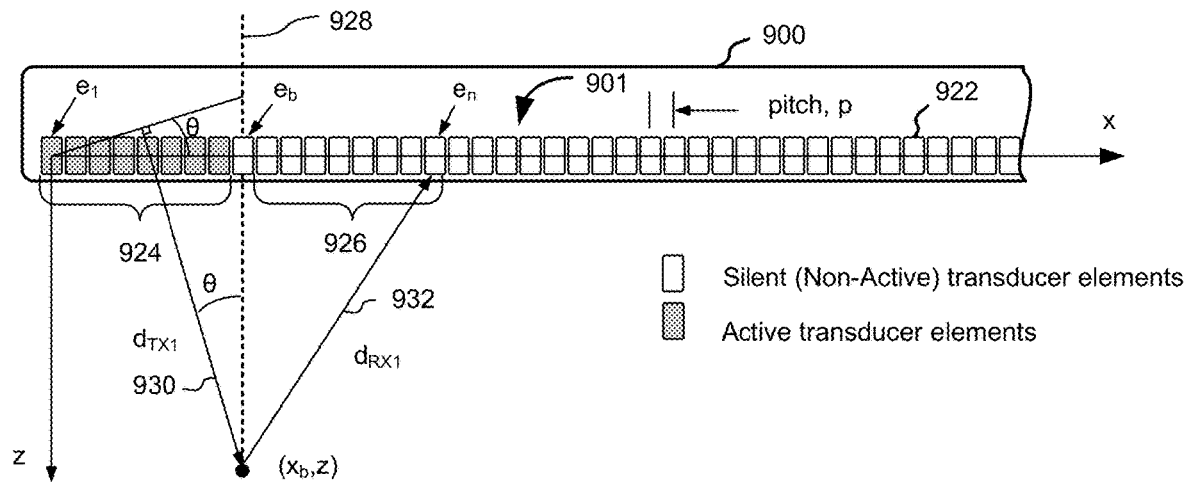
FIG. 9A is a cross-sectional drawing of a portion of an ultrasound transducer probe during transmission of a first ultrasound plane wave of the xAM pulse sequence from a left half-aperture of a narrow-strip acoustic linear transducer array, according to an implementation.
Figure 9B:
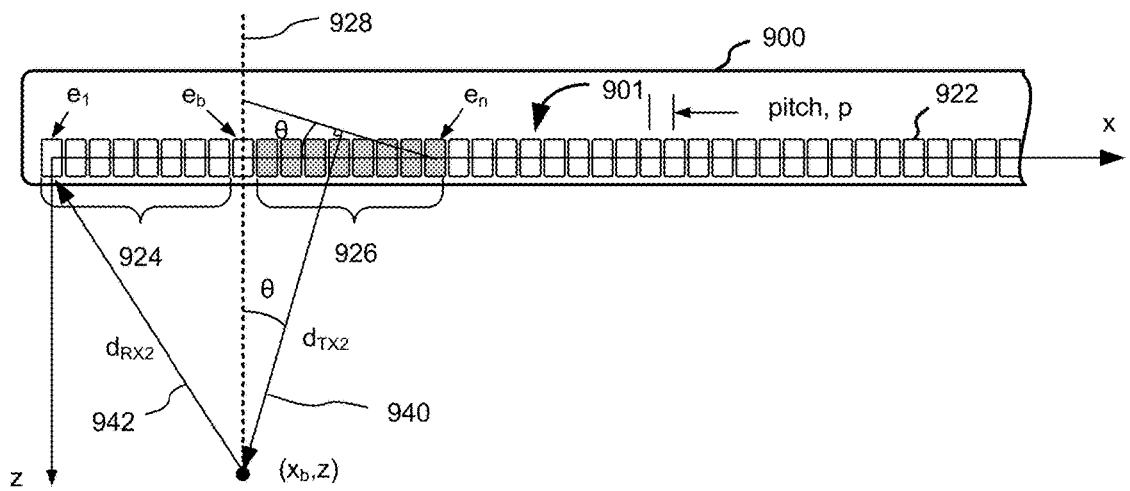
FIG. 9B is a cross-sectional drawing of the portion of the ultrasound transducer probe in FIG. 9A during transmission of a second ultrasound plane wave of the xAM pulse sequence from the right half-aperture, according to an implementation.
Figure 9C:
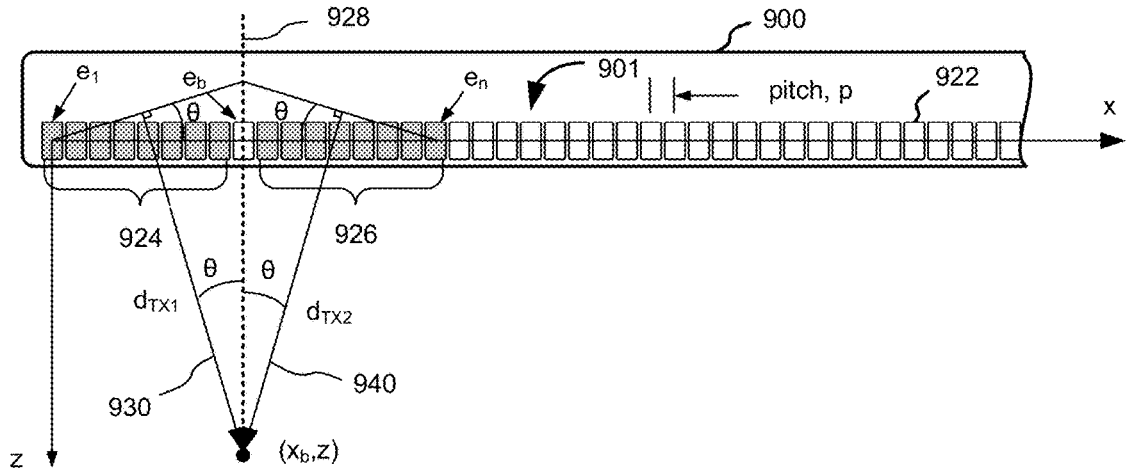
FIG. 9C is a cross-sectional drawing of the portion of the ultrasound transducer probe in FIG. 9A during simultaneous transmission of cross-propagating ultrasound plane waves of the xAM pulse sequence from both half-apertures, according to an implementation.

For example, consider an N-element aperture of a linear array of ultrasonic transducer elements (i.e. N ultrasonic transducer elements of the linear array being used to generate one xAM pulse sequence). In this example, the xAM pulse sequence includes: (1) using ultrasonic transducer elements 1 to N/2 to transmit a tilted plane wave at an angle θ with respect to the transducer array and the bisector, (2) using the elements N/2+1 to N to transmit an axisymmetric plane wave about the bisector, and (3) transmitting the previous two plane waves simultaneously. In some cases, the transducer elements of the N-element aperture are adjacent each other in sequence. In other examples, there may be one or more inactive transducer elements between the two sets of active ultrasonic transducer elements in (1) and (2) or interspersed within the two sets of ultrasonic transducer elements active in (1) and (2). In one aspect, an example of which is illustrated in FIGS. 9A, 9B, and 9C, there is an inactive transducer element between the two subapertures. Additional or fewer inactive ultrasonic transducer elements can be used. In another aspect, the one or more inactive transducer elements may be interspersed within the active transducer elements. For example, the xAM pulse sequence includes: (1) using transducer elements 1, 3, 5, 7, 9, and 11 to transmit a tilted plane wave in a direction at a cross-propagation angle θ with respect the intersecting bisector and/or the array, (2) using transducer elements 13, 15, 17, 19, 21, and 23 to transmit the axisymmetric plane wave, and (3) transmitting the two plane waves simultaneously.

In certain implementations, an xAM pulse sequence can be used to detect buckling hGVs and other nonlinear scatterers with high specificity. Certain implementations of the xAM pulse sequence result in a peak positive pressure of each of the single tilted plane waves that excites scatterers in the linear scattering regime, while the amplitude at the doubled X-wave intersection is above the buckling threshold of the hGVs to excite the hGVs in the nonlinear scattering regime. By digitally summing the echoes from the two plane-wave transmissions and then digitally subtracting them from the echoes of the X-wave transmissions, nonzero differential hGV signals are solely retrieved, while the echoes of surrounding linear scatterers cancel.

FIGS. 3A-3C include illustrations of simulations of the transmission events of three pulses respectively of an xAM pulse sequence that uses a cross-propagation angle of 18 degrees, according to an implementation. In this example, the xAM pulse sequence includes: (1) activating (exciting) ultrasonic transducer elements 1 to N/2 (left subaperture) of a linear transducer array to transmit a tilted plane wave at an angle θ of 18 degrees with respect to the array and/or a virtual bisector, (2) activating the ultrasonic transducer elements N/2+1 to N (right subaperture) of the linear transducer array to transmit a symmetric plane wave at an angle θ of 18 degrees, and (3) transmitting cross-propagating plane waves by activating (i.e. applying voltages) ultrasonic transducer elements from both right and left subapertures simultaneously. The simulation was performed in a homogeneous and isotropic water medium. FIG. 3A illustrates a simulation of a transmission event (1) of an xAM pulse sequence that transmits a half-aperture acoustic plane wave by a left subaperture of a linear transducer array at a cross-propagation angle of 18 degrees, according to an implementation. The plane-wave transmission is transmitted by ultrasonic transducer elements of the left subaperture of a linear transducer array. FIG. 3B illustrates a simulation of a transmission event (2) of the xAM pulse sequence of that transmits a half-aperture acoustic plane wave with the other half (right subaperture) of the linear transducer array. The half-aperture acoustic plane wave transmitted in FIG. 3A is noncollinear and axisymmetric about the virtual bisector to the half-aperture acoustic plane wave transmitted in FIG. 3B. FIG. 3C illustrates a simulation of the transmission event (3) of simultaneous transmission of both cross-propagating plane waves at a cross-propagation angle of 18 degrees by activating the transducer elements of half-apertures (subapertures) simultaneously. FIG. 3C also illustrates a virtual bisector between the two half-apertures of the full aperture. The virtual bisector bisects the full aperture into left and right subapertures and is normal to a plane at the surface of the transducer elements of the linear transducer array. The two cross-propagating X waves depicted in FIG. 3C intersect along the virtual bisector between the two half-apertures. Particles of the insonified medium along the bisector shown in FIG. 3C experience the same wave amplitude for each of pulses (1) and (2), and twice the amplitude for pulse (3).

Figure 4:
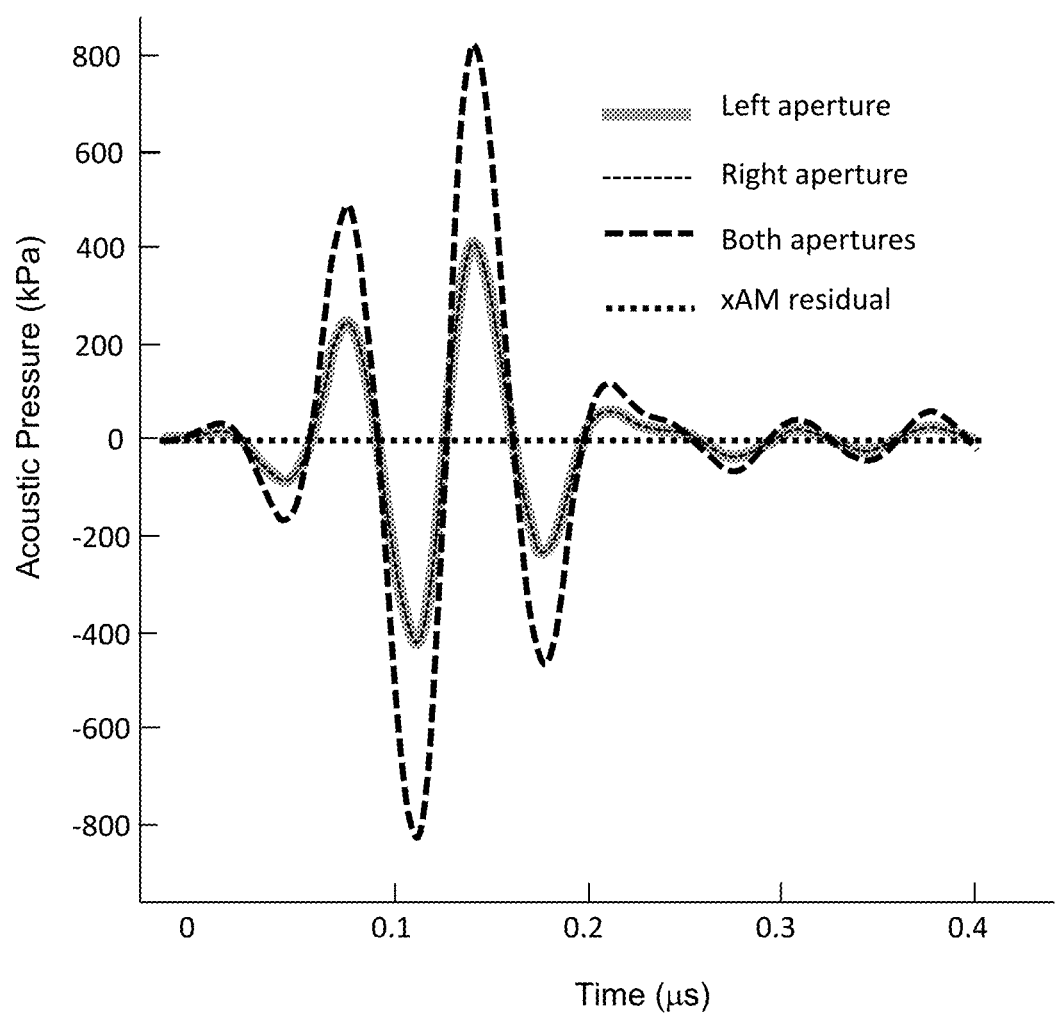
FIG. 4 is a plot of acoustic pressure versus time along the virtual bisector for the simulated waveforms of the xAM ultrasound pulse sequence of FIGS. 3A-3C, according to an implementation.

FIG. 4 illustrates a plot of acoustic pressure versus time along the virtual bisector for the simulated waveforms at the bisector intersection of z=3.6 mm of the half-aperture acoustic plane wave from the right subaperture, the half-aperture acoustic plane wave from the left subaperture, cross-propagating acoustic plane waves from both subapertures of the xAM ultrasound pulse sequence depicted in FIGS. 3A-3C. Particles of the insonified medium along the bisector in FIG. 3C experience the same wave amplitude for pulse (1) and (2), and twice the amplitude for step (3) as shown in FIG. 4. The transmission of the cross-propagation pulse (3) from the two plane waves simultaneously creates double the peak acoustic pressure along the virtual bisector. The cross-propagating plane-wave peak positive pressure is 747 kPa while the residual peak positive pressure is 0.13 kPA, or 0.02% of the cross-propagating plane-wave peak positive pressure.

To show that the xAM technique of certain implementations can provide less distortion than the minimal distortion of an AM technique, the xAM signal cancellation during plane-wave propagation in water (i.e. a weakly nonlinear homogeneous and isotropic medium) was evaluated using two-dimensional time-domain numerical simulations. The directivity of individual elements of the linear transducer array was assessed and set to a maximal angle θ to 21 degrees based on the array −3 dB directivity bandwidth described with respect to FIG. 11. The simulation results are shown in FIG. 4. The cross-propagating plane-wave peak positive pressure is 747 kPa for the simultaneous transmission from both half-apertures while the residue peak positive pressure is 0.13 kPa, or 0.02% of the cross-propagating plane-wave peak positive pressure. The simulation results in FIG. 4 show that for an xAM sequence of a cross-propagation angle θ=18 degrees at a depth of 3.6 mm, the residual peak wave amplitude is reduced by 4 orders of magnitude to 0.02% of the cross-propagating plane-wave peak amplitude (0.13 kPa compared to 747 kPa, respectively). By comparison, a high-end commercial scanner using a typical AM technique can provide a residual on the order of 0.5%.

In various simulation examples described herein, two-dimensional time-domain numerical simulations were performed using k-Wave version 1.2. k-Wave version 1.2 is an open-source acoustics toolbox for MATLAB and C++. A discussion of modeling nonlinear ultrasound propagation in heterogenous media using a k-space pseudospectral method can be found in B. E. Treeby, J. Jaros, A. P. Rendell, and B. T. Cox, "Modeling Nonlinear Ultrasound Propagation in Heterogeneous Media with Power Law Absorption Using a k-space Pseudospectral Method," J. Acoust. Soc. Am. 131, 4324 (2012), which is hereby incorporated by reference in its entirety.

The cumulative nonlinear plane-wave interaction arising during X-wave propagation generally decreases as the cross-prsopagation angle θ increases. However, as the cross-propagation angle θ is increased, the depth of field decreases.

In certain implementations, the depth of field $Z_x$ of an xAM ultrasound pulse sequence can be defined as a finite geometric distance along which the cross-propagating plane waves (also sometimes referred to herein as "X waves") intersect with each other, $$Z_x = \frac{A}{2}\cot\theta \qquad \text{(Eqn. 1)}$$

where A is the full aperture used for the X-wave transmission. For an angle θ=18 degrees and an aperture A=6.5 mm, the $Z_x$ is 10 mm, which is large enough to enable scanning of a full mouse brain. Beyond $Z_x$, images can be reconstructed given the diffraction of the wave-front edges using spherical delay laws analogous to those described in Renaud, G., Bosch, J. G., van der Steen, A. F., and de Jong. N., "Increasing Specificity of Contrast-Enhanced Ultrasound Imaging Using the Interaction of Quasi Counter-Propagating Wavefronts: A Proof of Concept," IEEE Trans. Ultrason. Ferroelectr. Freq. Control 62, 1768 (2015), which is hereby incorporated by reference in its entirety.

B. Nonlinear Interaction of Cross-Wave Accumulating During Plane-Wave Propagation as a Function of Cross Propagation Angle θ Assessed by Simulations The influence of the cross-propagation angle θ on the nonlinear interaction between two non-collinear plane waves emitted by two subapertures in the xAM pulse sequence described with respect to FIG. 3A-3C was also investigated using two-dimensional time-domain numerical k-WAVE simulations. In these simulations, the cross-propagation angle θ (also sometimes referred to as "transmit angle") was varied from 1 to 21 degrees. Transmit delays are calculated to generate a plane wave with the proper angle θ. The simulated wave propagation is in a homogeneous and isotropic medium (water) and is based on the 128 element linear transducer 920 shown in FIGS. 9A, 9B, and 9C. The simulation was also based on a speed of sound in water set to 1480 m/s, an attenuation set to 0.002 dB/MHz$^2$ cm, and a nonlinear parameter of B/A set to 5. The size of the domain was 6.4 mm×8 mm and was discretized with a step size of 10 μm. Perfectly matched layers were used to absorb the waves at the edges of the domain. The source broadcasts a short pulse with a center frequency of 15 MHz. The acoustic pressure generated by the source is varied so that the peak acoustic pressure generated at 4-mm depth by a single aperture equals 400 kPa for all tested angles. For a given transmit angle, three simulations were used: (1) transmission with the right subaperture only, (2) transmission with the left subaperture only, and (3) transmission with both subapertures. The pressure field is recorded along the segment bisector (between the two transmit subapertures). For a given transmit angle, the amplitude modulation scheme is applied to the recorded signals; then, the result was bandpass filtered to reproduce the effect of the limited frequency bandwidth of the transducer with a 100% relative frequency bandwidth (the cutoff frequencies of the filter are 7.5 MHz and 22.5 MHz). The results of these simulations are shown in FIGS. 5A and 5B.

Figure 5A:
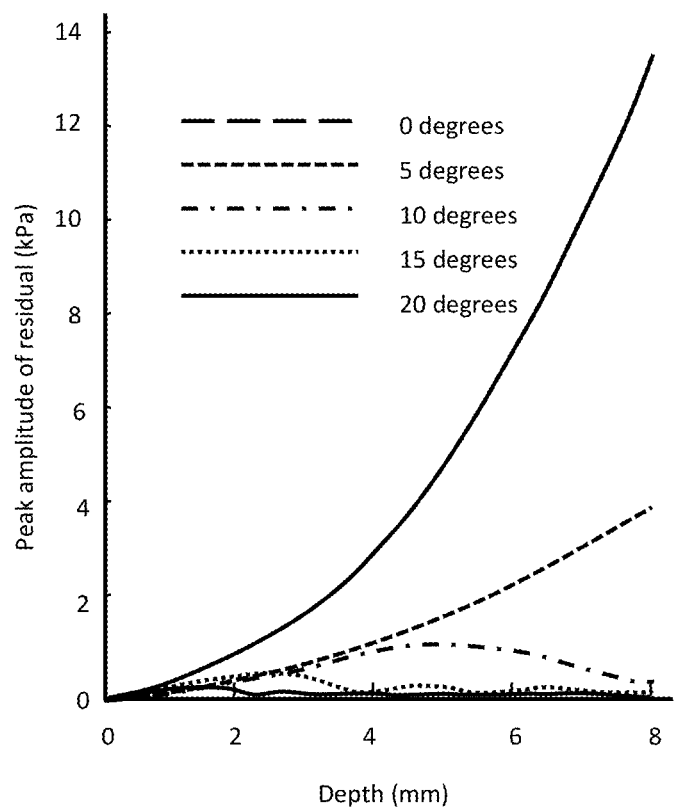
FIG. 5A is a plot of peak positive pressure amplitude of xAM residual as a function of depth for five different cross-propagation angles $\theta$, according to an implementation.
Figure 5B:
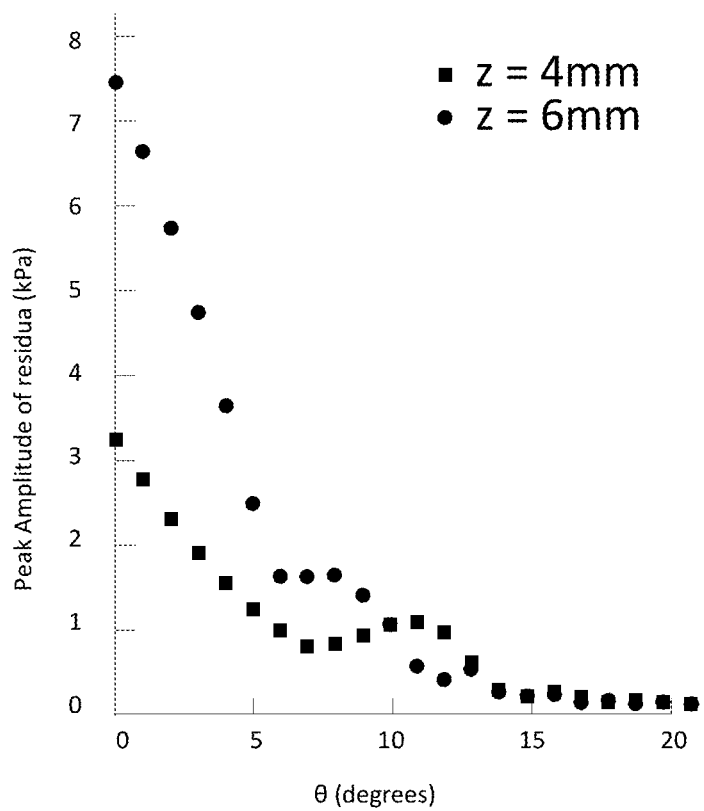
FIG. 5B is a plot of peak positive pressure amplitude of xAM residual as a function of cross-propagation $\theta$, according to an implementation.

FIGS. 5A and 5B illustrate the nonlinear plane-wave interaction as a function of the cross-propagation angle θ based on these k-Wave simulations. FIG. 5A is a plot of the peak positive pressure of the xAM residual as a function of depth for five cross-propagation angles (θ=0 degrees, 5 degrees, 10 degrees, 15 degrees, and 20 degrees). FIG. 5B is a plot of the peak positive pressure of the xAM residual as a function of cross-propagation angle θ from 1 to 21 degrees at depths z=4 mm and z=6 mm. The significance of nonlinear effects accumulating during plane-wave propagation as a function of cross-propagation θ is illustrated in FIGS. 5A and 5B. At low θ angles, at quasi-copropagation (at or about collinear propagation), residual AM nonlinearity accumulates with depth such as shown in FIG. 5A at θ=0 degrees and θ=5 degrees. In particular, for plane-waves propagating in water with a peak amplitude of 400 kPa and at an angle θ=0 degrees (collinear propagation), the residual AM peak amplitude reaches 13.5 kPa at a distance z=8 mm as shown in FIG. 5A. As θ increases, the residual AM nonlinearity is significantly reduced, reaching a noncumulative 0.3 kPa peak pressure at an angle θ=20 degrees as shown in FIG. 5A. FIG. 5B shows the peak amplitude of the AM residue as a function cross-propagation angle θ at the distances z=4 mm and z=6 mm from the transducer array. The simulated data in the plots shown in FIGS. 5A and 5B were obtained using a constant transmit peak pressure at 4 mm equal to 400 kPa. The simulation data shows that the amplitude of the xAM residue drops rapidly as θ increases and converges below a threshold of 0.2 kPa for θ>15 degrees. These results show that a nonlinear planewave interaction becomes less efficient as the θ increases and that in a weakly nonlinear homogeneous and isotropic medium such as water (attenuation equal to 0.002 dB/MHz$^2$ cm), and that in certain implementations, minimal wave distortion due to propagation at cross-propagation angles occurs above 15 degrees.

In some cases, the nonlinear interaction of two noncollinear plane-wave fields of an xAM pulse may result in an asynchronous interaction that generates a sum frequency wave whose amplitude oscillates with a spatial period of 2π/2 k(1−cos θ), with k being the wave vector of the plane waves as discussed in Hamilton, M. F. and TenCate, J. A., "Sum and Difference Frequency Generation Due to Non-collinear Wave Interaction in a Rectangular Duct," J. Acoust. Soc. Am. 81, 1703 (1987) and Hamilton, M. F. and Blackstock, D. T., "On the Coefficient of Nonlinearity β in Nonlinear Acoustics," J. Acoust. Soc. Am. 83, 74 (1988), both of which are hereby incorporated by reference in their entireties. As the angle between the two waves increases, the phase mismatch increases, the spatial period of the nonlinear pressure field decreases, and the nonlinear interaction becomes less efficient. The same phenomenon is observed in the k-Wave simulations discussed above. As the cross-propagation angle θ increases, the spatial period of oscillation and the amplitude of the nonlinear pressure field decrease as shown for example, by the 10-, 15-, and 20-degree lines in FIG. 5A. The nonlinear pressure field may also increase or decrease with the nonlinearity of the medium, as characterized by its shock length.

C. Experimental Reduction of Residual xAM Nonlinearity as a Function of Cross-Propagation Angle (θ)

To experimentally assess the ability of higher-θ xAM pulses to minimize nonlinearity, an xAM imaging sequence and beamforming of an embodiment was implemented on a programmable ultrasound system with a 128-element linear array and the peak residual AM signal of a subwavelength linear scatterer immersed in water was measured. An example of a commercially-available programmable ultrasound system with a 128-element linear array is the Verasonics Vantage ultrasound system with a L22-14v probe sold by Verasonics® of Redmond, Wash., USA. FIGS. 9A-9C and 10 provide a schematic representation of the 128-element linear array and the xAM pulse sequence that were used. The ultrasound acquisition sequence described in Section IV(B) the xAM beam forming described in Section IV(C) were used to generate ultrasound images.

This configuration enables the assessment of the nonlinearity captured by the pulse sequence that is solely due to wave propagation in a typical quasi-incompressible medium (water serves as a first-approximation model for sound-wave propagation in soft biological tissues). A 10 µm diameter nickel wire is placed perpendicular to the imaging plane in phosphate buffer saline (PBS). The nickel wire is positioned at a depth of 4 mm. The wire is imaged using xAM pulse sequences with cross-propagation angle θ values ranging from 1.5 degrees to 21 degrees.

Figure 6A:
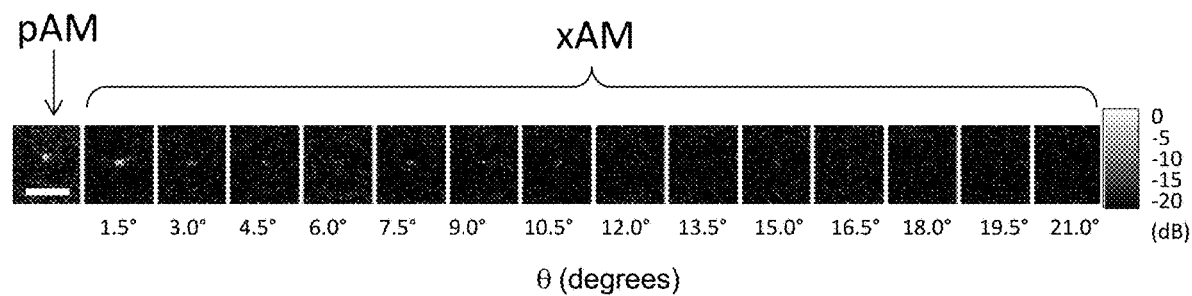
FIG. 6A includes xAM ultrasound cross-sectional images of a subwavelength nickel wire generated using xAM pulse sequences with cross-propagation angles $\theta$ ranging between 1.5 degrees and 21.0 degrees, according to an implementation.
Figure 6B:
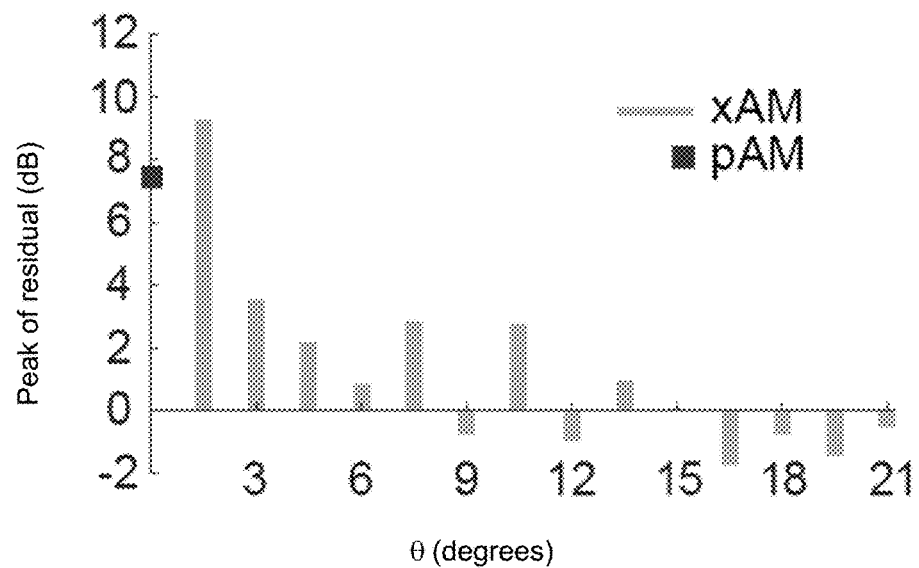
FIG. 6B is a plot of the peak xAM residual signal (dB) and pAM residual signal (dB) for comparison as a function of cross-propagation angle $\theta$, according to an implementation.

FIG. 6A depicts ten xAM cross-sectional (two-dimensional) images of a subwavelength nickel wire generated using xAM pulse sequences with cross-propagation angles θ ranging from 1.5 degrees to 21 degrees according to implementations and one pAM cross-sectional image for comparison. These images were reconstructed from the three component transmissions at cross-propagation angles θ of 1.5 degrees, 3.0 degrees, 4.5 degrees, 6.0 degrees, 7.5 degrees, 9.0 degrees, 10.5 degrees, 12.0 degrees, 13.5 degrees, 15 degrees, 16.5 degrees, 18 degrees, 19.5 degrees, and 21.0 degrees. The wire was positioned at a depth of 4 mm. Each image depth ranges from 3.0 mm to 4.5 mm and each width from −1.5 mm to 1.5 mm. The scale bar for the images as provided in the first image is 1 mm. To compare the xAM results with an AM imaging sequence, a standard parabolic amplitude modulation (pAM) code was implemented, in which half-amplitude transmissions are achieved by silencing the even or odd transmitting elements of the transducer array, and imaging lines are reconstructed along the wave propagation direction. The pAM image is shown in FIG. 6A as the leftmost image. The residual was measured for each angle as the peak value of the beamformed radio-frequency (RF) data. The beamformed radio-frequency (RF) data in FIG. 6B show the same trend predicted by the simulations in Section II(B) above, with residual nonlinearity decreasing sharply with wider angles. FIG. 6B includes a plot of the peak xAM residual signal (dB) and pAM residual signal (dB) for comparison as a function of cross-propagation angle θ, according to an implementation. The peak residual signal (dB) values are peak values of the residual signal relative to the peak value of the noise.

As of the cross-propagation angle θ=3°, the xAM technique significantly outperforms the pAM technique in reducing the residual signal as shown in FIG. 6B. When further comparing the results of the pAM and xAM techniques, the xAM technique is also shown to have higher axial and lateral resolution than the pAM technique. The axial and lateral resolution of the xAM using the full-width half maximum (FWHM) of the point-spread function (PSF) along the respective directions was also measured. The mean axial resolution is 117 µm+16 and the mean lateral resolution is 381 µm+42 with values remaining constant across angles. The axial resolution of the pAM is 103 and the lateral resolution is 250 µm.

Figure 7:
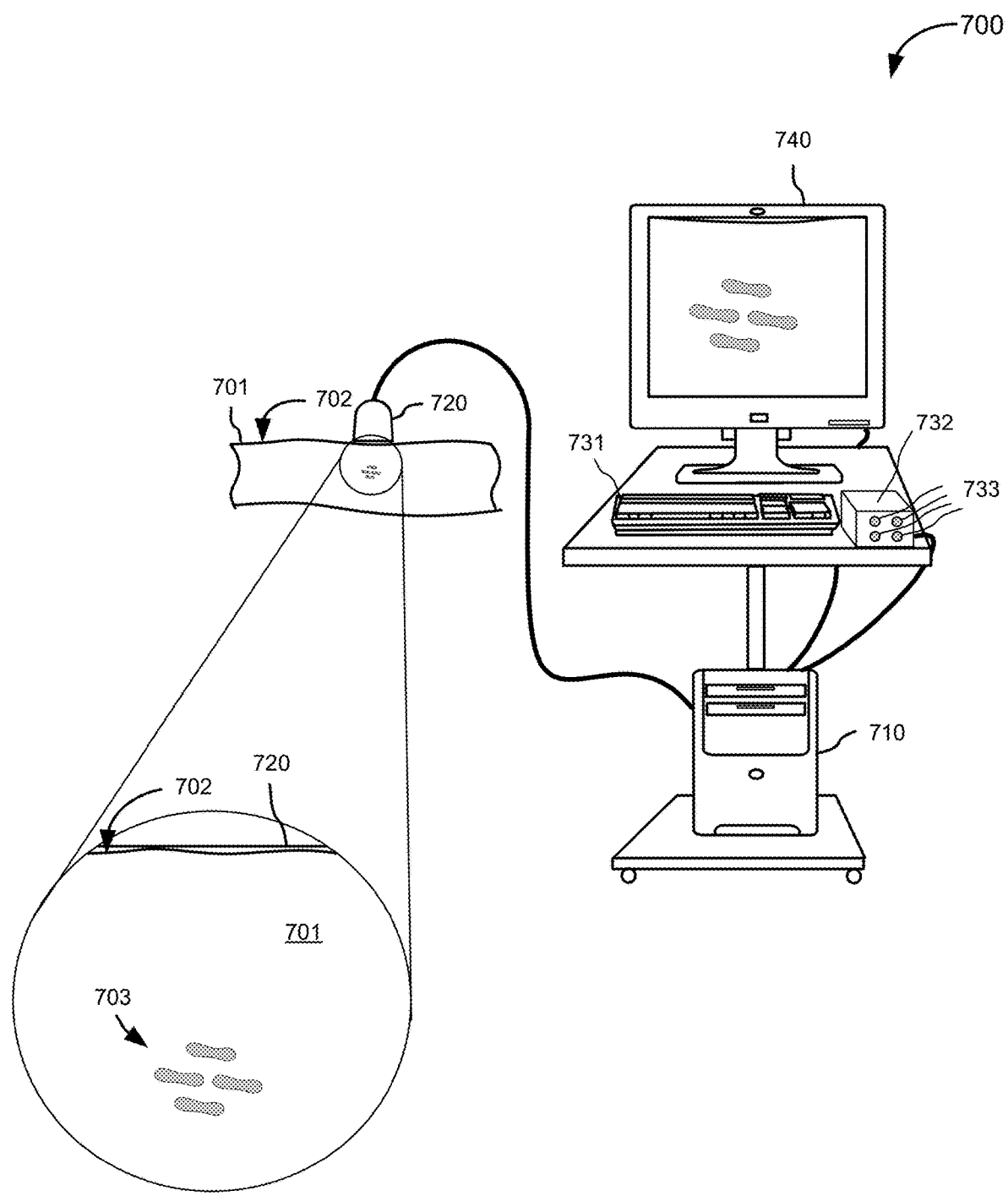
FIG. 7 is a schematic diagram of components of an xAM ultrasound imaging system, according to certain implementations.

III. Examples of Cross-Amplitude Modulation (xAM) Ultrasound Imaging Systems FIG. 7 is a schematic diagram of components of an xAM ultrasound imaging system 700, according to various implementations. The xAM ultrasound imaging system 700 includes a computing device 710 for performing certain operations of an xAM imaging method, an xAM ultrasound transducer probe 720 having one or more transducer arrays 721 for transmitting one or more xAM ultrasound pulse sequences and detecting backscatter echoes, input devices including a keyboard 731 and a tuner 732 with dials 733 for receiving input from the operator, and a display 740. Although the tuner 732 is depicted as a separate standalone device with mechanical dials, the tuner 732 can be an electronic tuner in another implementation, e.g., as part of a touchscreen of the display 740. The computing device 710 is in electrical communication with the ultrasound transducer probe 720, the input devices 731, 732, and the display 740.

The computing device 710 includes one or more processors and an internal memory device (also sometimes referred to herein as computer readable medium (CRM)) in electronic communication with the one or more processors. The one or more processors of the computing device 710 and, additionally or alternatively, other processor(s) of the execute instructions stored on the internal memory device to perform certain operations of an xAM imaging method. The described electrical communications between components of the xAM ultrasound imaging system 700 may be able to provide power and/or communicate data.

For illustration purposes, the xAM ultrasound imaging system 700 is shown with the ultrasound transducer probe 720 touching or coupled via a coupling material (e.g., acoustic gel) to a surface 702 of a specimen 701 with nonlinear scatterers 703 being imaged during an xAM imaging operation. As used herein, a "nonlinear scatterer" generally refers to a feature that scatters a propagating ultrasonic wave such that the detected backscatter echo signal is not a linear transformation, or function of, the ultrasonic wave transmitted from the ultrasound transducer. Some examples of nonlinear scatterers are buckled hGVs and resonant microbubbles. Another example of nonlinear scatterers are cracks in material (e.g., in a bone) or any sub-wavelength gas inclusion.

In various implementations, an xAM ultrasound imaging system includes an ultrasound transducer probe (e.g., ultrasound transducer probe 720 in FIG. 7) having a housing and one or more transducer arrays enclosed within the housing. Generally, the ultrasound transducer probe also includes attachments for coupling the one or more transducer arrays to the housing and connectors for electrically communicating with other system components. As used herein, a "transducer array" generally refers to an array of ultrasonic transducer elements that can transmit acoustic waves in the ultrasonic range (ultrasonic waves). In many implementations, the transducer array is a pulse-echo transducer that can also detect ultrasonic waves. In one aspect, the ultrasonic transducer elements are piezoelectric elements. In another aspect, the ultrasonic transducer elements are complementary metal oxide semiconductor (CMOS) ultrasonic transducer elements. Each ultrasonic transducer element of a transducer array can transmit an ultrasonic wave. Any reflective surfaces and scatterers that lie along the propagation path of an ultrasonic wave cause reflection and scatter. The transducer array converts ultrasonic wave(s) detected at its face into an electrical signal (backscatter echo signal). A commercially-available example of an ultrasound transducer array that can be configured to perform an xAM technique is in the L11-5V probe and the L22-14v probe by Verasonics® located in Redmond, Wash., USA.

In many implementations, a transducer array of an xAM ultrasound imaging system is an analog transducer, which generates electrical signals in response to receiving ultrasonic waves and activates transducer elements by applying a voltage transmission waveform (also referred to herein as voltage transmission pulses) to each transducer element. In these cases, the xAM ultrasound imaging system includes an analog/digital converter that converts the electrical signals into digital data and a digital/analog converter to convert control signals to voltages applied to each of the transducer elements in a time delayed sequence. These converters may be part of the computing device, part of the transducer probe, or may be separate components. In other implementations, the transducer array is a digital transducer array and the analog/digital converter and digital/analog converter can be omitted.

The transducer array can sweep a plurality of xAM pulse sequences to different locations across a field-of-view by activating different sets of transducer elements. In some implementations, the transducer array is a one-dimensional array such as the linear array illustrated in FIGS. 9A-9C and FIG. 10. Backscatter echo data detected by the one-dimensional array can be used to generate a two-dimensional image. Multiple two-dimensional images at different planes can be stacked to form a three-dimensional image. In other implementations, the transducer array is a two-dimensional array of transducer elements. Backscatter echo data detected by a two-dimensional array can be used to generate a three-dimensional (volumetric) image.

Although many implementations describe a transducer array with transducer elements with a centerline of each element in a plane, other implementations have transducer elements lying along a curved surface. For example, a transducer array may be a one-dimensional array along a curve or a two-dimensional array along a single curvature or complex curvature surface. In one implementation, the transducer elements may be in a flexible format that can form to a complex curvature surface. This example implementation may improve the depth of field by reducing the distance between the transducer elements and the intersecting bisector. In this example, a calibration method may be incorporated into the xAM imaging method to adjust the pulses of the xAM pulse sequences to be appropriate to the formed curvature.

In many implementations, an xAM ultrasound imaging system includes a single transducer array. In other implementations, an xAM ultrasound imaging system may have multiple transducer arrays. For example, an xAM ultrasound imaging system may include one or more transducer arrays that transmits xAM pulse sequences and another set of one or more transducer arrays that detect backscatter echo signals. In another example, xAM ultrasound imaging system may include multiple linear transducer arrays that can be separately located along, e.g., a complex curvature surface of the specimen.

Although most implementations described herein pertain to an xAM ultrasound imaging system with a transducer array having transducer elements that both transmit an ultrasound signal and detect backscatter echoes, other implementations may have different configurations. In one implementation, an xAM ultrasound imaging system has one transducer array that transmits the ultrasound signal and a separate transducer array that detects backscatter echoes. In one aspect, the xAM ultrasound imaging system has transducer arrays facing each other. In another implementation, an xAM ultrasound imaging system includes two transducer arrays where one transmits an ultrasound signal and both detect backscatter echoes. For example, a second transducer can be placed close to the first transducer to receive echoes in a similar way. An advantage of having a second receiving transducer (in any geometry) is that it can have a different frequency response and could therefore detect more of the harmonic signals directly. In another implementation, an xAM ultrasound imaging system has two transmitting transducers, one for each of the tilted plane waves, and a third transducer for receiving. This would allow higher angles to be used which could result in a higher reduction in artifact signal.

In some implementations, the xAM ultrasound imaging system also includes one or more input devices that are in communication with the computing device. The operator can use the input devices to adjust imaging parameter(s) used in the xAM method such as one or more of: 1) the frequency of the plane waves of an xAM pulse sequence, 2) the amplitude of the plane waves of an xAM pulse sequence, the threshold value, or the type of nonscattering feature being imaged, 3) the cross-propagation angle of the xAM pulse sequence, 4) the depth of field, 5) the amplitude gain of the display signal, 6) two-dimensional imaging mode or three-dimensional imaging mode, 7) black/white or color imaging mode, 8) the number of cycles in the transmitted waveform, 9) the use of pulse inversion (PI), or a combination of xAM and PI (xAM-PI). For example, in one implementation the operator can use one or more input devices to adjust the propagation angle being used in an xAM ultrasound pulse sequence to reduce artifacts shown in images on the display while maintaining a desired depth of field. As another example, the operator can select a volume to be imaged between two depths, $z_1$ and $z_2$. The volumetric (three-dimensional) image can be determined by digitally subtracting the three-dimensional image data at depth, $z_2$, from the three-dimensional image data at depth, $z_1$. Alternatively, a volumetric image can be determined by stacking multiple two-dimensional images generated at (and in some cases between) the two depths, $z_1$ and $z_2$. Various combinations of operator input may be used to adjust the imaging method generated during a particular ultrasound imaging session. In other implementations described further below, the xAM ultrasound imaging method includes automatic adjustments to imaging parameters.

Returning to FIG. 7 the xAM ultrasound imaging system 700 has input devices including a keyboard 731 and a tuner 732 with two dials 733. In some cases, the dials can be used to adjust imaging parameters. In one implementation, the dials 733 can be used to adjust the peak amplitude of the X waves to generate an acoustic pressure at the bisector intersection over the desired threshold and to also adjust the propagation angle of the X waves of a particular xAM ultrasound pulse sequence. For example, the operator can adjust the peak amplitude to cause an acoustic pressure at the bisector intersection that is known to cause a particular variety of hGVs to buckle and be imaged and then adjust the propagation angle until the artifacts propagated by the nonlinearly scattering hGVs are minimized while maintaining the desired depth of field. These adjustments can be made while viewing the ultrasound images being generated on the display 740.

During an example operation, the computing device sends control signals, converted into a voltage pulse with transmit delays communicated to the ultrasound transducer probe to activate different sets of transducer elements of the transducer array(s) to sweep an xAM pulse sequence to different locations across a field-of-view. The xAM pulse sequence includes transmission of a first ultrasound plane wave (first pulse), transmission of a second ultrasound plane wave (second pulse), and simultaneous transmission of both the first and second noncollinear ultrasound plane waves (third pulse). These pulses can be transmitted in any order. The second ultrasound plane wave is in a direction axisymmetric to the first ultrasound plane wave about a bisector. The first and second ultrasound plane waves are at a cross-propagation angle from the bisector. The simultaneous transmission of both the first and second ultrasound plane waves (third pulse) generates a peak acoustic pressure in the specimen where the first and second ultrasound plane waves intersect at the virtual bisector. An example of a voltage pulse with transmit delays applied to transducer elements of a linear array to generate an xAM pulse sequence is described with reference to FIGS. 9A-9C and FIG. 10. The amplitude of the first and second ultrasound plane waves is defined so that when transmitted individually the peak acoustic pressure is below a threshold, e.g., a buckling threshold, a collapse threshold, or a cavitation threshold, and when transmitted simultaneously the peak acoustic pressure at the bisector is above the threshold. The ultrasound transducer converts the ultrasonic waves from backscatter echoes detected at its face into backscatter echo signals. The computing device digitally sums the echo signals from the two plane-wave transmissions and then digitally subtracts them from the echo signals of the X-wave transmissions. In this way, the nonzero differential nonlinear scattering signal is solely retrieved, while the echo signal of surrounding linear scatterers cancel. The computing device combines the image data for all the locations across the field-of-view to generate an ultrasound image of the nonlinear scatterers.

Figure 8:
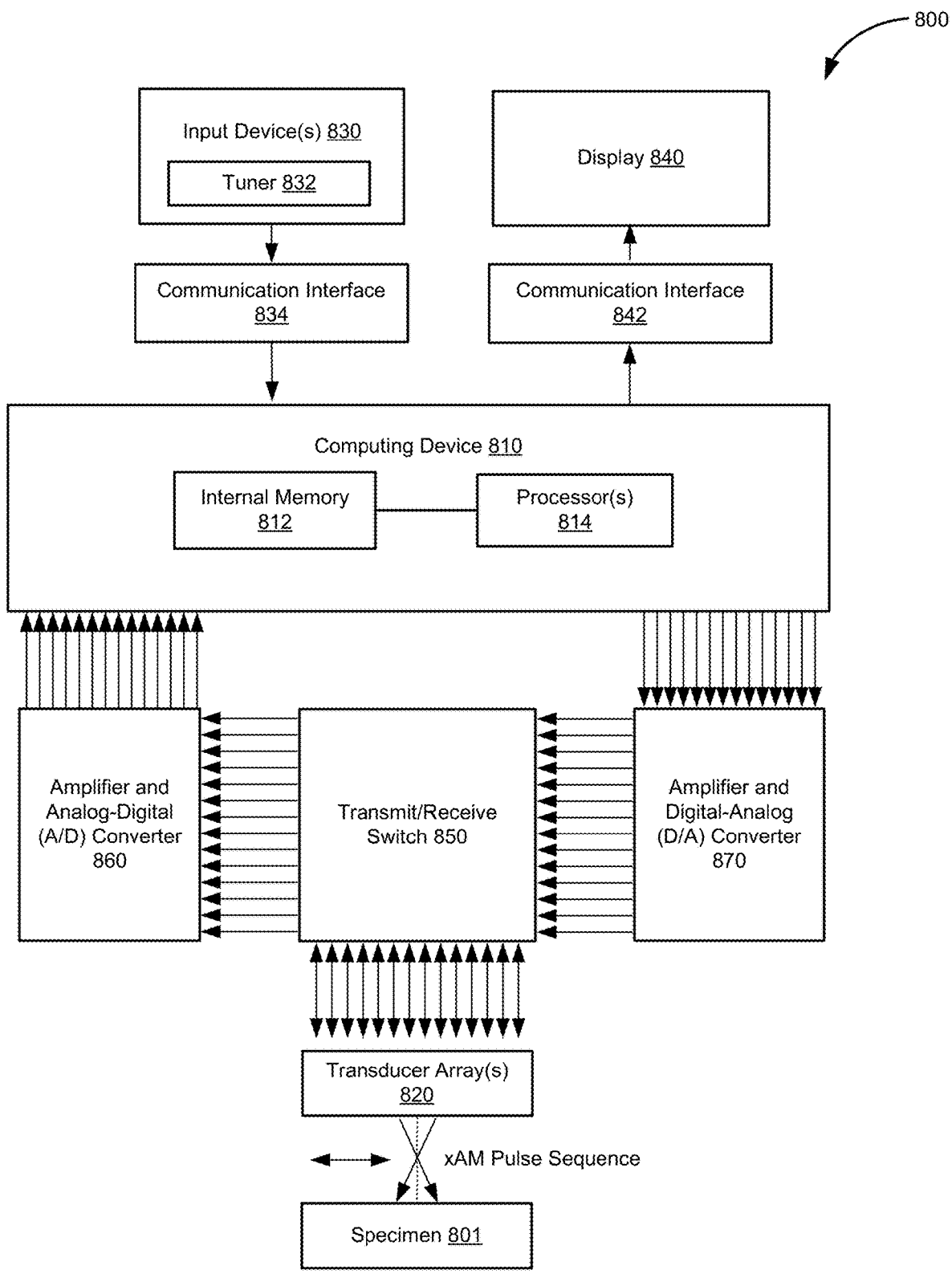
FIG. 8 is a simplified block diagram of components of an xAM ultrasound imaging system, according to various implementations.

FIG. 8 illustrates a simplified block diagram of components of an xAM ultrasound imaging system 800, according to certain implementations. Some of the components of xAM ultrasound imaging system 800 are similar in function to components of xAM ultrasound imaging system 700 in FIG. 7. The xAM ultrasound imaging system 800 includes a computing device 810 with one or more processors 814 and an internal memory device 812 in electrical communication with the one or more processors 814. The xAM ultrasound imaging system 800 also includes one or more transducer arrays 820 for transmitting one or more xAM ultrasound pulse sequences and detecting backscatter echoes. The xAM ultrasound imaging system 800 also includes a transmit/receive switch 850, an amplifier and analog-digital converter 860, and an amplifier and digital-analog converter 870. In another implementation, one or more of the amplifiers and converters may be omitted.

Returning to FIG. 8, the transmit/receive switch 850 is in electronic communication with the one or more transducer arrays 820, the amplifier and an analog/digital converter 860, and the amplifier and digital/analog converter 870. In one implementation, the amplifier and analog/digital converter 860 includes multiple amplifiers. For example, the system may include a total gain amplifier for amplifying the signal from the transducer array(s) 820, an amplifier for amplifying the signal from the first set of transducer elements and an amplifier for amplifying the signal from the second set of transducer elements.

The xAM ultrasound imaging system 800 also includes one or more input devices 830 including a tuner 832 and a communication interface 834 in communication with the input device(s) 830. The xAM ultrasound imaging system 800 also includes a communication interface 842 and a display 840 in communication with the communication interface 842. The computing device 810 is also in communication with the communication interface 834 and the communication interface 842. For illustration purposes, the xAM ultrasound imaging system 800 is depicted as sweeping (denoted by double arrow) an xAM pulse sequence across a field-of-view of a specimen 801 during an xAM imaging operation. The described electrical communications between components of the xAM ultrasound imaging system 800 may be able to provide power and/or communicate data.

In certain implementations, the xAM ultrasound imaging system includes a transmit/receive switch that controls the delivery of the voltage pulse with time delays to the transducer elements of the transducer array and the receiving of electrical signals with backscatter echo data received from each transducer elements. The transmit/receive switch can isolate the transmitting circuitry from the receiving circuitry. A commercially-available transmit/receive switch is one of the Ultrasound T/R Switch ICs by Microchip Technology of Mansfield, Tex. For example, the xAM ultrasound imaging system 800 in FIG. 8 includes the transmit/receive switch 850 that can switch between: (i) receiving electrical signal(s) with backscatter echo data from the one or more transducer arrays 820, and (ii) sending a voltage pulse with time delays to the transducer elements of the transducer array(s) 820. In implementations that do not include the switch, the voltage signals used to excite the transducer elements cause a ringdown signal to be appended to the start of the received signal. In this case, the ringdown signal is removed during beamforming.

The computing device 810 is configured or configurable by an operator, e.g., based on input from the input device(s) 830, to display input data or raw or processed image data over the communication interface 842 for display on the display 840. The computing device 810 is also configured or configurable by an operator, e.g., based on input from the input device(s) 830, to send control signals to the amplifier and digital-analog converter 870. The amplifier and digital/analog converter 870 can convert the control signals to a voltage pulse with time delays transmitted via the transmit/receive switch 850 to the transducer elements of the one or more transducer arrays 820 to activate the transducer elements to generate the xAM pulse and detect backscatter echoes. An example of a voltage pulse with time delays used to generate an xAM ultrasound pulse sequence is described with respect to FIGS. 9A-9C and 10. The ultrasonic waves detected by the transducer array(s) 820 generate electrical signals, which are communicated to the amplifier and analog/digital converter 860. The amplifier and analog/digital converter 860 amplifies and converts the electrical signals to digital backscatter echo data communicated to the computing device 810. The computing device 810 is also configured or configurable to digitally sum the backscatter echo data from the two plane-wave transmissions and digitally subtract the sum from the backscatter echo data of the X-wave transmissions to determine backscatter echo data from the nonlinear scatterers and then combine for all the xAM pulse sequences swept over the field-of-view to generate an ultrasound image of the nonlinear scatters.

In various implementations described herein, the computing device of the xAM ultrasound imaging system includes one or more processor(s). These processor(s) may be, for example, one or more of a general purpose processor (CPU), an application-specific integrated circuit, an programmable logic device (PLD) such as a field-programmable gate array (FPGA), or a System-on-Chip (SoC) that includes one or more of a CPU, application-specific integrated circuit, PLD as well as a memory and various interfaces. In FIG. 8, the one or more processor(s) 814 of the computing device 810 and, additionally or alternatively, other processor(s) of the xAM ultrasound imaging system 800 execute instructions stored on a computer readable medium (e.g., the internal memory 812 or external memory) to perform operations of the xAM ultrasound imaging system 800. For example, the one or more processor(s) 814 of the computing device 810 may communicate control signals to the digital/analog converter 870 which are converted to a voltage pulse with time delays (also sometimes referred to herein as "voltage transmission pulses") to activate the transducer elements of the one or more transducer array(s) 820 to transmit xAM pulse sequences during an imaging operation. The one or more processor(s) 814 of the computing device 810 may also perform operations of an xAM imaging method to process the backscatter echo data to generate ultrasound images of nonlinear scatterers. Examples of xAM imaging methods are described in detail with respect to FIGS. 12 and 13.

In various implementations described herein, the computing device includes an internal memory device. The internal memory device may include a non-volatile memory array for storing processor-executable code (or "instructions") that is retrieved by the processor(s) to perform various functions or operations described herein for carrying out various logic or other operations on the backscatter echo signals or image data. The internal memory device also can store raw backscatter echo data and/or processed image data. In some implementations, the internal memory device or a separate memory device can additionally or alternatively include a volatile memory array for temporarily storing code to be executed as well as image data to be processed, stored, or displayed. In some implementations, the computing device itself can include volatile and in some instances also non-volatile memory.

The xAM ultrasound imaging system 800 further includes a communication interface 842 and a display 840 in communication with the communication interface 842. The computing device 810 is configured or configurable to communicate data over the communication interface 842 for display on the display 840 including, e.g., input data for the pulses of the xAM pulse sequences, raw backscatter echo data, and processed image data. The xAM ultrasound imaging system 800 also includes a communication interface 834 in communication with the input device(s) 830 for receiving input from an operator of the xAM ultrasound imaging system 800.

In some implementations, the xAM ultrasound imaging system further includes one or more additional interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that the various system components can be electrically coupled to communicate with the computing device over one or more of a variety of suitable interfaces and cables such as, for example, USB interfaces and cables, ribbon cables, Ethernet cables, among other suitable interfaces and cables.

The data signals output by one or more transducer array(s) may in some implementations be mutliplexed, serialized or otherwise combined by a multiplexer, serializer or other electrical component of the xAM ultrasound imaging system before being communicated to the computing device. In certain implementations, the computing device can further include a demultiplexer, deserializer or other device or component for separating the backscatter echo data, e.g., separating backscatter echo data for xAM sequences for one propagation angle from backscatter echo data for xAM sequences from another propagation angle in a coherent compounding implementation so that the image frames for each propagation angle can be processed in parallel by the computing device.

The input device(s) 830 are in electrical communication with the computing device 810 through the communication interface 834 to be able to send a signal with imaging parameters to the computing device 810 based on input received at the input device(s) 830. The input device(s) 830 includes a tuner 832. In some cases, the tuner 832 is a separate component that includes various types control mechanisms such as dials, switches, knobs, buttons, sliding bars, etc. In another case, the tuner 832 is an electronic tuner with graphical user interfaces, e.g., on a touchscreen of the display 840.

Although many of the components of xAM ultrasound imaging systems illustrated herein are shown in electronic communication with each other via wiring, it would be understood that the electronic communication between components described herein can be in wired or wireless form.

Figure 10:
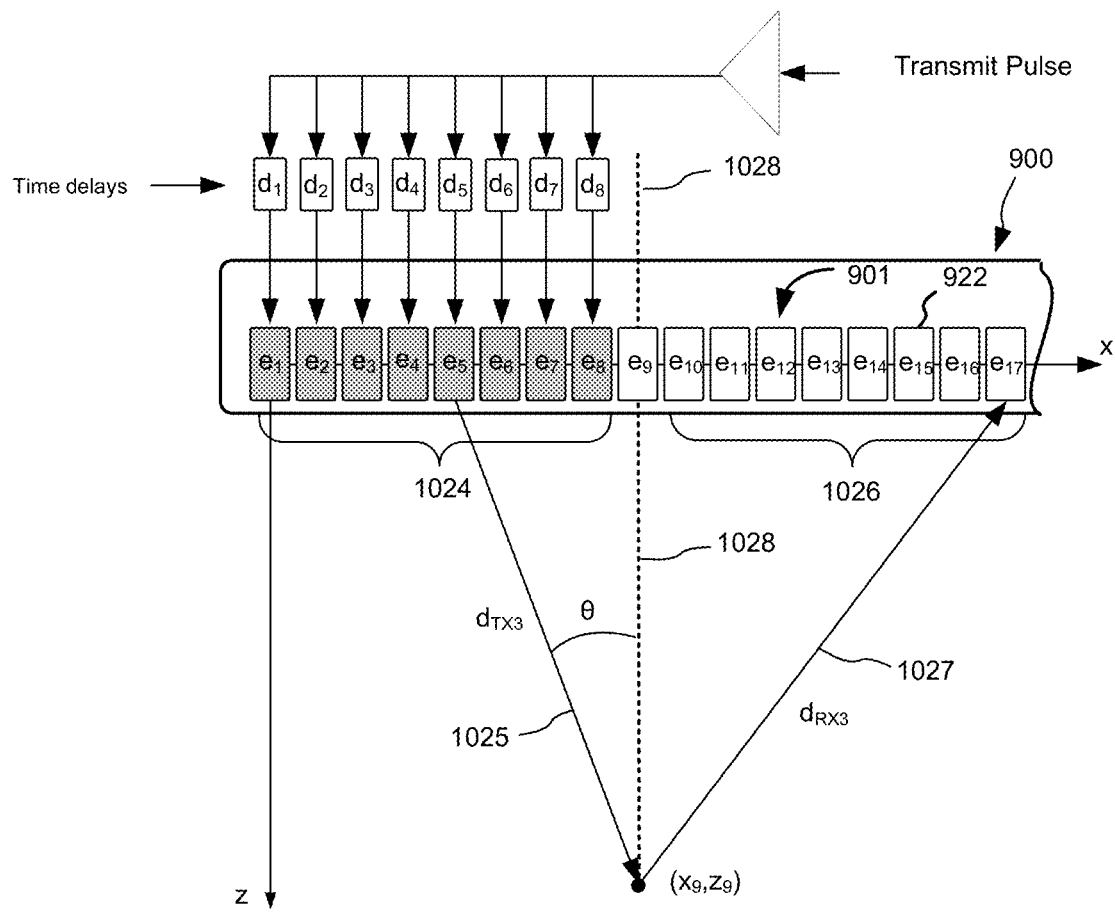
FIG. 10 is a cross-sectional drawing of another portion of the ultrasound transducer probe in FIG. 9A depicting voltage pulse and time delays applied to the transducer elements of the left subaperture to direct the transmission of the first ultrasound plane wave, according to an implementation.

FIGS. 9A, 9B, and 9C each include a cross-sectional drawing of a portion of an ultrasound transducer probe 900 with a narrow-strip acoustic linear transducer array 901, according to an embodiment. The transducer array 901 includes one hundred twenty eight (128) transducer elements 922. A commercially-available example of a narrow-strip acoustic linear transducer array is in the L11-5V probe and the L22-14v probe by Verasonics® located in Redmond, Wash., USA. FIG. 10 is cross-sectional drawing depicting another portion of the ultrasound transducer probe 900. The narrow-strip acoustic linear transducer array 901 has a uniform pitch, p, between transducer elements 922. The linear transducer array 901 includes an x-axis through the center of the transducer elements, a z-axis originating from the first element, $e_1$, of the linear transducer array 901, and a y-axis (not shown) perpendicular to the x-axis and the z-axis.

In FIGS. 9A, 9B, and 9C respectively, the linear transducer array 901 is depicted during transmission of three pulses of an exemplary xAM pulse sequence. The linear transducer array 901 includes an aperture of N transducer elements that are active during the xAM pulse sequence. The aperture includes a first element, $e_1$, and an $n^{th}$ element, $e_N$, which is an arbitrary element in the linear transducer array 901. The aperture includes a left subaperture 924 with a first set of transducer elements, $e_1$-$e_{b-1}$, and a right subaperture 926 with a second set of transducer elements, $e_{b+1}$-$e_N$. The linear transducer array 901 includes a virtual bisector 928 between the right subaperture 926 and the left subaperture 924. The transducer element $e_b$, lying along the virtual bisector 928 between the two subapertures 924, 926 is silent (inactive) during the xAM pulse sequence. In the illustrated example, the cross-propagation angle, θ, is the angle between the plane waves and the x-axis and also between the plane waves and the virtual bisector 928.

The exemplary xAM pulse sequence involves: (i) activating the first set of transducer elements of the left subaperture 924; (ii) activating the second set of transducer elements of the right subaperture 926; and (iii) simultaneously activating the first and second sets of transducer elements of the left and right sub-apertures 924, 926. The pulses of this sequence can occur in any order. The xAM imaging method sequentially implements different windows of active transducer elements 922 in the acoustic linear transducer array 901 to sweep xAM pulse sequences across the field-of-view. For example, one aperture of active transducer elements could include a first set of transducer elements, $e_1$-$e_8$, and a second set of transducer elements, $e_{10}$-$e_{17}$, another aperture of active transducer elements could include a third set of transducer elements, $e_2$-$e_9$, and a fourth set of transducer elements, $e_{11}$-$e_{18}$, and yet another aperture of active transducer elements could include a fifth set of transducer elements, $e_3$-$e_{10}$, and a sixth set of transducer elements, $e_{12}$-$e_{19}$, and so forth.

FIG. 9A depicts the active transducer elements of the left sub-aperture 924 of the linear transducer array 901 during operation (i) that transmits a tilted plane wave in a direction that is at cross-propagation angle, θ, from the x-axis and the virtual bisector 928. The illustrated example shows a distance $d_{TX1}$ from the planer wavefront to a point $(x_b, z_b)$ along the virtual bisector 928 and a return distance $d_{RX1}$ to the array 901. FIG. 9B depicts the active transducer elements of the right sub-aperture 926 of the linear transducer array 901 during operation (ii) that transmits a tilted plane wave in a direction that is at cross-propagation angle, θ, from the x-axis and the virtual bisector 928. The distance from the planer wavefront to a point $(x_b, z_b)$ along the virtual bisector 928 is $d_{RX2}$ and the distance to the array 901 is $d_{RX2}$. FIG. 9C depicts the active transducer elements of both the left sub-aperture 924 and the right sub-aperture 926 of the linear transducer array 901 during operations (i) and (ii) that simultaneously transmit both plane waves. Additional discussion configuration and directivity of a narrow-strip acoustic linear transducer array such as the narrow-strip acoustic linear transducer array 901 described with respect to FIGS. 9A-9C can be found in Selfridge, A., Kino, G., and Khuri-Yakub, B., "A Theory for the Radiation Pattern of a Narrow-Strip Acoustic Transducer," Appl. Phys. Lett. 37, 35 (1980), which is hereby incorporated by reference in its entirety.

FIG. 10 depicts the voltage pulse with time (transmit) delays applied to the transducer elements of the left subaperture to direct the plane wave at the cross-propagation angle, according to an embodiment. In FIG. 10, the linear transducer array 901 includes an aperture of sixteen (16) transducer elements 922 ($e_1$-$e_8$ and $e_{10}$-$e_{17}$) that are active during an xAM pulse sequence. The aperture includes a left subaperture 1024 with a first set of transducer elements, $e_1$-$e_8$, and a right subaperture 1026 with a second set of transducer elements, $e_{10}$-$e_{17}$. The linear transducer array 901 also includes a virtual bisector 1028 between the right subaperture 1026 and the left subaperture 1024. The transducer element $e_9$, lying along the virtual bisector 1028 between the two subapertures 1024, 1026 is silent (inactive) during the xAM pulse sequence. In the illustrated example, the cross-propagation angle, θ, is the angle between the plane waves and the x-axis and also between the plane waves and the virtual bisector 1028. The illustrated example shows a distance $d_{TX2}$ from the planer wavefront to a point $(x_9, z_9)$ along the virtual bisector 1028 and a return distance $d_{RX2}$ to the array 901. For illustrative purposes, FIG. 10 also depicts the electrical transmission pulse and time delays ($d_1$, $d_2$, $d_3$, $d_4$, $d_5$, $d_6$, $d_7$, and $d_8$) used to apply the voltage transmission waveform to each of the transducer elements 922 of the left subaperture 1024. The time-delayed activation of the transducer elements 922 causes the generation of a tilted plane wave in a direction that is at cross-propagation angle θ from the x-axis and the virtual bisector 1028.

Figure 11:
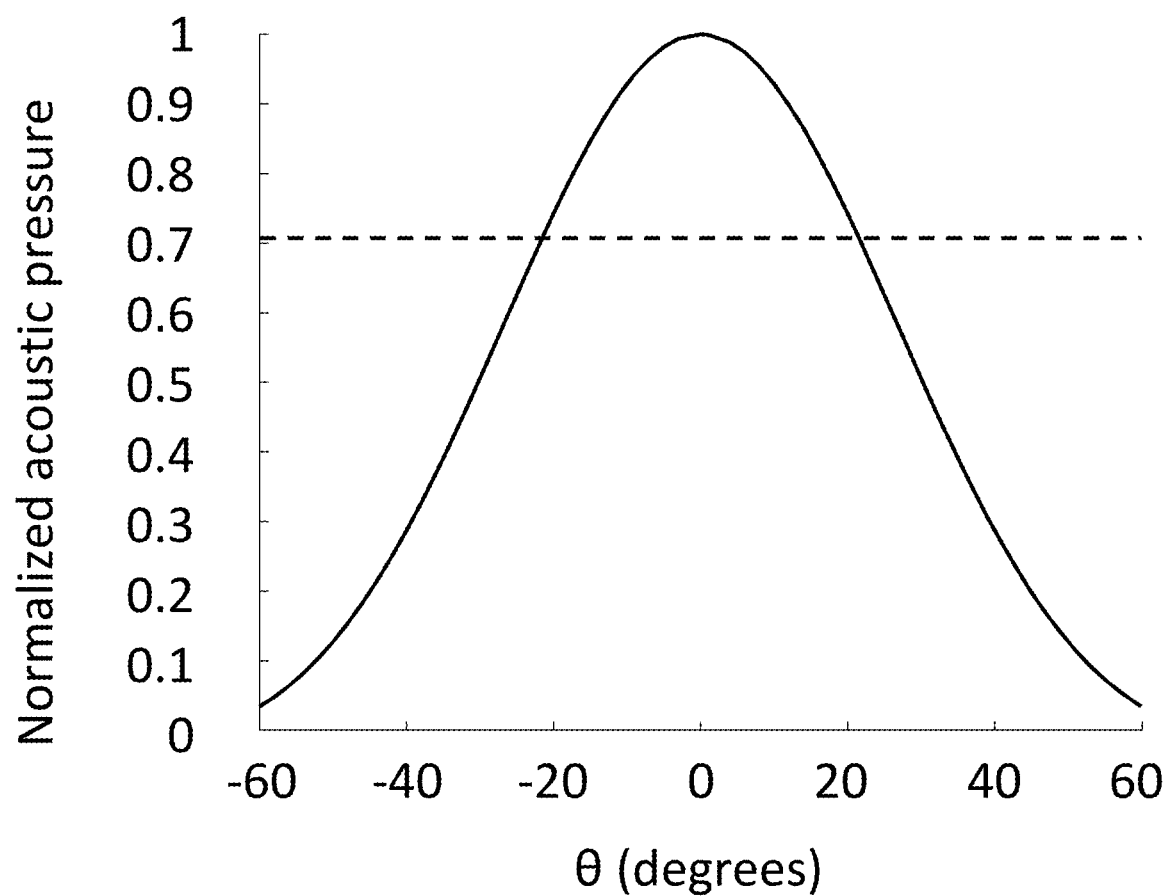
FIG. 11 is a plot of normalized acoustic pressure of one transducer element of a linear transducer array over different angles to illustrate directivity, according to an implementation.

FIG. 11 depicts a plot of normalized acoustic pressure of one transducer element of the linear transducer array of FIGS. 9A-9C and 10 over different angles, according to an embodiment. The plotted data illustrates the directivity of an individual element of the linear transducer array. The linear transducer array has a pitch, p, of 0.1 mm and frequency of 15.6 Mhz. The dotted line indicates a −3 dB acoustic pressure level. As shown, the transducer element has a −3 dB directivity bandwidth with a maximum propagation angle θ of approximately 21 degrees.

In various implementations, an xAM imaging method uses one or more xAM pulse sequences where the cross-propagation angle or angles used are greater than 15 degrees. In certain implementations, an xAM imaging method uses one or more xAM pulse sequences with cross-propagation angle(s) in a range between about 15 degrees and about 21 degrees. In a coherent compounding implementation, for example, a plurality of xAM pulse sequences having cross-propagation angles that have values within a range between about 15 degrees and about 21 degrees are used. In another implementation, one xAM pulse sequence is used where the cross-propagation angle implemented is in a range between about 15 degrees and about 21 degrees. In other implementations, an xAM imaging method uses one or more pulse sequences having cross-propagation angle(s) in a range between about 18 degrees and about 21 degrees. In one implementation, an xAM imaging method uses one or more pulse sequences with cross-propagation angle(s) greater than 15 degrees. In one implementation, an xAM imaging method sweeps one or more pulse sequences having a cross-propagation angle(s) of about 21 degrees. In an implementation using three transducers, angles in a range between about 21 to 90 degrees could be used to further reduce artifacts. For deep imaging with a single transducer, angles in a range between about 5 to 15 degrees could be used to achieve some artifact reduction.

The transducer frequencies used to transmit xAM pulse sequences vary depending on implementation. In some cases, the frequency of the transducer elements is adjusted during an imaging process, either automatically or by an operator, to modify the image being generated. Some examples of suitable frequency ranges include 1 MHz-50 MHz. In one example, the transducer array is an 18 Mhz linear transducer array. In another example, the transducer array is a 15.6 Mhz linear transducer array. In other implementations, the transducer array has a frequency ranging from 4 to 11 MHz.

In certain implementations, the amplitude of the cross-propagating plane waves used in the xAM pulse sequences is determined by the nonlinear properties of the nonlinear scatterers being imaged. For example, in various implementations, the amplitude of each of the plane waves in an xAM pulse sequence is set to half the threshold value, typically the buckling threshold of certain scatterers within the specimen so as to cause buckling from the peak acoustic pressure at the bisector intersection from cross-propagating X-waves. The amplitude of the voltages applied to the transducer elements relates to the amplitude of the cross-propagating plane waves.

Figure 25:
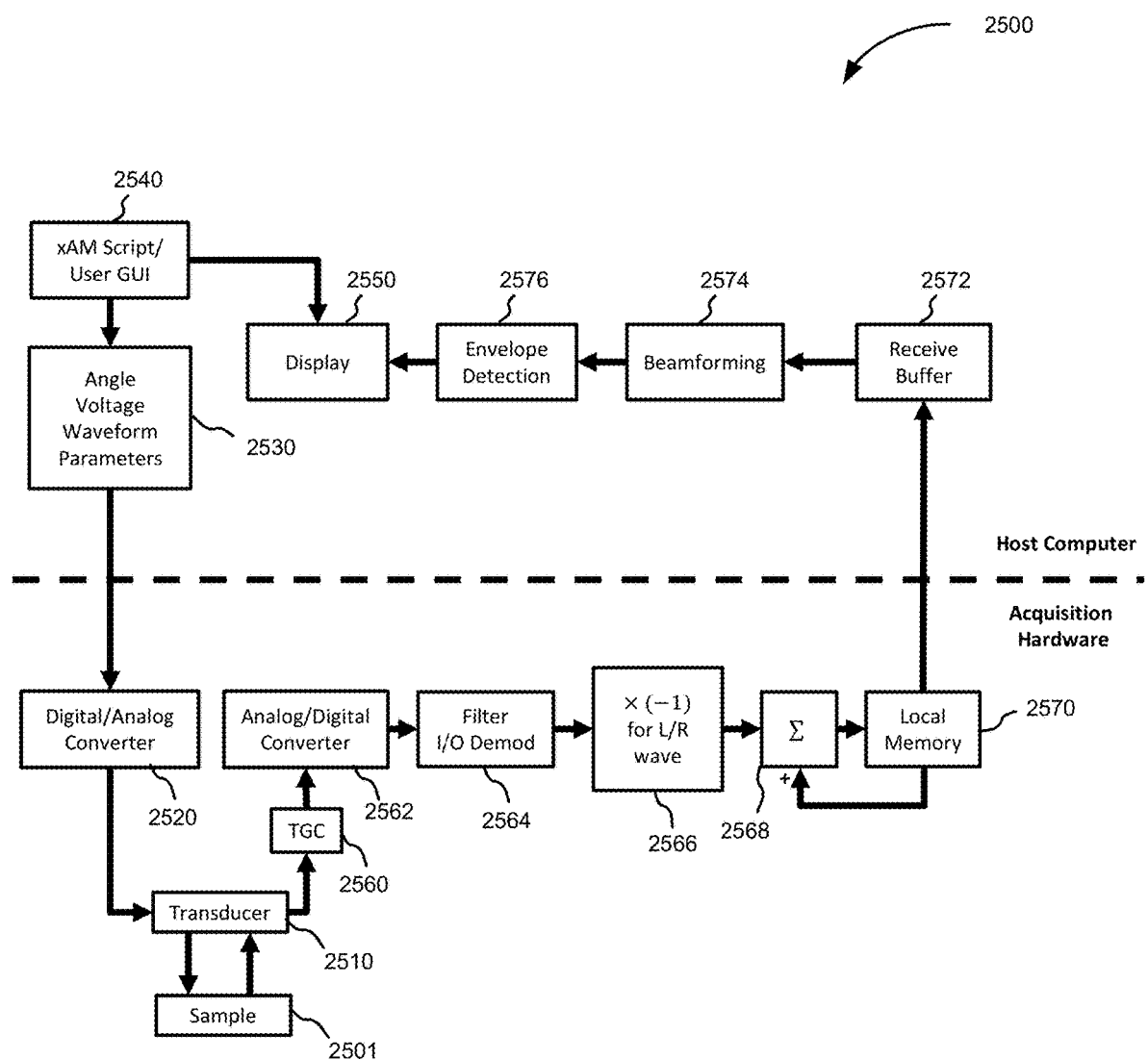
FIG. 25 a schematic diagram of components of an xAM ultrasound imaging system, according to certain implementations.

FIG. 25 a schematic diagram of components of an xAM ultrasound imaging system 2500, according to certain implementations. Some of the components of xAM ultrasound imaging system 2500 are similar in function to components of xAM ultrasound imaging system 700 in FIG. 7 and xAM ultrasound imaging system 800 in FIG. 8.

The xAM ultrasound imaging system 2500 includes a transducer 2510 (also referred to herein as a "transducer probe") having one or more transducer arrays. For illustrative purposes, the transducer 2510 is shown during operation transmitting xAM ultrasound pulse sequence(s) and detecting backscatter echoes from a sample 2501. The xAM ultrasound imaging system 2500 also includes a first digital/analog converter 2520 in communication with the transducer 2510, which receives signals specifying the angle, voltage, waveform, and other parameters 2530 that are communicated to the first digital/analog converter 2520 to determine the transmitted waveform, and an xAM script/user graphical user interface (GUI) 2540. The xAM script 2540 is in the form of instructions including imaging parameters that may be input in some cases by an operator via a graphical user interface of an input device. The xAM script 2540 specifies the angle, voltage, waveform, and other transmit parameters 2530 that are communicated to the first digital/analog converter 2520, which generates voltage pulses sent to the individual transducer elements of the transducer array(s) of the transducer 2510. The xAM ultrasound imaging system 2500 also includes a display 2550. As shown, the display 2550 can also receive data from the xAM script/user GUI 2540 for display.

The xAM ultrasound imaging system 2500 also includes a time-gain compensation (TGC) amplifier 2560 in communication with the transducer 2510, a second analog/digital converter 2562 in communication with the TGC amplifier 2560, a filter and I/O demodulator 2564 connected to the second analog/digital converter 2562, a phase inversion operation 2566 for inverting the sign of the digital signals received from the left and right sub-aperture transmits in communication with the filter and I/O demodulator 2564, an accumulator 2568 for summing the inverted left and right sub-aperture signals with the full-aperture signal, local memory 2570 in communication with the accumulator 2568, a receiving buffer 2572 connected to the local memory 2570, a beamformer 2574 connected to the receiving buffer 2572, and an envelope detection module 2576 connected to the beamformer 2574.

The TGC amplifier 2560 is in communication with the transducer 2510 to receive backscatter echo signals. The output of the TGC amplifier 2560 is received at the second analog/digital converter 2562. The output of the second analog/digital converter 2562 is received at and filtered and demodulated down to baseband signals by the filter and I/O demodulator 2564. The output of the filter and I/O demodulator 2564 is received at the phase inversion operation 2566 where the sign of the left and right sub-aperture signals is inverted for subtraction from the full-aperture signal. The output of phase inversion operation 2566 is received at the accumulator 2568. The accumulator 2568 stores and retrieves the signals from each of the pulses of an xAM sequence to subtract the sum of the L/R sub-aperture pulses from the full aperture pulses. The resulting data is communicated to the receiving buffer 2572. The output of the receiving buffer 2572 is received at the beamformer 2574 for beamforming. An example of a beamforming technique is found in Section IV(C). The output of beamformer 2574 is received at the envelope detection module 2576 for envelope detection. The display 2550 is also connected to the envelope detection module 2576 to receive the ultrasound image and display parameters from the GUI.

In one implementation, the xAM ultrasound imaging system 2500 may also include a switch between the transducer 2510 and the digital/analog converter 2520 and the time-gain compensation (TGC) amplifier 2560 to switch between communicating backscatter echo signals to the time-gain compensation (TGC) amplifier 2560 and receiving voltage signals to excite the transducer elements communicated from the digital/analog converter 2520. In implementations that do not include the switch, the voltage signals used to excite the transducer elements cause a ringdown signal to be appended to the start of the received signal. In this case, the ringdown signal is removed during beamforming.

IV. Cross-Amplitude Modulation (xAM) Ultrasound Imaging Methods

A. Example of an xAM Method

Figure 12:
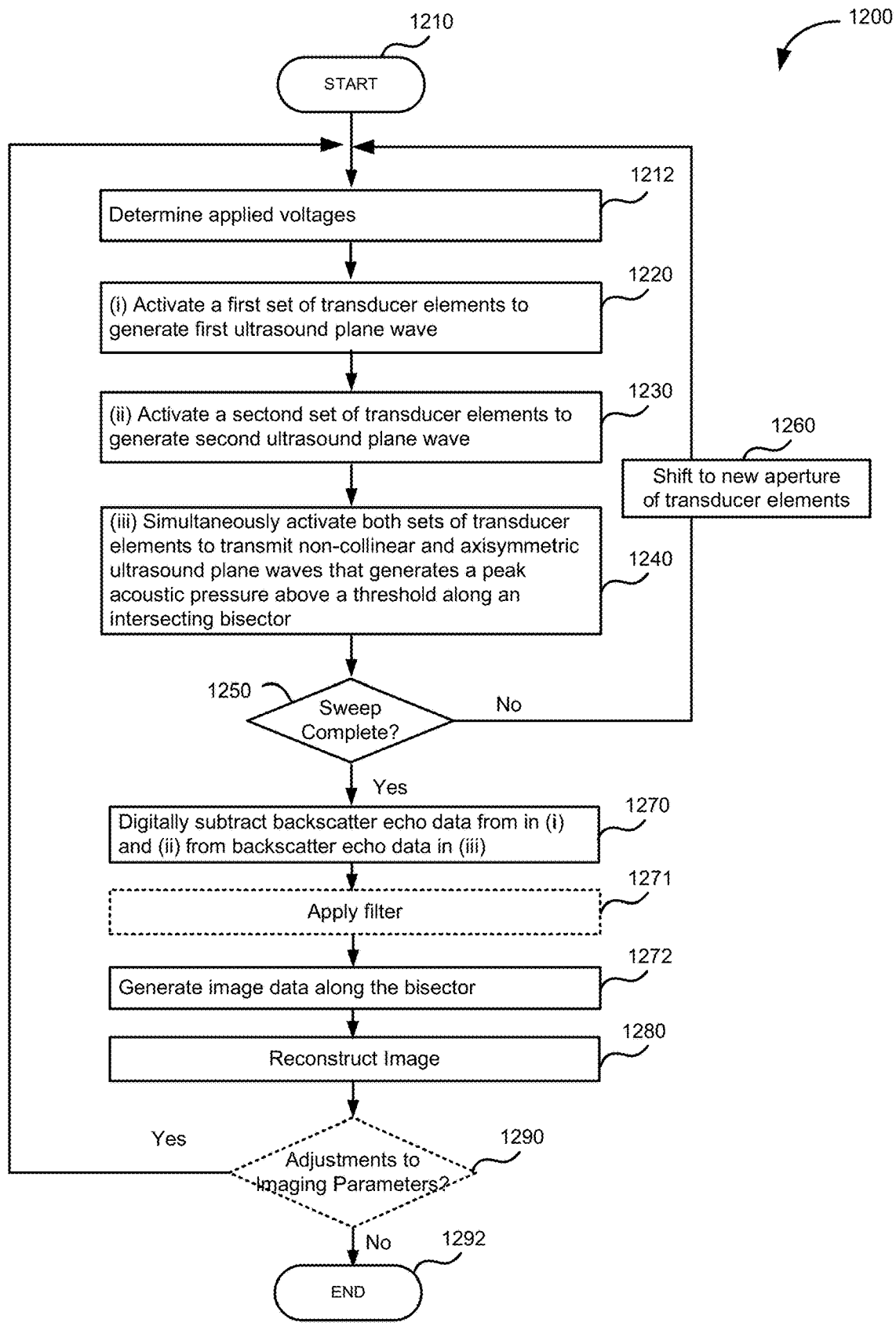
FIG. 12 is a flowchart depicting operations of an xAM ultrasound imaging method, according to various implementations.

FIG. 12 includes a flowchart 1200 depicting operations of an xAM ultrasound imaging method, according to various implementations. The operations are performed by one or more components of an xAM ultrasound imaging system such as system 700 of FIG. 7 or system 800 of FIG. 8. One or more of the operations may be performed by executing instructions retrieved from memory.

At operation 1210, the xAM ultrasound imaging method starts. The imaging parameters being used in the first xAM ultrasound pulse sequence are initialized based on imaging parameters retrieved from memory or communicated from an input device(s). The initial imaging parameters may be default parameters, imaging parameters input from the operator, or a combination thereof. Some examples of imaging parameters include, e.g., amplitude and frequency of the plane waves, cross-propagation angle(s), depth of field, depths of two-dimensional slices being imaged, desired field-of-view, minimum resolution, type or types of nonlinear scatterers being imaged, threshold value (e.g., critical buckling, cavitation, or collapse threshold values) of nonlinear scatterers being imaged, a desired peak acoustic pressure at the bisector, etc.

At operation 1212, the xAM imaging method determines an applied voltage with transmit delays to apply to sets of transducer elements of the one or more transducer arrays to cause transmission of the xAM pulse sequence for the current imaging parameters. For example, the xAM imaging method may determine that the amplitude of the applied voltage is half the buckling threshold of the type of nonlinear scatterers being imaged. As another example, the xAM imaging method may determine an applied voltage and transmit delays that generate plane waves at the desired cross-propagation angle such as depicted in FIG. 10. In some implementations, the xAM imaging method uses a table, e.g., a lookup table, with applied voltages and transmit delays for transducer elements that corresponds to one or more combinations of imaging parameters. For example, a table may include an applied voltage with time delays for one propagation angle or associated depth of field for the xAM imaging system being used. In many implementations, the amplitude of the voltage pulse applied to the first set and second set of transducer elements is selected so as when transmitted separately cause a peak acoustic pressure below a threshold value and when transmitted simultaneously cause a peak acoustic pressure above the threshold value along the intersecting bisector.

Once the applied voltage for each of the transducer elements is determined at operation 1212, the xAM imaging method sends control signal(s) with applied voltages and transmit delays to the transducer elements of the one or more transducer arrays to transmit the xAM pulse sequence at operations 1220, 1230, and 1240. Operations 1220, 1230, and 1240 can be applied in any order.

At operation 1220, the control signals apply a voltage pulse to each of the first set of transducer elements. The applied voltages activate the first set of transducer elements causing the transmission of a first ultrasound plane wave at a cross-propagation angle. For example, the transducer array may include an aperture of N transducer elements that are active during the xAM pulse sequence. The aperture includes a first subaperture with a first set of transducer elements, a second subaperture with a second set of transducer elements, and a virtual bisector between the subapertures. In this case, voltages are applied with time delays to the transducer elements of the first subaperture to transmit the first ultrasound plane wave at the cross-propagation angle from the virtual bisector between the sub-apertures.

At operation 1230, the control signals apply a voltage to each of the second set of transducer elements. The applied voltages activate the second set of transducer elements to cause the transmission of a second ultrasound plane wave. The first and second ultrasound plane waves are noncollinear and axisymmetric about the virtual bisector. Returning to the example above, the control signals apply voltages with time delays are applied to the transducer elements of the second subaperture to transmit the second ultrasound plane wave at the cross-propagation angle from the bisector.

At operation 1240, control signals apply a voltage to each transducer element of the first set and second set of transducer elements. The applied voltages activate the first and second sets of transducer elements to cause the simultaneous transmission of the first and second ultrasound plane waves. The first and second ultrasound plane waves intersect at the virtual bisector and cause a combined peak acoustic pressure above the threshold value along the intersecting bisector.

In pulse-echo implementations, the one or more ultrasound transducer arrays detect ultrasonic waves from linear and nonlinear scattering from the xAM pulse sequence and generate backscatter echo signals, which are either communicated to the computing device or stored to memory. The backscatter echo signals are received directly from the one or more transducer arrays or retrieved from memory. Generally, the backscatter echo signals from the ultrasound transducer array are in the form of radio frequency (RF) signals. In some cases, the backscatter echo signals are amplified by an amplifier, e.g., through linear amplification.

At operation 1250, it is determined whether the desired number of xAM pulse sequences for the sweeping the desired field-of-view has been completed. If the required number of xAM pulse sequences has been completed, the xAM imaging method continues to operation 1270.

If the required number of xAM pulse sequences has not been completed, the xAM imaging method shifts to a new aperture of active transducer elements of the one or more transducer arrays (operation 1260). For example, if the linear array shown in FIGS. 9A, 9B, and 9C were implemented, the xAM imaging method may involve an aperture of active transducer elements including a first set of transducer elements, $e_1$-$e_8$ and a second set of transducer elements, $e_{10}$-$e_{17}$. Next, the xAM imaging method can shift to a new aperture of active transducer elements including a third set of transducer elements, $e_2$-$e_9$ and a fourth set of transducer elements, $e_{11}$-$e_{18}$. In the next operation, the xAM imaging method can shift to a new aperture of active transducer elements including a fifth set of transducer elements, $e_3$-$e_{10}$, and a sixth set of transducer elements, $e_{12}$-$e_{19}$, and so forth.

In one implementation, the xAM imaging method also determines the number of sweeping operations for the xAM pulse sequence based on a desired field-of-view or a maximum field-of-view of the transducer array. For example, the transducer array may have a maximum field-of-view based on the length of the transducer array. The number of sweeping operations for the field-of-view can be determined, e.g., based on the number of transducer elements in the transducer array and/or based on the desired resolution for the ultrasound image.

At operation 1270, for each xAM pulse sequence, the backscatter echo signal from transmission of the plane waves in operations 1220 and 1230 is digitally subtracted from the backscatter echo signal from the simultaneous transmission of both plane waves in operation 1240. In this operation, the linear scattering measured in response to each of the plane waves transmitted individually is subtracted from the scattering measured in response to the simultaneous transmission of both plane waves to determine the backscatter echo signal from nonlinear scattering at the virtual bisector. This digital subtraction is performed for each of the xAM pulse sequences to determine backscatter echo signal from nonlinear scattering at different locations of the virtual bisector over the desired field-of-view.

In many implementations, the xAM imaging system operates in pulse-echo mode where the same transducer array sends the xAM pulse sequence and receives backscatter echo signals from the specimen. The xAM imaging method involves sweeping the xAM pulse sequence to different virtual bisector locations across the field-of-view. The time domain backscatter echo signals provide the depth locations of the scatterers. The amplitudes of the backscatter echo signals generally represent the strength of the scatterers, which is related to acoustic properties. At operation 1270, the xAM imaging method digitally subtracts the backscatter echo signals for each of the xAM pulses to determine the amplitudes of the backscatter echo signals from nonlinear scattering along each bisector.

At optional (denoted by dotted line) operation 1271, the xAM method may apply a filter (e.g., a narrow band filter) to successive frames of backscatter echo signal from the digital subtraction employed in operation 1270. If applied, filtering of the backscatter echo signals along each bisector line is performed and the mean signal intensity for each depth, z, based on analysis frequency is determined. Applying a filter to successive frames during live imaging can reduce noise while saving system memory. An example of a filter is a first-order infinite impulse response (IIR) filter, which can be applied to successive frames of radio frequency (RF) backscatter echo data, according to the following difference equation:

$$y[n]=\alpha y[n-1]+(1-\alpha)x[n], \quad \text{(Eqn. 2)}$$

where n is the frame index, $\alpha$ is the persistence coefficient, x is the unfiltered RF backscatter echo data, and y is the output of the filter.

At operation 1272, the xAM imaging method processes the backscatter echo signal for nonlinear scattering to generate image data along the bisector of each xAM sequence employed. As mentioned above, the backscatter echo signals from the ultrasound transducer array are generally in the form of radio frequency (RF) signals. In some cases, the backscatter echo signals are amplified by an amplifier, e.g., through linear amplification. Various methods can be used to process the backscatter echo signals to generate image data. In many implementations, at operation 1272 the xAM method also determines an envelope of the backscatter echo signals, e.g., by making a Hilbert transform of each of the backscatter echo signals.

In one implementation, the peak amplitude of the backscatter echo signal at a particular depth corresponds to an intensity value of a pixel of image data at the same depth along the bisector. For example, a pixel at $(x_1, z_1)$ location can be assigned the intensity value corresponding to the peak amplitude of the backscatter echo signal at a depth of $z=z_1$ and along the bisector at $x=x_1$.

In one implementation, using the same transducer, system gain and signal processing settings of the imaging parameters, backscatter echo signals are acquired from a reference phantom whose backscattering and attenuation properties are known.

Returning to FIG. 12, at operation 1280, the ultrasound image of the nonlinear scatterers is reconstructed from the backscatter echo data for the nonlinear scattering in operation 1270 for different virtual bisectors over the field-of-view. Image reconstruction includes applying xAM beamforming to the backscatter echo signal for nonlinear scattering from operation 1272. An example of details of image reconstruction and dynamic focusing is discussed in xAM beamforming Section IV(C) below.

In some implementations, the xAM system implements a single linear array which sweeps xAM pulse sequences across the desired field-of-view. Each xAM pulse sequence includes a pulse with simultaneous transmission of two plane waves that generates a peak acoustic pressure above a threshold along a bisector line. In these implementations, a two-dimensional ultrasound image can by generated by collecting the subtracted backscatter echo signals at each of the virtual line bisectors. A three-dimensional volumetric ultrasound image can be generated by stacking a set of these two-dimensional images.

In other implementations, the xAM system implements a two-dimensional array or a multitude of linear arrays which sweep xAM pulse sequences across the desired field-of-view. Each xAM pulse sequence includes a pulse with simultaneous transmission of two plane waves that generates a peak acoustic pressure above a threshold along different bisector planes. The backscatter echo data from the two-dimensional array or multiple linear arrays can be used to reconstruct a three-dimensional image.

In certain implementations, the xAM system includes two-dimensional arrays instead of one-dimensional arrays. In these cases, tilted plane waves that cross-propagate and intersect along a plane rather than a line are transmitted. With this approach, a two-dimensional xAM image can be obtained from a single three pulse xAM transmission. A volumetric xAM image can be obtained from multiple three pulse xAM transmissions. In one implementation, the frame rate implemented is in the range of 0.5 kHz to 30 kHz. An example of ultrafast ultrasound imaging is described in Provost, J., Papadacci, C., Arango, J. E., Imbault, M, Fink, M, Gennisson, J. L., Tanter, M., Pernot, M., "3D ultrafast ultrasound imaging in vivo," Physics in Medicine & Biology. 2014 Sep. 10; 59(19):L1, which is hereby incorporated by reference in its entirety.

Returning to FIG. 7, optionally (denoted by dashed line), it is determined whether there are adjustments to the imaging parameters (operation 1290). The adjustments may be from autofocusing feedback or from operator input. If there are adjustments, the xAM imaging method continues to operation 1212 and the xAM method determines the voltage transmission waveforms based on the new imaging parameters. If there are no adjustments, the xAM imaging method continues to operation 1292 and the xAM method ends.

B. Ultrasound Acquisition Sequences of Certain xAM and pAM Imaging Examples

Certain images discussed herein were acquired by employing pulse sequences implemented on a programmable Verasonics Vantage® ultrasound system with a L22-14v probe sold by Verasonics Inc. of Redmond, Wash., USA. For example, the fourteen xAM images and the one pAM image in FIG. 15 were acquired by employing pulse sequences on the programmable Verasonics Vantage ultrasound system. The transducer probe of the Verasonics Vantage ultrasound system is a linear array of one hundred twenty eight (128) transducer elements with a 0.10-mm pitch, an 8-mm elevation focus, a 1.5-mm elevation aperture, and a center frequency of 18.5 MHz with 67%–6 dB bandwidth. A single-cycle transmit waveform at 15.625 MHz was applied to each active array element to ensure the fundamental frequency is divided 4 times with the 62.5-MHz sampling rate of the system.

To provide a tradeoff between lateral field-of-view and the axial depth of field, an aperture of sixty five (65) elements for the xAM pulse sequence (with the center element silenced to allow for a symmetric code). This aperture provides for sixty four (64) ray lines per xAM image. That is, the xAM imaging method can shift an aperture of sixty five (65) elements to 64 locations of the transducer array to generate 64 ray lines.

On the other hand, the focus of the parabola used in the pAM sequence is set to 8 mm to match the probe's elevation focus. An aperture of 38 elements was used for the pAM sequence to maintain an f-number of 2, and the number of ray lines to 64 was limited to match the xAM frames. To control for variation in pressure across different beam profiles, we select probe voltages were selected for each xAM cross-propagation angle and for pAM that generate a CTR of 10 dB in the hGV inclusion of the phantoms.

Figure 13:
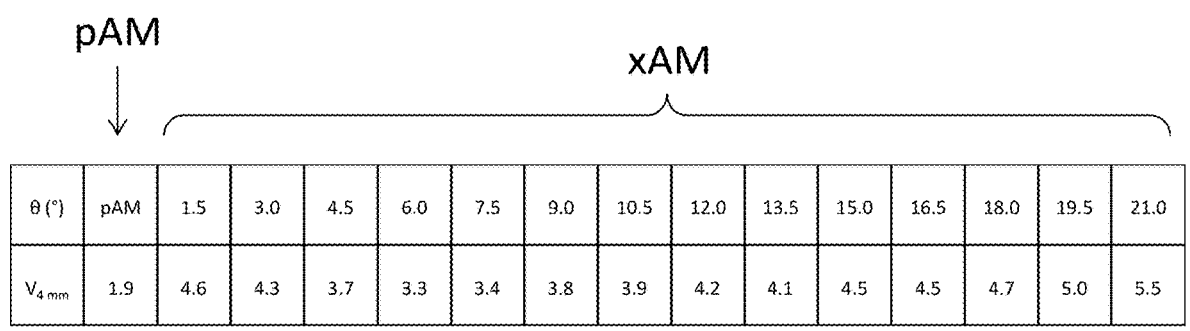
FIG. 13 is a voltage-pressure table of input transducer voltages for transducer elements of a linear transducer array, according to an implementation.

FIG. 13 is a voltage-pressure table listing the input transducer voltages for application to the transducer elements of a linear transducer array (e.g., array 922 in FIGS. 9A-9C) for generating a peak acoustic pressure of 10-dB CTR at a depth of field of 4 mm for different cross-propagation angles for xAM technique. This allows for 10 dB CTR across images to enable comparison of the artifact intensity across cross-propagation angles. For example, the phantom images shown in FIG. 15 were acquired using the voltages in the illustrated voltage-pressure table. The table also includes an input transducer voltage for a pAM technique.

Raw radio frequency (RF) backscatter data was collected and implemented in a custom real-time image reconstruction pipeline, including a beamforming algorithm (described in Section IV(C) below) suited to the unique requirements of xAM technique. To reduce noise during live imaging while saving system memory, a first-order infinite impulse response (IIR) filter was applied to successive frames of RF backscatter echo data, according to the following difference equation:

$$y[n]=\alpha y[n-1]+(1-\alpha)x[n], \qquad \text{(Eqn. 2)}$$

where n is the frame index, $\alpha$ is the persistence coefficient, x is the unfiltered RF backscatter echo data, and y is the output of the filter. All backscatter echo data reported are acquired with $\alpha=0.9$ except for the in vivo pAM image, which is acquired with $\alpha=0.7$ to avoid blurring due to motion.

C. xAM Beamforming

In certain implementations, the xAM method implements a beamforming method for image reconstruction that accounts for xAM image lines that are not formed along the propagation direction of the ultrasonic waves, but instead along the line (or plane) on which the two cross-propagating plane waves intersect. The linear array transmission configuration and directivity is modeled based on the linear array aperture geometry and directivity described with reference to FIGS. 9A-9C and FIG. 10. Although the beamforming method is described below with respect to a one-dimensional linear array, the method can be extrapolated to a two-dimensional planar array, and to curved arrays.

The distance from either angled wavefront to the point ($x_b$, z) and the return trip distance of the echo received by array element $e_n$ are, respectively, $$Zd_{TX}(\theta, x_b, z) = (x_b - x_1) p \sin\theta + z \cos\theta \quad \text{(Eqn. 3)}$$

$$Zd_{RX}(x_b, x_n, z) = \sqrt{(x_n - x_b)^2 p^2 + z^2} \quad \text{(Eqn. 4)}$$

Hence, the two-way travel time to element $e_b$ is:

$$\tau_T/R \to x_n = \frac{1}{c}[(x_b - x_1) p\sin\theta + z\cos\theta] + \frac{1}{c}\sqrt{(x_n - x_b)^2 p^2 + z^2} \quad \text{(Eqn. 5)}$$

whereas the observed arrival time of this echo on the bisector element is:

$$\tau_T/R \to x_b = \frac{1}{c}[(x_b - x_1) p\sin\theta + z\cos\theta + z] \quad \text{(Eqn. 6)}$$

The depth of the echo signal can be derived from its arrival time on the bisector as:

$$z = \frac{c\tau_T/R \to x_b - (x_b - x_1) p\sin\theta}{\cos\theta + 1} \quad \text{(Eqn. 7)}$$

and, finally, the time delay to apply to the received signal for dynamic focusing can be obtained:

$$\delta(x_n, z) = \frac{\tau_T}{R} \to x_n - \tau_T/R \to x_b = \frac{1}{c}\left[\sqrt{(x_n - x_b)^2 p^2 + z^2} - z\right] \quad \text{(Eqn. 8)}$$

These beamforming equations (Eqns. 3-8) are valid in the region over which the waves are cross propagating. Based on Eqn 1, the depth of field $Z_x$ to which this region extends is given by $(x_n - x_b)\cot\theta$.

D. xAM Method with Coherent Compounding

In some implementations, an xAM method includes coherent compounding of the RF backscatter echo data from multiple xAM pulse acquisitions with different cross-propagation angles, θ. A comparison of images acquired using an xAM method with data acquisitions using a single cross-propagation angle or with coherent compounding of data acquisitions with four different propagation angles is discussed in the Section IV(D)(1) below. In some cases, coherent compounding of xAM data acquired at different angles may increase CTR and CAR. An example of Coherent Plane-Wave compounding used with ultrasonography can be found in Montaldo, G., Tanter, M., Bercoff, J Benech, N., and Fink, M., "Coherent Plane-Wave Compounding for Very High Frame Rate Ultrasonography and Transient Elastography," IEEE Trans. Ultrason. Ferroelectr. Freq. Control 56, 489 (2009).

Figure 14:
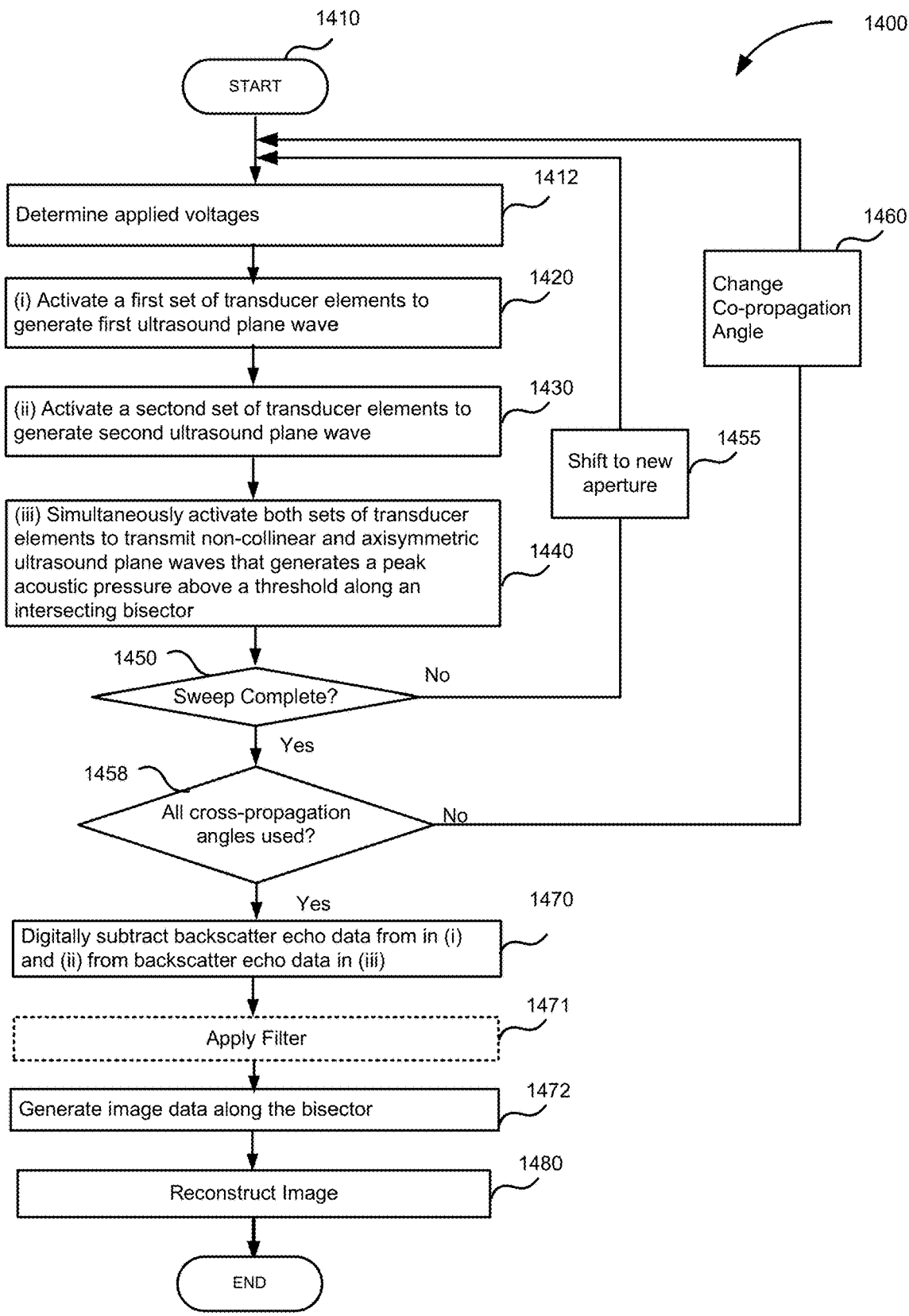
FIG. 14 is a flowchart depicting operations of an xAM ultrasound imaging method with coherent compounding, according to various implementations.

FIG. 14 includes a flowchart 1400 depicting operations of an xAM ultrasound imaging method with coherent compounding, according to various implementations. The operations are performed by one or more components of an xAM ultrasound imaging system such as system 700 of FIG. 7 or system 800 of FIG. 8. One or more of the operations may be performed by executing instructions retrieved from memory.

At operation 1410, the xAM ultrasound imaging method starts. In this operation, the plurality of cross-propagation angles being used in coherent compounding is determined. In addition, the cross-propagation angle for the first xAM ultrasound pulse sequence is initialized to one of the plurality of the cross-propagation angles. The plurality of cross-propagation angles and/or initial cross-propagation angle may be default values, input from the operator, or a combination thereof.

At operation 1412, the xAM imaging method determines an applied voltages (also referred to herein as voltage transmission waveforms or pulses) for each of the transducer elements of the one or more transducer arrays to cause transmission of the xAM pulse sequence for the imaging parameters. For example, the xAM imaging method may determine that the amplitude of the applied voltage is half the buckling threshold of the type of nonlinear scatterers being imaged. As another example, the xAM imaging method may determine an applied voltage and time delays that generate plane waves at the desired cross-propagation angle such as depicted in FIG. 10. In some implementations, the xAM imaging method uses a lookup table or other database table with applied voltages for transducer elements for one or more combinations of imaging parameters. For example, a table may include an applied voltage with time delays for one propagation angle or associated depth of field for the xAM imaging system being used.

Once the voltages for each of the transducer elements is determined at operation 1412, the xAM imaging method sends control signal(s) with applied voltages to the transducer elements of the one or more transducer arrays to transmit the xAM pulse sequence at operations 1420, 1420, and 1440. Operations 1420, 1420, and 1440 can be applied in any order.

At operation 1420, the control signals apply a voltage to each of the first set of transducer elements. The applied voltages activate the first set of transducer elements causing the transmission of a first ultrasound plane wave at a cross-propagation angle. For example, the transducer array may include an aperture of N transducer elements that are active during the xAM pulse sequence. The aperture includes a first subaperture with a first set of transducer elements, a second subaperture with a second set of transducer elements, and a virtual bisector between the subapertures. In this case, voltages are applied with time delays to the transducer elements of the first subaperture to transmit the first ultrasound plane wave at the cross-propagation angle from the virtual bisector between the sub-apertures.

At operation 1430, the control signals apply a voltage to each of the second set of transducer elements. The applied voltages activate the second set of transducer elements to cause the transmission of a second ultrasound plane wave. The first and second ultrasound plane waves are noncollinear and axisymmetric about the virtual bisector. Returning to the example above, the control signals apply voltages with time delays are applied to the transducer elements of the second subaperture to transmit the second ultrasound plane wave at the cross-propagation angle from the bisector.

At operation 1440, control signals apply a voltage to each transducer element of the first set and second set of transducer elements. The applied voltages activate the first and second sets of transducer elements to cause the simultaneous transmission of the first and second ultrasound plane waves. The first and second ultrasound plane waves intersect at the virtual bisector and cause a combined peak acoustic pressure above the threshold value along the intersecting bisector.

At operation 1450, it is determined whether the desired number of xAM pulse sequences for the sweeping the desired field-of-view has been completed. If the required number of xAM pulse sequences has been completed, the xAM imaging method continues to operation 1458.

If the required number of xAM pulse sequences has not been completed, the xAM imaging method shifts to a new aperture of active transducer elements of the one or more transducer arrays (operation 1455). For example, if the linear array shown in FIGS. 9A, 9B, and 9C were implemented, the xAM imaging method may involve an aperture of active transducer elements including a first set of transducer elements, $e_1$-$e_8$ and a second set of transducer elements. Next, the xAM imaging method can shift to a new aperture of active transducer elements including a third set of transducer elements, $e_2$-$e_9$ and a fourth set of transducer elements, $e_{11}$-$e_{18}$. In the next operation, the xAM imaging method can shift to a new aperture of active transducer elements including a fifth set of transducer elements, $e_3$-$e_{10}$, and a sixth set of transducer elements, $e_{12}$-$e_{19}$, and so forth. In one implementation, the xAM imaging method also determines the number of sweeping operations for the xAM pulse sequence based on a desired field-of-view or the maximum field-of-view of the transducer array.

At operation 1458, it is determined whether all the propagation angles in the plurality of cross-propagation angles of coherent compounding have been used. If all have not been used, the xAM imaging method changes the co-propagation angle to another one in the plurality of cross-propagation angles and loops back to determine the voltage transmission waveforms in operation 1412. If all have been used, the xAM imaging method continues to operation 1462.

At operation 1470, for each xAM pulse sequence, the backscatter echo signal from transmission of the plane waves in operations 1420 and 1430 is digitally subtracted from the backscatter echo signal from the simultaneous transmission of both plane waves in operation 1440. In this operation, the linear scattering measured in response to each of the plane waves transmitted individually is subtracted from the scattering measured in response to the simultaneous transmission of both plane waves to determine the backscatter echo signal from nonlinear scattering at the virtual bisector. This digital subtraction is performed for each of the xAM pulse sequences to determine backscatter echo signal from nonlinear scattering at different locations of the virtual bisector over the desired field-of-view.

In some implementations, the xAM method further includes applying a filter (e.g., a narrow band filter) to successive frames of backscatter echo signal from the digital subtraction employed in operation 1470.

At optional (denoted by dotted line) operation 1471, the xAM method may apply a filter (e.g., a narrow band filter) to successive frames of backscatter echo signal from the digital subtraction employed in operation 1470. If applied, filtering of the backscatter echo signals along each bisector line is performed and the mean signal intensity for each depth, z, based on analysis frequency is determined. Applying a filter to successive frames during live imaging can reduce noise while saving system memory. An example of a filter is a first-order infinite impulse response (IIR) filter, which can be applied to successive frames of radio frequency (RF) backscatter echo data, according to the following difference equation:

$$y[n]=\alpha y[n-1]+(1-\alpha)x[n], \quad \text{(Eqn. 2)}$$

where n is the frame index, $\alpha$ is the persistence coefficient, x is the unfiltered RF backscatter echo data, and y is the output of the filter.

At operation 1472, the xAM imaging method processes the backscatter echo signal from nonlinear scattering to generate image data along the bisector of each xAM sequence employed. As mentioned above, the backscatter echo signals from the ultrasound transducer array are generally in the form of radio frequency (RF) signals. In some cases, the backscatter echo signals are amplified by an amplifier, e.g., through linear amplification. Various methods can be used to process the backscatter echo signals to generate image data. In many implementations, at operation 1472 the xAM method also determines an envelope of the backscatter echo signals, e.g., by making a Hilbert transform of each of the backscatter echo signals.

An example of details of image reconstruction and dynamic focusing is discussed in xAM beamforming Section IV(C).

At operation 1480, the backscatter echo data from the nonlinear scattering at the virtual bisector of each xAM pulse sequences is combined to reconstruct an ultrasound image of the nonlinear scatterers over the desired field-of-view for each cross-propagating angle. Image reconstruction includes applying xAM beamforming to the backscatter echo signal for nonlinear scattering from operation 1472. Images for different sets of adjacent cross-propagating angles are combined to generate one or more coherent compounded images. In one implementation, for example, the number in the sets of adjacent cross-propagating angles is four. In this case, images of different sets of four adjacent cross-propagating angles will be combined to generate coherent compounded images. For example, a first coherent compounded image is generated by combining images based on the first, second, third and fourth adjacent cross-propagating angles and a second coherent compounded image is generated by combining images based on the second, third, fourth, and fifth adjacent cross-propagating angles, and so forth. After generating the one or more coherent compounded images, the xAM method ends.

In some implementations, the number of compounded adjacent angles is in a range between 2 to 5 angles. In one implementation, the number of compounded adjacent angles is four angles. In another implementation, the number of compounded adjacent angles is three angles. In another implementation, the number of compounded adjacent angles is two angles. In another implementation, the number of compounded adjacent angles is in a range between 4-6 angles.

In some cases, the xAM methods implementing coherent compounding of xAM backscatter echo data may increase CTR and CAR of images. For example, a comparison of coherent compounding with single-acquisition xAM images provided in the section below demonstrated that xAM data acquired at four different angles θ can increase CTR and CAR. The tradeoff to implementing coherent compounding is that the depth of field may be reduced in certain instances as the cross-propagating angle increases. The xAM image depth can be extended beyond the intersection distance of the X wave by using spherical delay laws discussed in Renaud, G., Bosch, J. G., van der Steen, A. F., and de Jong. N., "Increasing Specificity of Contrast-Enhanced Ultrasound Imaging Using the Interaction of Quasi Counter-Propagating Wavefronts: A Proof of Concept," IEEE Trans. Ultrason. Ferroelectr. Freq. Control 62, 1768 (2015), but the quality of nonlinear artifact reduction may decline with depth.

1. Comparison of Coherent Compounding with Single-Acquisition xAM Images

The effect of coherent compounding of the rf backscatter echo data from multiple xAM acquisitions with different numbers of cross-propagation angles was evaluated. Because of the difference in interaction velocity for different angles, the rf data from individual acquisitions was first aligned with the peak of the average autocorrelation function of the individual beamformed ray lines composing the images. For this example, the best results were achieved by compounding four adjacent angles. In this example, the average CTR was improved by 1.7 dB and the peak CAR was improved by 0.5 dB.

Figure 15:
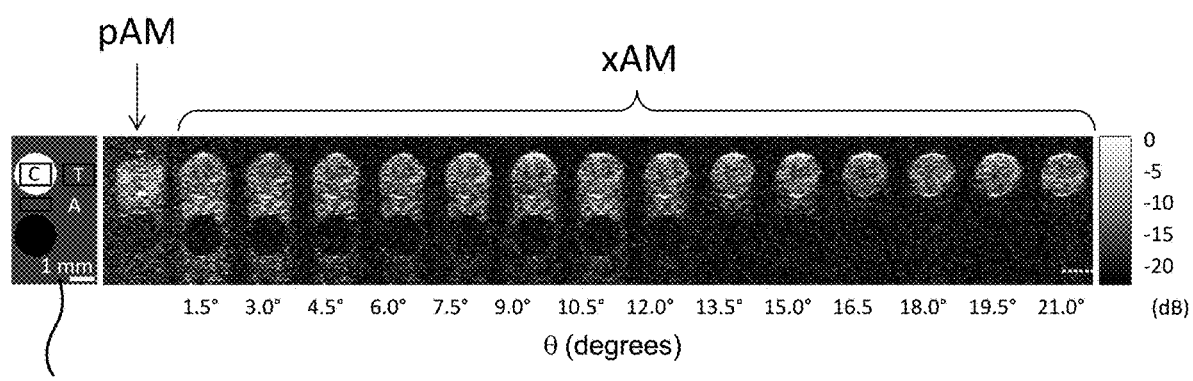
FIG. 15 includes a set of in vitro pAM and xAM images of an engineered harmonic variant gas vesicles (hGV) inclusion in a tissue-mimicking phantom and the schematic drawing of the phantom configuration, according to various implementations.
Figure 21A:
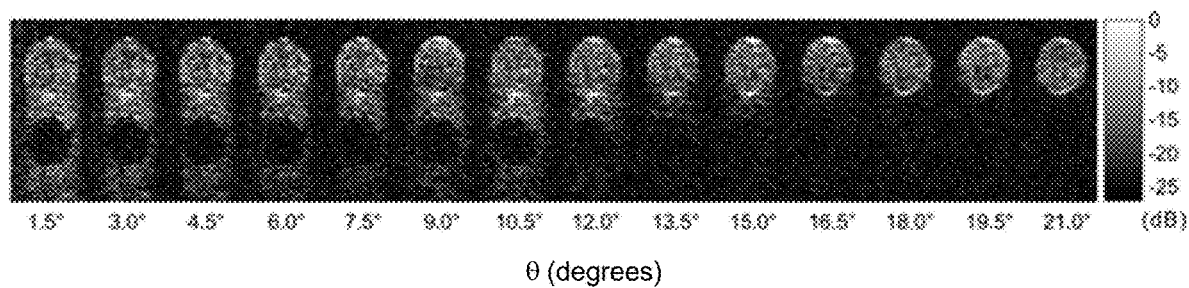
FIG. 21A includes a set of xAM images from the experiment depicted in FIG. 15.
Figure 21B:
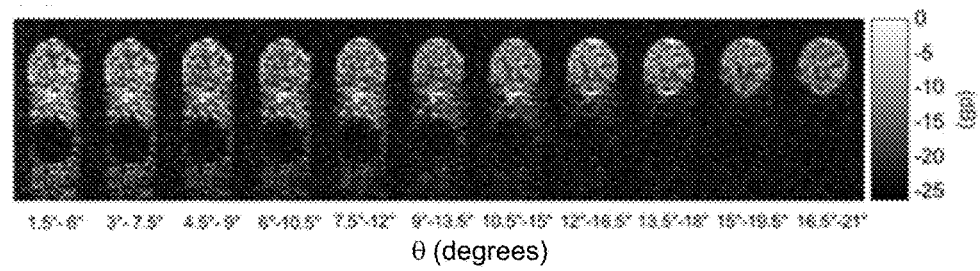
FIG. 21B includes a set of images from an xAM method with coherent compounding, according to an implementation.

FIG. 21A includes a set of xAM images from the experiment depicted in FIG. 15. FIG. 21B is the same set of images with coherent compounding applied to successive and overlapping sets of four acquisitions. For example, the first image in FIG. 21B is a coherent compounding of the first, second, third and fourth images of FIG. 21A and the second image in FIG. 21B is a coherent compounding of the second, third, fourth, and fifth images of FIG. 21A.

Figure 22A:
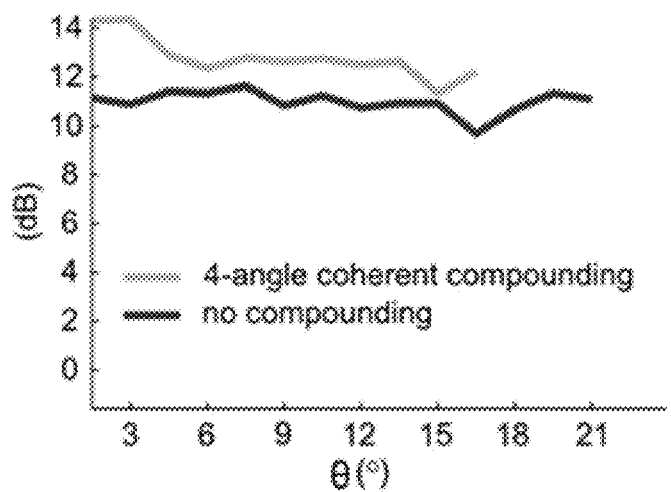
FIG. 22A is a plot comparing the contrast-to-tissue ratio of single-acquisition xAM compared with coherently compounded xAM, according to an implementation.
Figure 22B:
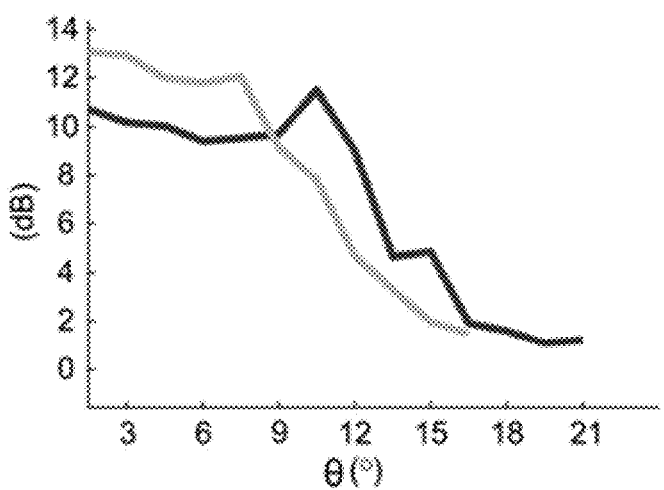
FIG. 22B is a plot illustrating the artifact-to-tissue ratio of single-acquisition xAM compared with coherently compounded xAM, according to an implementation.
Figure 22C:
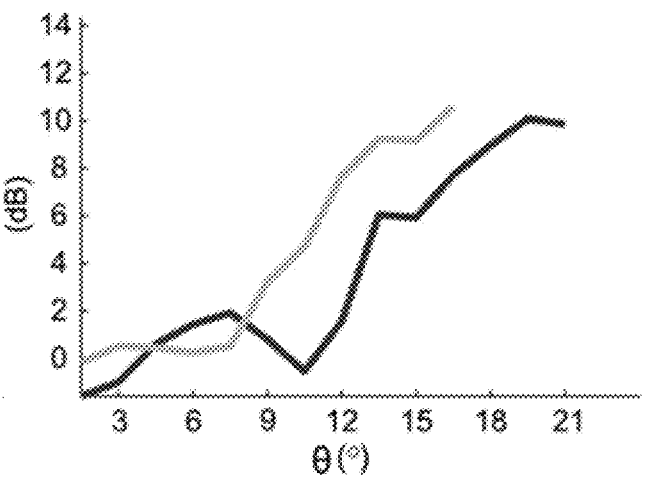
FIG. 22C is a plot illustrating the contrast-to-artifact ratio of single-acquisition xAM compared with coherently compounded xAM, according to an implementation.

FIG. 22A is a plot illustrating the contrast-to-tissue ratio of single-acquisition xAM compared with coherently compounded data as a function of cross-propagation angle. FIG. 22B is a plot illustrating the artifact-to-tissue ratio of single-acquisition xAM compared with coherently compounded data as a function of cross-propagation angle. FIG. 22C is a plot illustrating the contrast-to-artifact ratio of single-acquisition xAM compared with coherently compounded data as a function of cross-propagation angle. In these plots, n=6.

V. Cross-Amplitude Modulation (xAM) Imaging of Acoustic Biomolecules

A. Angle-Dependent Reduction of Nonlinear Propagation Artifacts

The xAM sequence was developed to detect hGVs and other nonlinear scatterers with high specificity. The peak positive pressure of a single tilted plane waves excites the hGVs in the linear scattering regime, while the doubled X-wave intersection amplitude excites the hGVs in the nonlinear scattering regime. By summing the echoes from the two plane-wave transmissions and then subtracting them from the echoes of the X-wave transmissions, we solely retrieve nonzero differential GV signals, while the echoes of surrounding linear scatterers cancel.

To evaluate the effectiveness of the xAM sequence, of an implementation, in reducing the nonlinear propagation artifact, a 2-mm-wide cylindrical inclusion of hGVs was embedded in agar (at a concentration of 256 pM) in a tissue-mimicking phantom consisting of agar and 3-μm aluminum oxide particles (a model linear scatterer). A second inclusion filled with a scatterer-free PBS/agar mixture is positioned 1 mm below the GVs as shown in the schematic diagram 1510 in FIG. 15. The phantom was imaged using the same sequence parameters used for the subwavelength scatterer measurements, with the top of the hGV inclusion positioned at 4 mm (as shown in the images in FIG. 15) since X waves provide extended depths of fields compared to parabolic beams. A discussion of Nondiffracting X Waves can be found in Lu, J. Y. and Greenleaf, J. F., "Nondiffracting X Waves-Exact Solutions to Free-Space Scalar Wave Equation and Their Finite Aperture Realizations, IEEE Trans. Ultrason. Ferroelectr. Freq. Control 39, 19 (1992), which is hereby incorporated by reference in its entirety. The method used to prepare the hGVs and the method used to prepare the tissue-mimicking phantom are described in the following Sections V(A)(1) and V(A)(2).

FIG. 15 depicts (to the right) an in vitro pAM image and a set of in vitro xAM images of an hGV inclusion in a tissue-mimicking phantom and the schematic drawing 1510 (leftmost panel) of the phantom configuration. The schematic drawing (leftmost panel) of the phantom configuration indicates that the linearly scattering tissue-mimicking medium is shown in gray, the hGV inclusion is the top-most circle and the anechoic agar-filled inclusion is in black. ROIs are shown for contrast (C), tissue (T), and artifact (A) quantification. The scale bar in the schematic drawing 1510 is 1 mm mimicking phantom. The set of in vitro pAM and xAM images is of a representative well positioned at z=4 mm. Separate images spanning depths of 3 mm to 9 mm are concatenated. The white dotted line at the right edge of the images is at $z_X$ at cross-propagating angle θ=21 degrees.

Figure 16A:
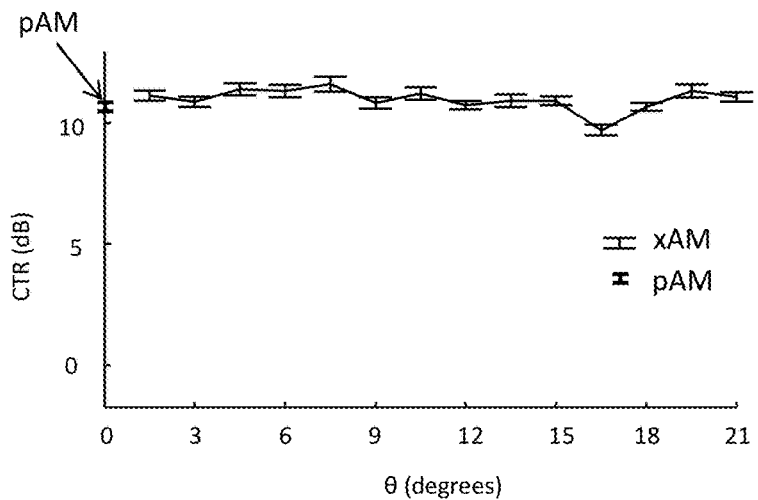
FIG. 16A is a plot of contrast-to-tissue ratio (CTR) as a function of cross-propagating angle θ, according to various implementations.
Figure 16B:
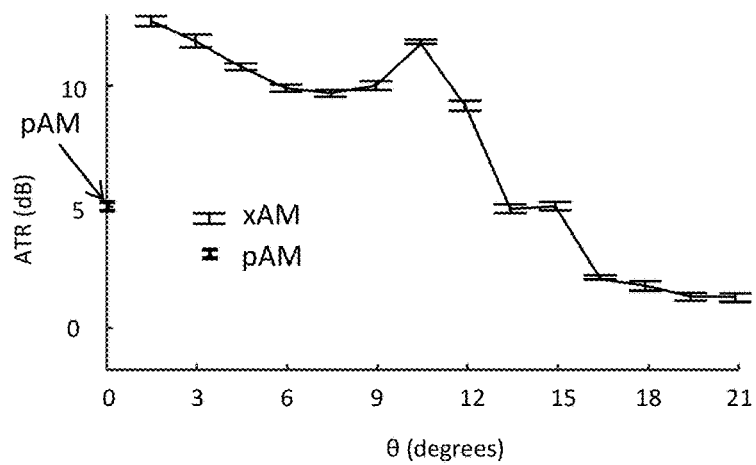
FIG. 16B is a plot of artifact-to tissue ratios (ATR) as a function of cross-propagating angle θ, according to various implementations.
Figure 16C:
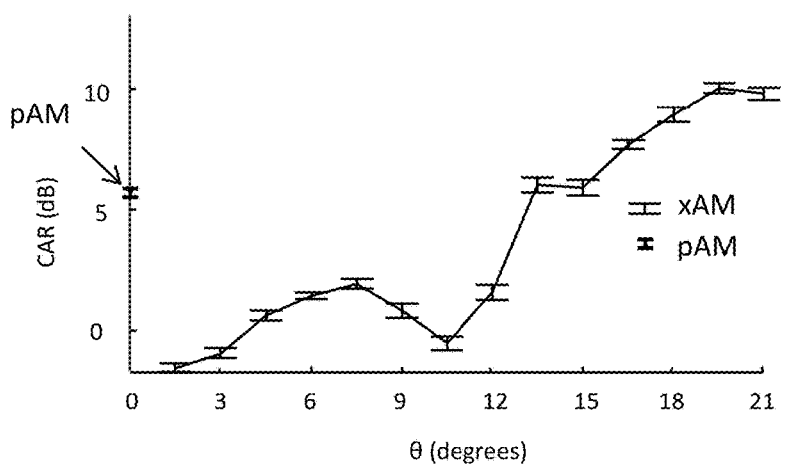
FIG. 16C is a plot of contrast-to-artifact ratios (CAR) as a function of cross-propagating angle θ, according to various implementations.

With parabolic and low-θ xAM pulses, a significant nonlinear propagation artifact is observed distal to hGV inclusions, as shown in FIG. 15, confirming the high nonlinearity of hGV-filled media. The pAM and xAM images in FIG. 15 were quantified in terms of contrast-to-tissue ratios (CTR), contrast-to-artifact ratios (CAR), and artifact-to tissue ratios (ATR) and the results are shown in FIGS. 16A-16C. FIG. 16A is a plot of CRT as a function of cross-propagating angle θ. FIG. 16B is a plot of ATR as a function of cross-propagating angle θ. FIG. 16C is a plot of CAR as a function of cross-propagating angle θ where N–6. For pAM and low-θ angles, the artifact intensity is on par with or above the hGV inclusion intensity (e.g., for θ=1.5 degrees, CAR=–1.6 dB at z=4 mm), highlighting the specificity issue posed by collinear AM imaging. For angles above 15 degrees, xAM produces images with a clear reduction in artifact signal while maintaining full contrast in the hGV inclusion. As in the simulation and subwavelength scatter results, the artifact reduction is also observed to be a nonmonotonic function of θ, with a local jump in the xAM artifact at 10.5 degrees in FIG. 16B. Overall, these results suggest that xAM provides the highest specificity for hGV signals at angles larger than 15 degrees.

1. Engineering of Harmonic Acoustic Protein Nanostructures

Anabaena GVs were cultured and transferred to sterile separating funnels, and the buoyant cells are allowed to float to the top and separate from the spent media over a 48 hour period. GVs were harvested by hypertonic lysis. Purification was done by repeated centrifugally assisted flotation followed by resuspension. Wild-type Ana GVs are stripped of their outer GvpC layer by treatment with 6-M urea solution to obtain hGVs. Next, two rounds of centrifugally assisted flotation are followed by removal of the subnatant layer to ensure complete removal of native GvpC. More detailed discussion can be found in Lakshmanan et al., "Preparation of Biogenic Gas Vesicle Nanostructures for Use as Contrast Agents for Ultrasound and MRI," Nat. Protoc. 12, 2050 (2017), which is hereby incorporated by reference in its entirety.

2. Tissue-Mimicking Phantom 3D Design and Preparation

Tissue-mimicking phantoms for imaging were prepared by melting 1% (w/v) agarose gel in PBS and with 0.2% (w/v) $AlO_3$. A custom 3D-printed mold was used to create a 2-by-2 grid of cylindrical wells with 2 mm diameter and 1 mm spacing between the outer radii in the bulk material.

GVs were incubated at 42 degrees C. for 1 minute and then mixed in a 1:1 ratio with molten agarose (at 42 degrees C.) for a final GV concentration corresponding to 2.25 OD500 nm and immediately loaded into the phantom. Wells not containing GVs are filled with plain 1% agar. The $AlO_3$ concentration is chosen to match the scattering echogenicity of the GV well as measured by the contrast-to-noise ratio of the respective regions in a B-mode ultrasound image. The phantoms used for the angle ramp images contain stripped Ana GVs in the upper-left well. The phantom used for the voltage ramp images contains wild-type Ana GVs in the upper-left well and stripped Ana GVs in the upper-right well. All phantoms are imaged on top of an acoustic absorber material while immersed in PBS. Based on the elevation f-number of the probe, the elevation resolution (i.e., the thickness of the imaging plane) is 512 μm. The molarity of Ana GVs for a given OD value is 114 pM=OD. Using these values and the dimensions of the hGV inclusion, it was estimated that $2.47 \times 10^5$ GVs contribute to each image, or roughly 200 GVs for each pixel.

B. In Vivo xAM Ultrasound Imaging of Acoustic Biomolecules

Figure 17:
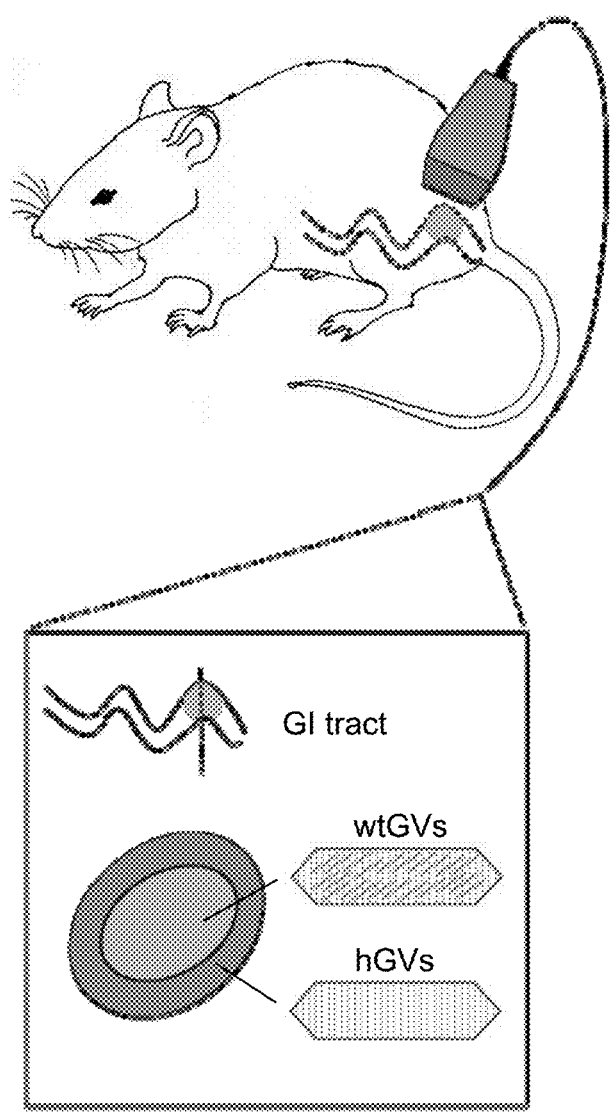
FIG. 17 is a schematic representation of an experiment performed with a concentric mixture of nonlinearly scattering hGVs and linearly scattering wild type gas vesicles (wtGVs) that were injected in a mouse gastrointestinal tract and imaged with pAM and xAM, according to an implementation.

To test the xAM imaging method, of certain implementations, in vivo a patterned agar-GV mixture was injected into the gastrointestinal tract of a mouse. The patterned agar-GV mixture consisted of a core of wild-type linearly scattering GVs (wtGVs) surrounded by a circular layer of hGVs. The mouse abdomen was imaged using xAM pulse sequence at θ=19.5 degrees, which yields the highest contrast-to-artifact ratio in the phantom experiments. FIG. 17 is a schematic representation of the experiment performed with a concentric mixture of nonlinearly scattering hGVs and linearly scattering wtGVs that were injected in a mouse gastrointestinal (GI) tract and imaged with pAM and xAM, according to an implementation. The results were compared to imaging with pAM with the focus adjusted to 4 mm and an aperture of 20 element (f-number=2.0) to align the depth of field with that of the xAM pulse sequence.

Figure 18A:
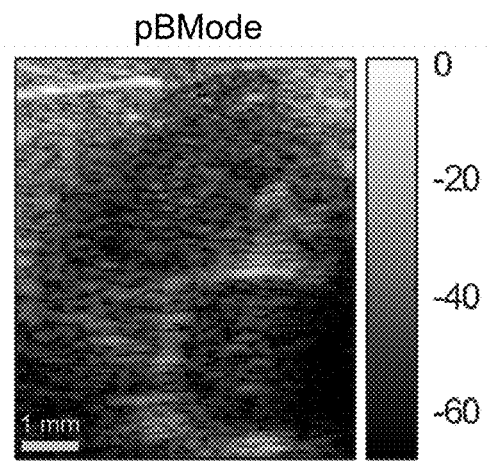
FIG. 18A is a pBmode image, according to an implementation.
Figure 18B:
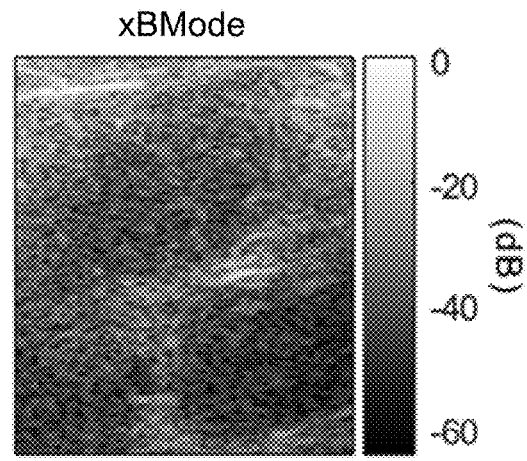
FIG. 18B is an xBmode image, according to an implementation.
Figure 18C:
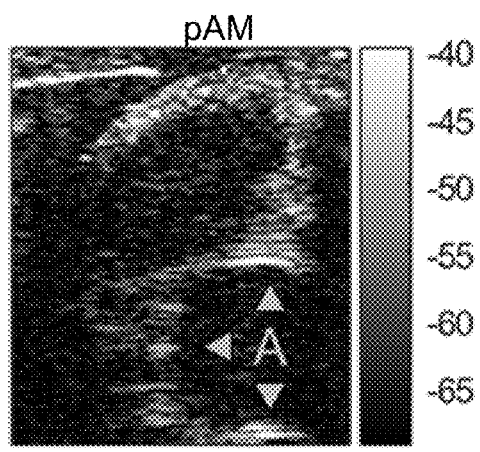
FIG. 18C is an pAM image, according to an implementation.
Figure 18D:
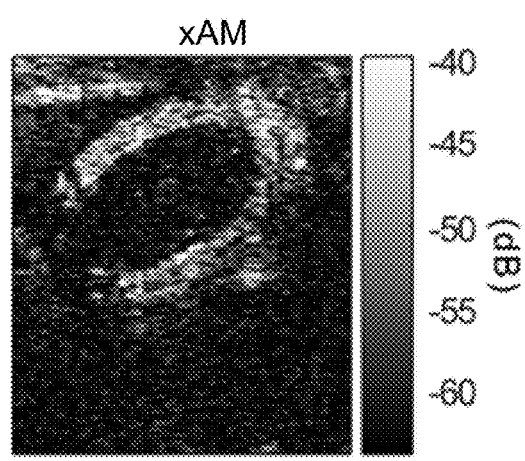
FIG. 18D is an xAM image, according to an implementation.
Figure 19:
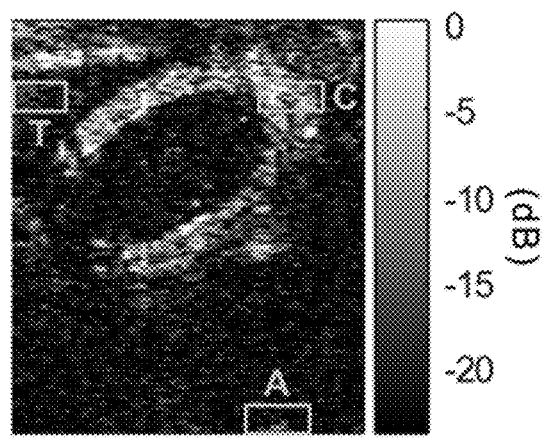
FIG. 19 is the xAM image of FIG. 18D with indicators showing the Tissue (T), contrast (C), and artifact (A) in the regions of interest (ROI).

FIG. 18A is a pBmode image with focus at z=4 mm and f-number=2.0. FIG. 18B is a xBmode image, according to an implementation. Arrows are shown pointing to the artifact. FIG. 18C is an pAM image with angle 19.5 degrees according to an implementation. FIG. 18D is an xAM image, according to an implementation. In FIGS. 18A, 18B, 18C, and 18C, the image depths range from z=2 mm to $Z_x$=9.2 mm defining the depth of field. Comparison of xAM and pAM images in terms of mean CTR and CAR. N=3. ROIs for CTR and CAR measurements are provided in Section V(B)(1) below. FIG. 19 shows the xAM image of FIG. 18D with indicators showing the Tissue (T), contrast (C), and artifact (A) in the regions of interest (ROI) used in FIGS. 18A-18D.

The parabolic B-mode (pBMode) image in FIG. 18A, i.e., the conventional anatomical ultrasound image, is sharper than the cross-propagating B-mode (xBMode) image in FIG. 18C and, which is expected, as X waves generate higher side lobes that reduce image contrast. Additional discussion can be found at Lu, J.-Y. and Greenleaf, J. F., "Theory and acoustic experiments of nondiffracting X-waves (medical US imaging application)," IEEE 1991 Ultrasonics Symposium, Vol. 1152, pp. 1155-1159 (December 1991), which is hereby incorporated by reference for this discussion.

Only the top of the hGV inclusion is visible in the pAM image due to the narrow depth of field of parabolic beams as shown in FIG. 18B. In FIG. 18B, the pAM image also contains a large artifact below the inclusion (CTR=2.8 dB, CAR=-2.6 dB), parts of which blend with the hGV signal, displaying a potentially misleading distribution of the contrast agent. In contrast, the annular hGV inclusion is almost entirely visible in the xAM image shown in FIG. 18D, with little-to-no artifact in the vicinity, and inner and outer contours more clearly delineated.

Figure 20:
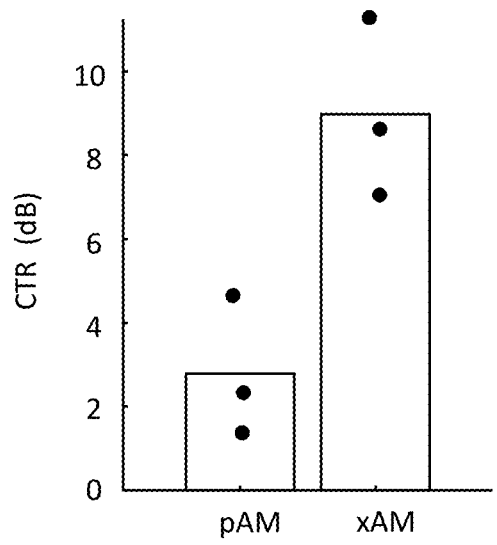
FIG. 20 includes plots of results comparing xAM imaging to pAM imaging, according to an implementation.
Figure 20:
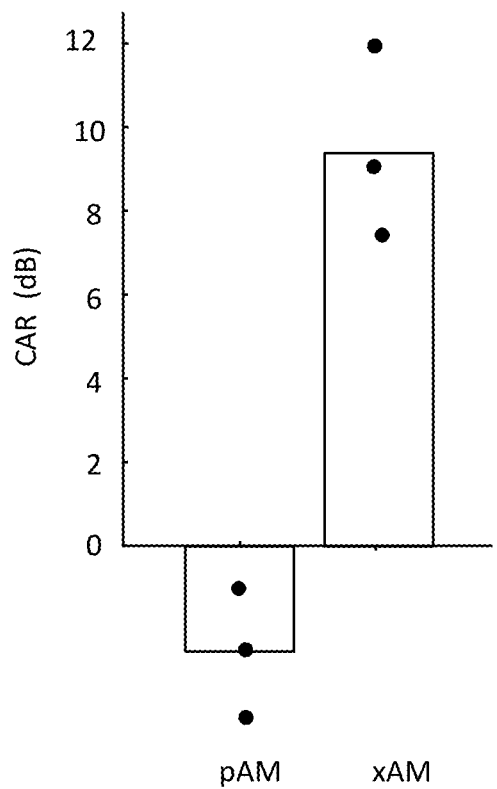

The xAM CTR is 9.0 dB, and the xAM CAR is 9.6 dB, demonstrating the superior performance of xAM over pAM in terms of specificity. The regions of interest for CTR and CAR measurements are reported in FIG. 20. FIG. 20 shows plots xAM and pAM imaging in terms of mean CTR and CAR to show the superior performance of xAM over pAM in terms of specificity. For these plotted data, N=3.

1. In Vivo Ultrasound Imaging

The in vivo experiment was performed on a C57BL/6J male mouse (Jackson Laboratory) under a protocol approved by the Institutional Animal Care and Use Committee of the California Institute of Technology. No randomization or blinding was necessary in this study. Ultrasound imaging is performed as follows: The mouse is anaesthetized with 2%-3% isoflurane, depilated over the imaged region, and imaged using an L22-14v transducer with the pulse sequence described in Section IV(B). For imaging of GVs in the gastrointestinal tract, the mouse is placed in a supine position, with the ultrasound transducer positioned on the lower abdomen, transverse to the colon. Prior to imaging, wild-type and stripped Ana GVs are mixed in a 1:1 ratio with 42 degrees C. 4% agarose-PBS for a final GV OD500 nm equal to 2.25. An 8-gauge needle is filled with the mixture of agarose and stripped Ana GVs. Before it solidifies, a 14-gauge needle is placed inside the 8-gauge needle to form a hollow lumen within the gel. After the agarose-GV mixture solidifies at room temperature for 10 min, the 14-gauge needle is removed. The hollow lumen is then filled with the agarose mixture containing the wildtype Ana GVs. After it solidifies, the complete cylindrical agarose gel is injected into the colon of the mouse with a PBS back-filled syringe. Additional PBS is then injected into the colon to remove air bubbles in the vicinity of the gel.

C. Supersonic Cross-Propagating Plane-Wave Intersection

Figure 23:
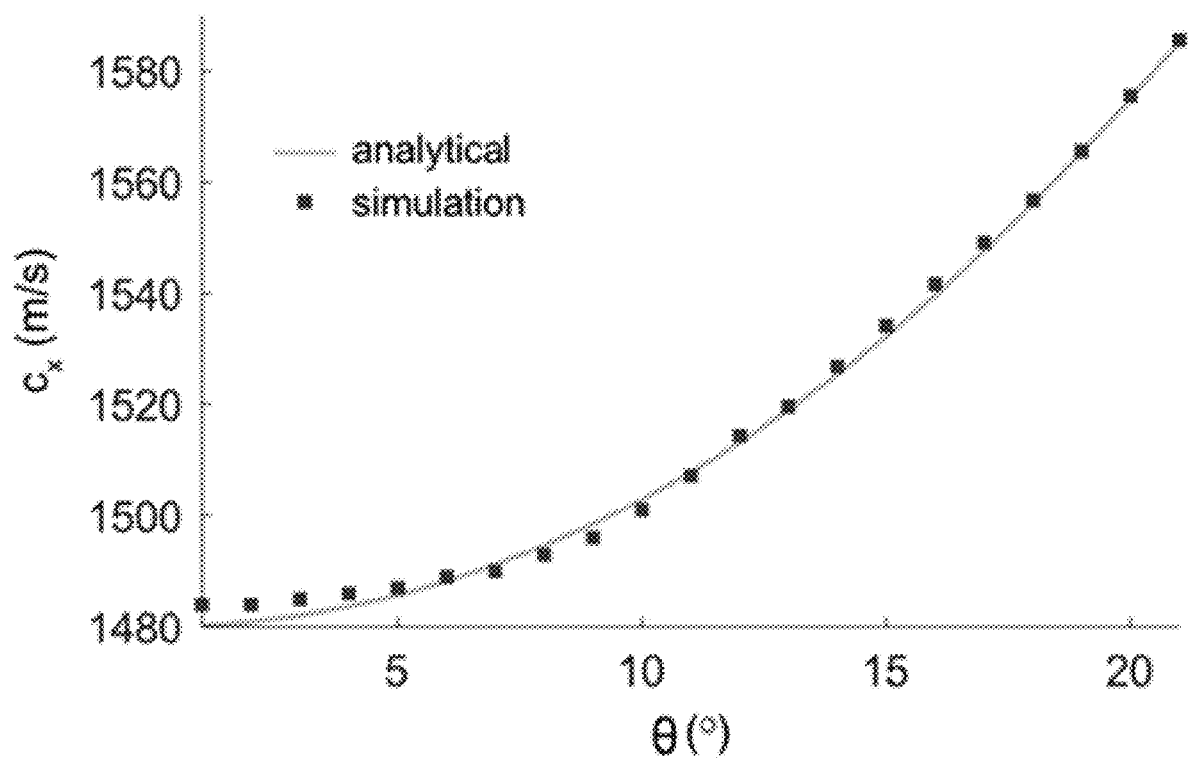
FIG. 23 is a plot of the analytical and simulated cross-propagation plane-wave intersection velocity as a function of cross-propagation angle, according to an implementation.

Interestingly, theory and simulations predict that the peak of the cross-propagating plane waves travels at a supersonic velocity, increasing as θ opens, an effect that may be linked to the decreasing nonlinear interaction of the planar wavefronts. As both plane waves cross propagate, local coordinates of each wave-front interact with their axisymmetric counterpart, but contrary to co-propagating plane waves, it is a transient interaction. The plane-wave intersection velocity $c_x$ is given by:

$$c_x = \frac{c_0}{\cos\theta} \qquad \text{(Eqn. 9)}$$

where $c_0$ is the speed of sound in the propagation medium. It can readily be seen from Eqn. 9 and shown in FIG. 23 that the plane-wave intersection velocity $c_x$ is supersonic for θ>0 as reported by Lu, J. Y. and Greenleaf, J. F., "Nondiffracting X Waves-Exact Solutions to Free-Space Scalar Wave Equation and Their Finite Aperture Realizations, IEEE Trans. Ultrason. Ferroelectr. Freq. Control 39, 19 (1992), which is hereby incorporated by reference in its entirety. FIG. 23 shows the analytical and simulated cross-propagation plane-wave intersection velocity as a function of cross-propagation angle. The third transmission event of the xAM sequence shown in FIG. 3C corresponds to a finite-aperture forward propagating X-wave solution of the homogeneous and isotropic wave equation with the form $f(x, z-c_x t)$ where f represents a scalar function (e.g., the acoustic pressure pulse) of space and time, although in our case X wave pressure distribution is constant along its branches.

VI. Additional Examples

Certain implementations of the xAM ultrasound pulse sequence based on one X wave and two tilted plane-wave transmissions may achieve highly specific nonlinear imaging of acoustic biomolecules through wave-amplitude modulation. In some cases, two noncollinear plane waves interact to generate a twofold amplitude modulation at their intersection with minimal nonlinear distortion for cross-propagation angles θ above 15 degrees. This allows retrieval of nonzero differential hGV signals, while the echoes of surrounding linear scatterers cancel and propagation artifacts are reduced to the noise floor level (−10 dB at 18 degrees). With a 6.4-mm aperture, the xAM ultrasound technique of certain implementations provides a depth of field suitable for small-animal imaging (10 mm at 18 degrees). In addition, certain implementations of the xAM sequence are robust enough to suppress in vivo artifacts present in pAM while distinguishing engineered nonlinear hGVs from linearly scattering wild-type GV variants in the gastrointestinal tract of a mouse.

Implementations of the xAM ultrasound pulse sequence can be used with nonlinear contrast agents, with purified GVs as the model agent, and also with GVs as functionalized contrast agents and as reporter genes expressed inside cells. Implementations of the xAM ultrasound pulse sequence can be used for in vivo biomolecular ultrasound studies of molecular and cellular processes based on visualization of acoustic biomolecules.

Additionally, various embodiments can also be implemented with non-linear scatterers in surrounding linear scattering environments other than tissue. For example, these embodiments can be implemented with the non-linear scatterers in agar, water, or other linearly-scattering media.

1. Microbubbles

Although certain embodiments are described herein as imaging gas vesicles, it would be understood that these embodiments can also be implemented to image other non-linear scatterers. For example, the xAM method of certain embodiments can be used to generate artifact-free images of synthetic microbubble-based ultrasound contrast agents.

Figure 24A:
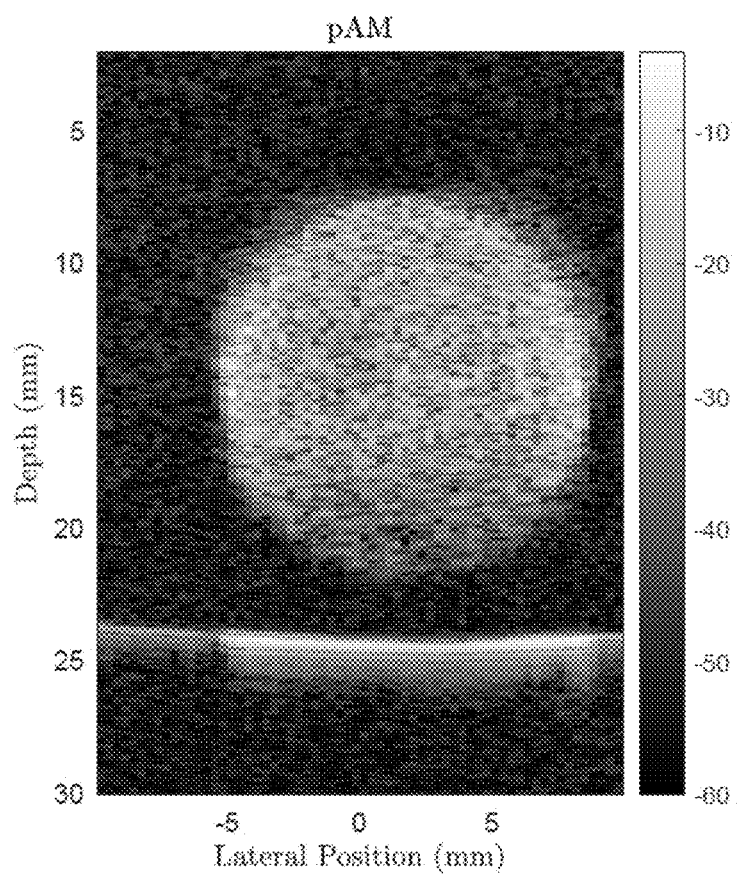
FIG. 24A is an image of microbubbles and a subwavelength nickel wire below the microbubbles acquired using a parabolic amplitude modulation (pAM) imaging method, according to an implementation.
Figure 24B:
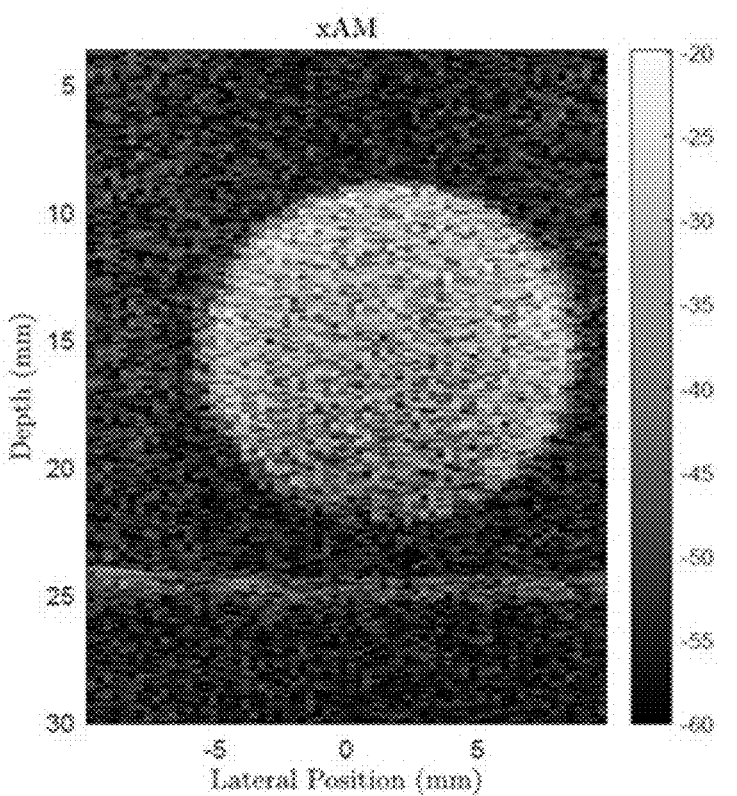
FIG. 24B is an image of microbubbles and a subwavelength nickel wire below the microbubbles acquired using an xAM imaging method, according to an implementation.
Figure 24C:
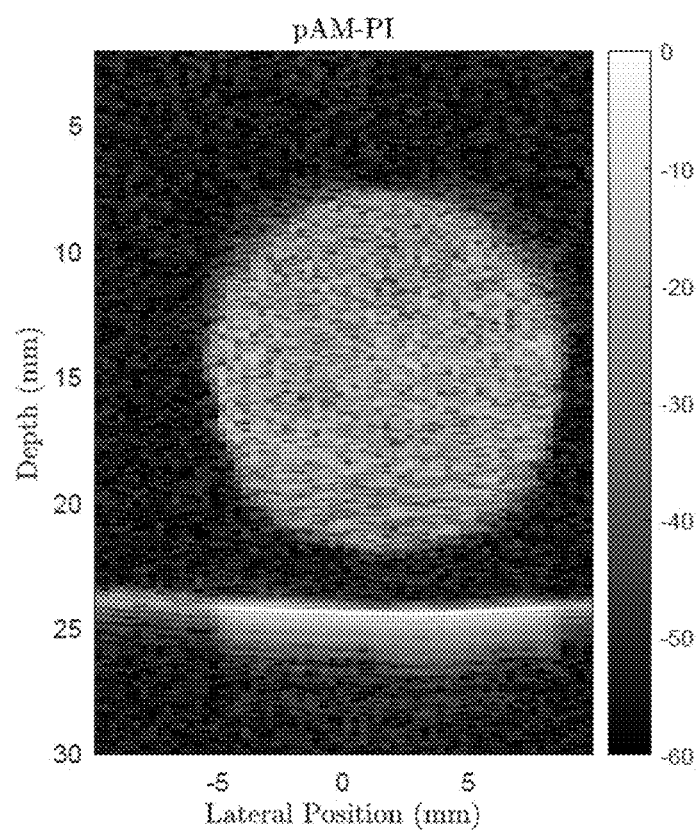
FIG. 24C is an image of microbubbles and a subwavelength nickel wire below the microbubbles acquired using combined pAM and pulse inversion (pAM-PI) imaging method, according to an implementation.
Figure 24D:
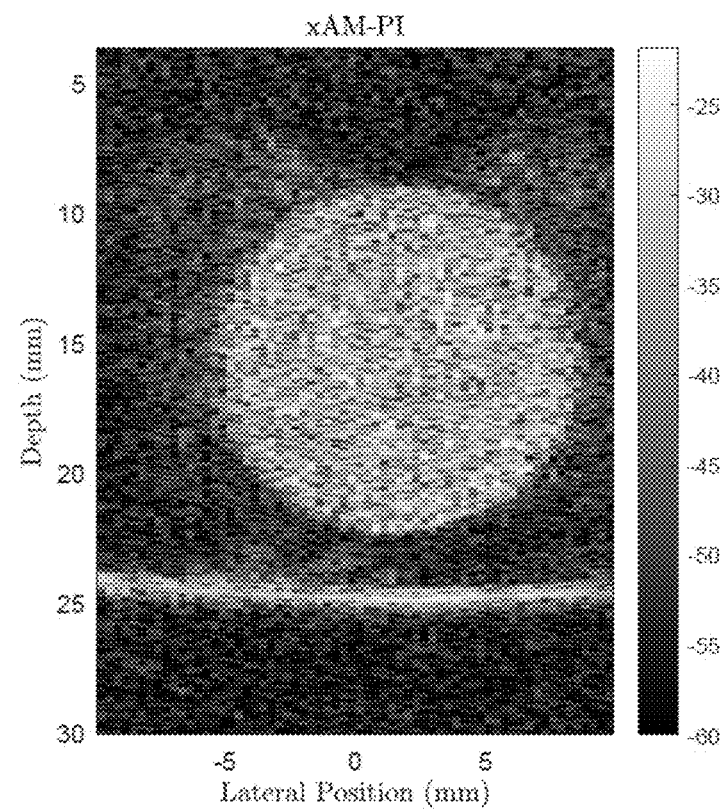
FIG. 24D is an image of microbubbles and a subwavelength nickel wire below the microbubbles acquired using combined xAM and pulse inversion (xAM-PI) imaging method, according to an implementation.

FIG. 24A is an image of microbubbles and a subwavelength nickel wire below the microbubbles acquired using a parabolic amplitude modulation (pAM) imaging method, according to an implementation. FIG. 24B is an image of microbubbles and a subwavelength nickel wire below the microbubbles acquired using an xAM imaging method, according to an implementation. FIG. 24C is an image of microbubbles and subwavelength nickel wire below the microbubbles acquired using combined pAM and pulse inversion (pAM-PI) imaging method, according to an implementation. FIG. 24D is an image of microbubbles and a subwavelength nickel wire below the microbubbles acquired using combined xAM and pulse inversion (xAM-PI) imaging method, according to an implementation.

By comparing the image acquired using pAM in FIG. 24A with the image acquired using xAM in FIG. 24B, it can be seen that xAM imaging technique reduces the artifact below the inclusion of microbubbles. Similarly, by comparing the image acquired using pAM-PI in FIG. 24C with the image acquired using xAM-PI in FIG. 24D, it can be seen that xAM imaging technique reduces the artifact below the inclusion of microbubbles.

2. Adaptive Wavefront-Shaping

In certain implementations, the xAM methods described herein can further include adaptive wavefront-shaping techniques developed in optics and acoustics as discussed in Want, K., Sun, W., Richie, C. T., Harvey, B. K., Betzig, E., and Ji, N., "Direct Wavefront Sensing for High-Resolution In Vivo Imaging in Scattering Tissue," Nat. Commun. 6, 7276 (2015) and Imbault, M., Faccinetto, A., Osmanski, B.-F., Tissier A., Deffieux, T., Gennisson J.-L, Vilgrain V., and Tanter M., "Robust Sound Speed Estimation for Ultrasound-Based Hepatic Steatosis Assessment," Phys. Med. Biol. 62, 3582 (2017), which is hereby incorporated by reference in its entirety. In these implementations, the xAM methods can address the dissymmetric phase-aberrating media like biological tissues.

3. Two-Dimensional Transducer Array with Ultrafast Frame Rates

In certain implementations, the xAM method implements one or more two-dimensional transducer arrays. In these cases, tilted plane waves that cross-propagate and intersect along a plane rather than a line are transmitted. With this approach, a two-dimensional xAM image can be obtained from a single three pulse xAM transmission. A volumetric xAM image can be obtained from multiple three pulse xAM transmissions. In some cases, the two-dimensional transducer array(s) implement ultrafast frame rates, which can further improve sensitivity or the temporal resolution. In one implementation, the frame rate implemented is in the range of 0.5 kHz to 30 kHz. Examples of ultrasound ultrafast imaging are described in Tanter, M. and Fink M., "Ultrafast Imaging in Biomedical Ultrasound," IEEE Trans. Ultrason. Ferroelectr. Freq. Control 61, 102 (2014) and Provost, J., Papadacci, C., Arango, J. E., Imbault, M., Fink M., Gennisson, J.-L., Tanter, M., and Pernot, M., "3D Ultrafast Ultrasound Imaging In Vivo," Phys. Med. Biol. 59, L1 (2014), which are hereby incorporated by reference in their entireties.

4. Multiplexed Imaging

As discussed above, different variations of hGVs can have different buckle, collapse, and/or cavitate thresholds. In certain implementations, these thresholds can be used to differentiate between different hGVs being imaged. For example, the xAM method may have multiple imaging operations where each imaging operation uses the xAM pulse sequence that generates a peak acoustic pressure at the bisector of the X-waves that is above a threshold of one type of hGV. The xAM method can use the backscatter echo data to differentiate between the different types of hGVs.

5. Cavitation and Collapse Thresholds

Although many implementations include an xAM pulse sequence with simultaneous transmission of cross-propagation plane waves designed to generate a peak acoustic pressure at the intersecting bisector above a buckling threshold of nonlinear scatterers, other implementations may involve other thresholds such as cavitation thresholds and collapse thresholds. For example, the xAM imaging method may, additionally or alternatively, include a pulse with cross-propagation plane waves designed to generate a peak acoustic pressure that is above the collapse threshold of a particular variety of nonlinear scatterers to release the contents of the cells with the nonlinear scatterers and extinguish the signal from the nonlinear scatterers. As another example, the xAM imaging method may, additionally or alternatively, include a pulse with cross-propagation plane waves designed to generate a peak acoustic pressure that is at or above the cavitation threshold of a particular variety of nonlinear scatterers.

6. xAM Method with Pre-Scanning Operation to Locate Non-Linear Scatters GVs—Scanning at Low Pressure to Generate Attenuation Map to Locate the GVs In one implementation, one could pre-scan the field of view at a low ultrasound pressure (below GV buckling) to estimate attenuation in the field of view of the ultrasound probe. Based on the knowledge of attenuation is that specific slice of tissue, the pressure output of the transducer probe could be adjusted to induce buckling at any desired depth.

7. xAM Method for Slice Imaging and Volumetric Imaging

In certain implementations, the xAM method can be used to generate a "slice" image at a particular depth. In one implementation, a slice image is generated using a two-dimensional array. A volumetric image can be generated by contiguous subapertures of the two-dimensional array. For example, multiple slice images can be stacked between depths, $z_1$ and $z_2$.

8. Automatic Focusing and Other Tuning

In some implementations, the xAM method includes operations for automatically tuning the imaging parameters to optimal settings. For example, the xAM method depicted in the FIG. 7 may further include a feedback loop to adjust the imaging parameters based on certain criteria such as removing the artifact at a particular depth of field.

In one implementation, the xAM method may increase the voltage pulse in voltage increments (that avoid collapse) to minimize the artifact in the image. The xAM method can detect the pixel intensities of the image and include a pattern matching operation that matches the pixel intensity of the image to find a signal characteristic of the nonlinear scatterer (e.g., hGV) and then stop increasing the voltage when the nonlinear scatterer is imaged. Alternatively, another pattern matching operation can match the pixel intensity of the image to find a signal characteristic of the artifact and when the ratio of nonlinear scatterer signal to artifact signal stops improving, the increasing of the voltage increment is stopped.

9. An xAM Method with Two-Pulse xAM Pulse Sequence

One implementation pertains to an xAM method that includes a two pulse sequence. For example, an ultrasound transducer array may include a first set (subaperture) of transducer elements configured to transmit a first ultrasound plane wave and a second set of transducer elements configured to transmit a second ultrasound plane wave that is noncollinear to the first ultrasound plane wave, wherein the second ultrasound plane wave is axisymmetric to the first ultrasound plane wave about a bisector. The transducer array is configured to transmit an xAM ultrasound pulse sequence by activating the first set of transducer elements to transmit the first ultrasound plane wave to generate a first pulse, and also simultaneously activating both the first and second sets of transducer elements to transmit the first and second ultrasound plane waves to generate a second pulse. The first and second ultrasound plane waves of the third pulse are configured to intersect at the bisector to generate a peak acoustic pressure that is above a threshold along the bisector. The xAM method digitally subtracts twice the values of the backscatter echo data from activating the first set of transducer elements from the backscatter echo data from simultaneously activating both the first and second sets of transducer elements.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, object-oriented techniques. The software code may be stored as a series of instructions, or commands on a CRM such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A cross-amplitude modulation (xAM) ultrasound transducer system comprising:
   one or more transducers;
   a first subaperture of transducer elements of the one or more transducers, the first subaperture configured to transmit a first ultrasound plane wave when activated; and
   a second subaperture of transducer elements of the one or more transducers, the second subaperture configured to transmit a second ultrasound plane wave when activated, wherein the second ultrasound plane wave is noncollinear to the first ultrasound plane wave and axisymmetric to the first ultrasound plane wave about a virtual bisector;
   wherein the first and second subapertures are configured to transmit an xAM ultrasound pulse sequence by transmitting the first ultrasound plane wave, transmitting the second ultrasound plane wave, and simultaneously transmitting both the first and second ultrasound plane waves, wherein the first and second ultrasound plane waves are configured to generate an acoustic pressure that is above a threshold along the virtual bisector.

2. The xAM ultrasound transducer system of claim 1, wherein each of the first and second ultrasound plane waves propagate at a cross-propagation angle with respect to the virtual bisector.

3. The xAM ultrasound transducer system of claim 2, wherein the cross-propagation angle is greater than 15 degrees.

4. The xAM ultrasound transducer system of claim 2, wherein the cross-propagation angle is in a range between 15 and 20 degrees.

5. The xAM ultrasound transducer system of claim 1, wherein each of the first and second ultrasound plane waves has an amplitude that is half the threshold.

6. The xAM ultrasound transducer system of claim 1, wherein the threshold is one of a buckling threshold, a collapse threshold, and a cavitation threshold of a contrast agent.

7. The xAM ultrasound transducer system of claim 6, wherein the contrast agent is an engineered harmonic gas vesicle or a microbubble.

8. The xAM ultrasound transducer system of claim 1, wherein the one or more transducers are further configured to transmit the xAM ultrasound pulse sequence at different locations by activating different subapertures of transducer elements.

9. The xAM ultrasound transducer system of claim 1, wherein at least one of the one or more transducers is a one-dimensional array or a two-dimensional array.

10. The xAM ultrasound transducer system of claim 1, wherein the first subaperture of transducer elements and the second subaperture of transducer elements are located along a curve.

11. The xAM ultrasound transducer system of claim 1, wherein the one or more transducers are further configured to detect backscatter echoes.

12. The xAM ultrasound transducer system of claim 1, wherein the first subaperture of transducer elements is part of one transducer and the second subaperture of transducer elements is part of another transducer.

13. The xAM ultrasound transducer system of claim 8, further comprising a computing device configured to cause activation of different subapertures of transducer elements of the one or more transducers to generate an xAM pulse sequence at different locations across a field of view, to receive backscatter echo signals from the one or more transducers, and to digitally subtract backscatter echo signals from the first ultrasound plane wave and the second ultrasound plane wave from backscatter echo signals from simultaneous transmission of both the first and second ultrasound plane waves to generate a substantially artifact-free image of nonlinear scatterers in the field of view.

14. A cross-amplitude modulation (xAM) ultrasound imaging method comprising:
(i) causing excitation of a first subaperture of transducer elements of one or more transducers to transmit a first ultrasound plane wave;
(ii) causing excitation of a second subaperture of transducer elements of the one or more transducers to transmit a second ultrasound plane wave that is non-collinear to the first ultrasound plane wave, wherein the second ultrasound plane wave is also axisymmetric to the first ultrasound plane wave about a bisector; and
(iii) causing simultaneous excitation of both the first and second subapertures of transducer elements to transmit the first and second ultrasound plane waves simultaneously, wherein the first and second ultrasound plane waves are configured to cause an acoustic pressure above a threshold along the bisector.

15. The xAM ultrasound imaging method of claim 14, wherein each of the first and second ultrasound plane waves propagate at a cross-propagation angle with respect to the bisector.

16. The xAM ultrasound imaging method of claim 15, wherein the cross-propagation angle is greater than 15 degrees.

17. The xAM ultrasound imaging method of claim 15, wherein the cross-propagation angle is in a range between 15 and 20 degrees.

18. The xAM ultrasound imaging method of claim 14, wherein the first ultrasound plane wave and the second ultrasound plane wave have approximately the same amplitude.

19. The xAM ultrasound imaging method of claim 14, wherein the amplitudes of the first and second ultrasound plane waves are below the threshold value.

20. The xAM ultrasound imaging method of claim 14, wherein the threshold is one of a buckling threshold, a collapse threshold, and a cavitation threshold.

21. The xAM ultrasound imaging method of claim 14, wherein the threshold is a buckling threshold of an engineered harmonic gas vesicle or a resonance threshold of a microbubble.

22. The xAM ultrasound imaging method of claim 14, wherein the first and second ultrasound plane waves intersect at a plane.

23. The xAM ultrasound imaging method of claim 14, further comprising sweeping the xAM ultrasound pulse sequence to different locations by causing excitation of other subapertures of transducer elements of the one or more transducers.

24. The xAM ultrasound imaging method of claim 14, wherein the one or more transducers are also configured to detect backscatter echo signals.

25. The xAM ultrasound imaging method of claim 14 wherein the amplitudes of the first and second ultrasound plane waves are below the threshold value, and
wherein the threshold is a buckling threshold of one or more nonlinear scatterers being imaged.

26. The xAM ultrasound imaging method of claim 25,
sweeping the xAM ultrasound pulse sequence to different locations across a field of view by causing excitation of other subapertures of transducer elements of the one or more transducers; and
for each location, digitally subtracting backscatter echo signals from the first ultrasound plane wave and the second ultrasound plane wave from backscatter echo signal from simultaneous transmission of both the first and second ultrasound plane waves to generate a substantially artifact-free image of the one or more nonlinear scatterers in the field of view.

27. The xAM ultrasound imaging method of claim 26, wherein the substantially artifact-free image is a two-dimensional image or a three-dimensional image.

* * * * *

UNITED STATES PATENT AND TRADEMARK OFFICE
CERTIFICATE OF CORRECTION

| | | |
|---|---|---|
| PATENT NO. | : 11,350,909 B2 | Page 1 of 1 |
| APPLICATION NO. | : 16/387259 | |
| DATED | : June 7, 2022 | |
| INVENTOR(S) | : David Maresca, Daniel P. Sawyer and Mikhail G. Shapiro | |

It is certified that error appears in the above-identified patent and that said Letters Patent is hereby corrected as shown below:

On the Title Page

Item (72) Inventors, please add --Guillaume Renaud, Delfgauw, NL--

Signed and Sealed this
Fourth Day of November, 2025

John A. Squires
*Director of the United States Patent and Trademark Office*